(12) United States Patent
Hynes et al.

(10) Patent No.: US 12,011,398 B2
(45) Date of Patent: Jun. 18, 2024

(54) PATIENT-POSITIONING SYSTEM, COMPUTER-CONTROL AND DATA-INTEGRATION SYSTEM, SURGICAL COMPONENTRY, AND SURGICAL METHODS OF USING SAME

(71) Applicant: EMPLASE Medical Technologies, LLC, Cordova, TN (US)

(72) Inventors: Richard A. Hynes, Melbourne, FL (US); Roger P. Jackson, Prairie Village, KS (US); Matthew M. Morrison, Cordova, TN (US)

(73) Assignee: EMPLASE MEDICAL TECHNOLOGIES, LLC, Cordova, TN (US)

( * ) Notice: Subject to any disclaimer, the term of this patent is extended or adjusted under 35 U.S.C. 154(b) by 0 days.

(21) Appl. No.: 18/238,334

(22) Filed: Aug. 25, 2023

(65) Prior Publication Data
US 2024/0065911 A1 Feb. 29, 2024

Related U.S. Application Data

(60) Provisional application No. 63/401,462, filed on Aug. 26, 2022, provisional application No. 63/449,867, filed on Mar. 3, 2023.

(51) Int. Cl.
*A61G 13/00* (2006.01)
*A61B 17/70* (2006.01)
(Continued)

(52) U.S. Cl.
CPC .......... *A61G 13/0054* (2016.11); *A61B 17/70* (2013.01); *A61F 2/44* (2013.01);
(Continued)

(58) Field of Classification Search
CPC .......... A61F 2/44; A61F 2/447; A61F 2/4455; A61B 17/70; A61G 13/00; A61G 13/0054
See application file for complete search history.

(56) References Cited

U.S. PATENT DOCUMENTS

| | | |
|---|---|---|
| 7,152,261 B2 | 12/2006 | Jackson |
| 7,290,302 B2 | 11/2007 | Sharps |
| (Continued) | | |

FOREIGN PATENT DOCUMENTS

WO WO2017139548 8/2017

*Primary Examiner* — Christopher J Beccia

(57) ABSTRACT

A patient-positioning system, computer-control and data-integration system, and surgical componentry are provided. The patient-positioning system can be used to manipulate the patient prior to, during, and after surgery to globally or regionally articulate the patient's body to facilitate stabilization of the patient's spine. And the computer-control and data-integration system can be used to facilitate operation of the patient-positioning system and enabling technologies use to perform surgery. Furthermore, the surgical componentry can be used to locally articulate the patient's body and/or the stabilize patient's spine. Surgical methods of using the patient-positioning system, the computer-control and data-integration system, and the surgical componentry for improving patient health outcomes are also provided.

19 Claims, 34 Drawing Sheets
(16 of 34 Drawing Sheet(s) Filed in Color)

(51) Int. Cl.
*A61F 2/44* (2006.01)
*A61G 13/02* (2006.01)
*A61G 13/12* (2006.01)
*A61B 17/02* (2006.01)

(52) U.S. Cl.
CPC ......... *A61G 13/02* (2013.01); *A61G 13/1265* (2013.01); *A61B 2017/0256* (2013.01)

(56) References Cited

U.S. PATENT DOCUMENTS

| | | |
|---|---|---|
| 7,343,645 B2 | 3/2008 | Li |
| 7,565,708 B2 | 7/2009 | Jackson |
| 8,060,960 B2 | 11/2011 | Jackson |
| 8,381,331 B2 | 2/2013 | Sharps et al. |
| 8,584,281 B2 | 11/2013 | Diel et al. |
| 8,677,529 B2 | 3/2014 | Jackson |
| 8,707,484 B2 | 4/2014 | Jackson et al. |
| 8,719,979 B2 | 5/2014 | Jackson |
| 8,826,474 B2 | 9/2014 | Jackson |
| 8,839,471 B2 | 9/2014 | Jackson |
| 8,978,180 B2 | 3/2015 | Jackson |
| 9,180,062 B2 | 11/2015 | Jackson |
| 9,186,291 B2 | 11/2015 | Jackson et al. |
| 9,198,817 B2 | 12/2015 | Jackson |
| 9,211,223 B2 | 12/2015 | Jackson |
| 9,226,865 B2 | 1/2016 | Jackson et al. |
| 9,265,680 B2 | 2/2016 | Sharps et al. |
| 9,283,084 B1 * | 3/2016 | O'Hara ................ A61F 2/4455 |
| 9,289,342 B2 | 3/2016 | Jackson |
| 9,295,433 B2 | 3/2016 | Jackson et al. |
| 9,301,897 B2 | 4/2016 | Jackson |
| 9,308,145 B2 | 4/2016 | Jackson |
| 9,339,430 B2 | 5/2016 | Jackson et al. |
| 9,364,380 B2 | 6/2016 | Jackson |
| 9,468,576 B2 | 10/2016 | Jackson |
| 9,504,622 B2 | 11/2016 | Jackson |
| 9,510,987 B2 | 12/2016 | Jackson et al. |
| 9,622,928 B2 | 4/2017 | Jackson et al. |
| 9,636,266 B2 | 5/2017 | Jackson et al. |
| 9,713,562 B2 | 7/2017 | Perlman et al. |
| 9,757,300 B2 | 9/2017 | Jackson |
| 9,849,054 B2 | 12/2017 | Jackson |
| 9,937,094 B2 | 4/2018 | Jackson et al. |
| 10,159,618 B2 | 12/2018 | Jackson et al. |
| 10,470,959 B2 | 11/2019 | Le |
| 10,500,114 B2 | 12/2019 | Jackson et al. |
| 10,531,998 B2 | 1/2020 | Jackson et al. |
| 10,695,252 B2 | 6/2020 | Jackson |
| 10,888,481 B2 | 1/2021 | Hoel et al. |
| 10,945,905 B2 | 3/2021 | Hoel et al. |
| 11,278,462 B2 | 3/2022 | Schwardt et al. |
| 11,497,670 B2 | 11/2022 | Le |
| 2004/0133979 A1 | 7/2004 | Newkirk et al. |
| 2005/0080418 A1 * | 4/2005 | Simonson ............. A61M 29/00 606/279 |
| 2007/0192960 A1 | 8/2007 | Jackson |
| 2013/0269710 A1 | 10/2013 | Hight et al. |
| 2015/0265482 A1 | 9/2015 | Ciblak et al. |
| 2015/0272681 A1 | 10/2015 | Skripps et al. |
| 2016/0000627 A1 | 1/2016 | Jackson et al. |
| 2017/0181908 A1 | 6/2017 | Jackson et al. |
| 2019/0000705 A1 | 1/2019 | Schwardt et al. |
| 2021/0330536 A1 | 10/2021 | Lim et al. |
| 2022/0040021 A1 | 2/2022 | Ebara |
| 2024/0074930 A1 | 3/2024 | Lorman et al. |

\* cited by examiner

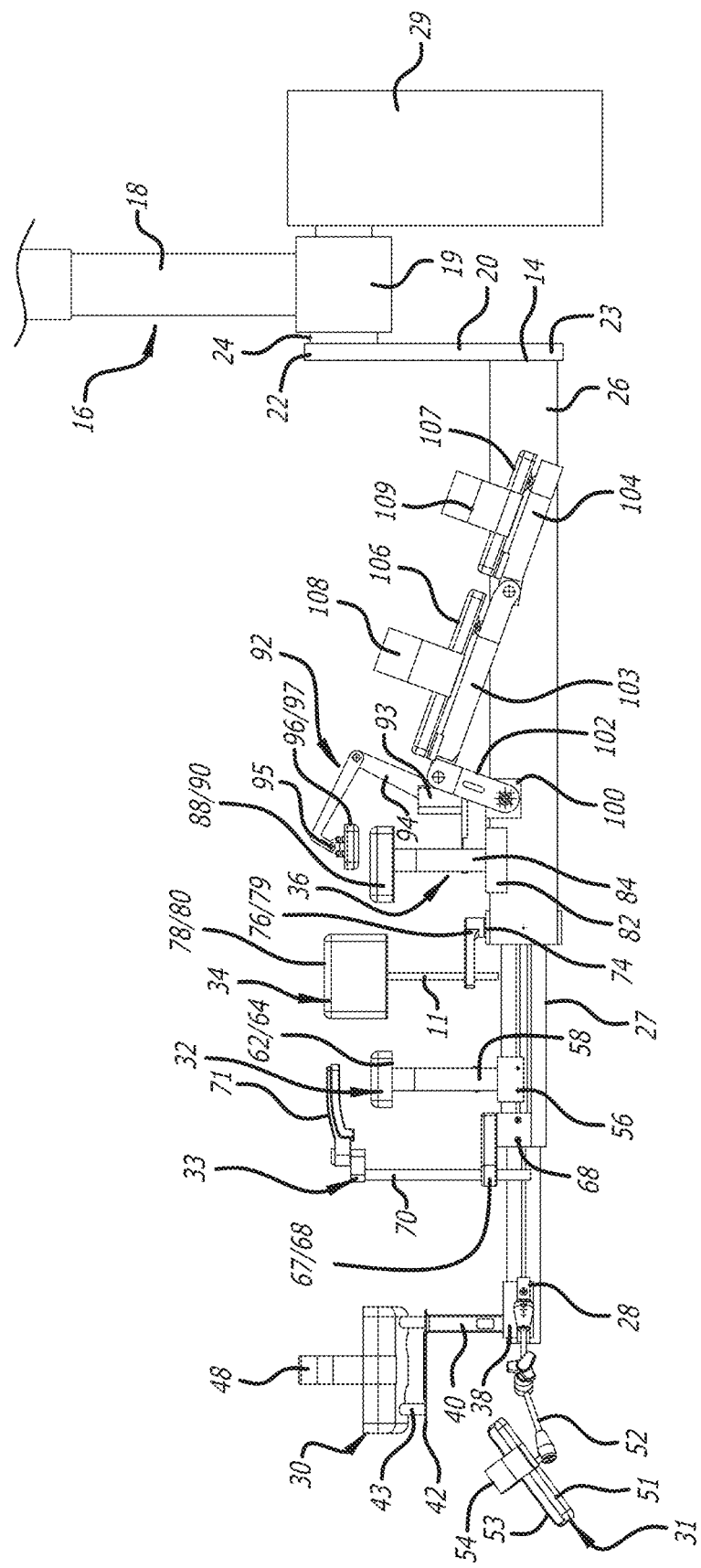

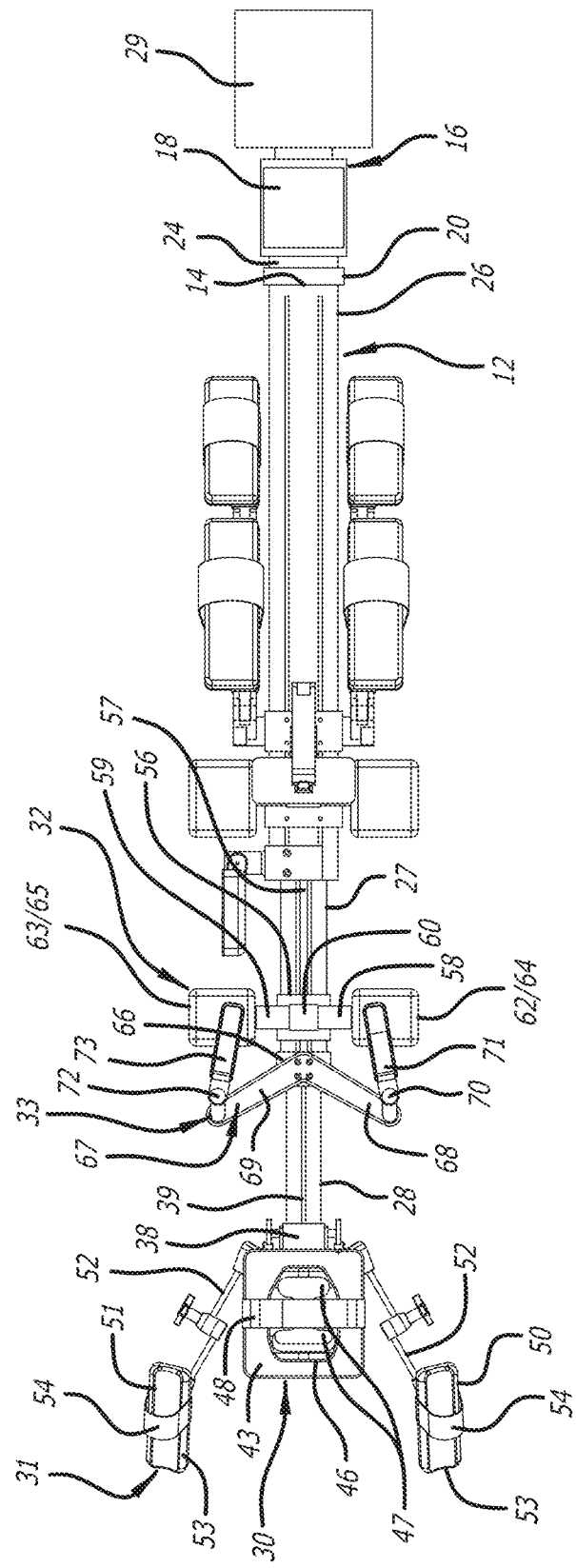

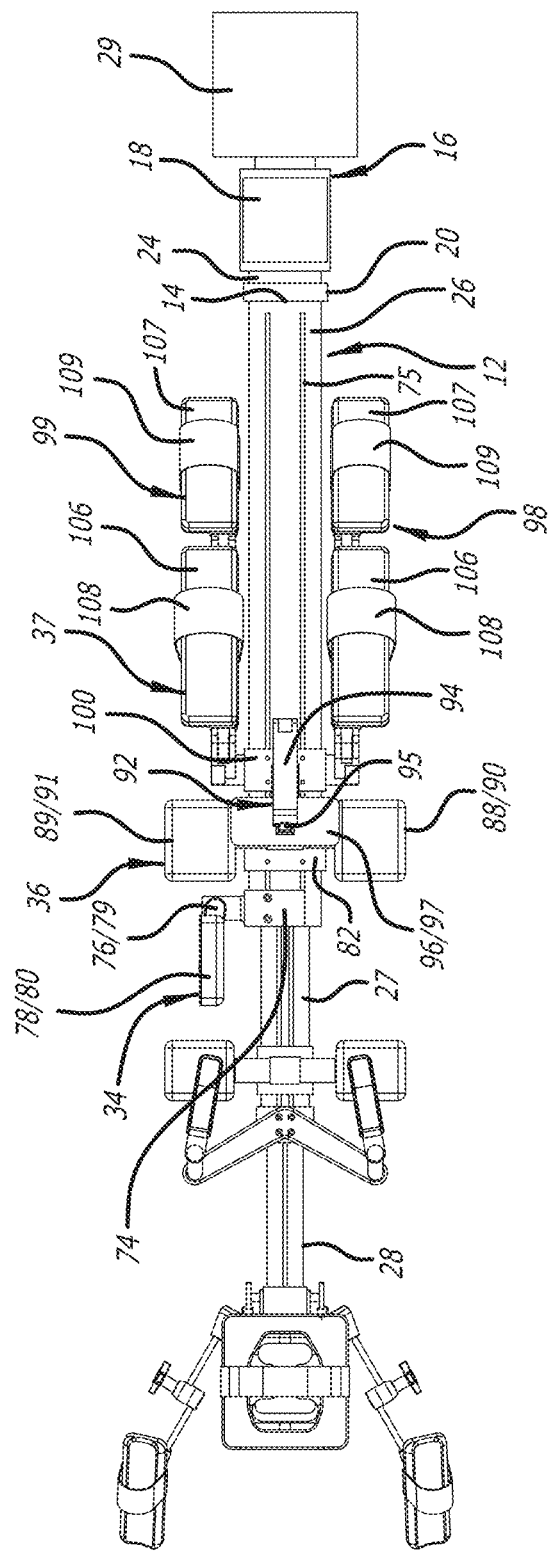

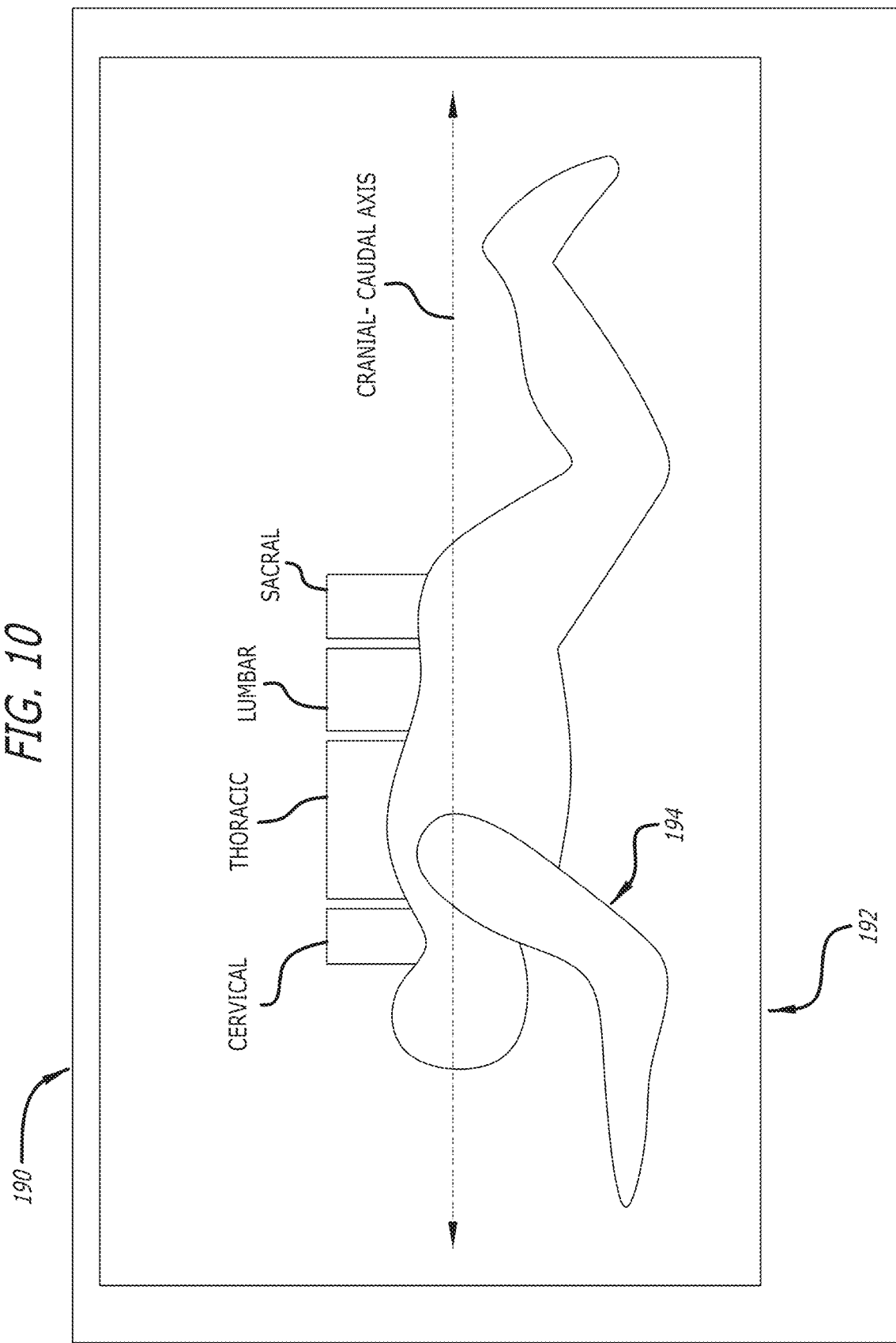

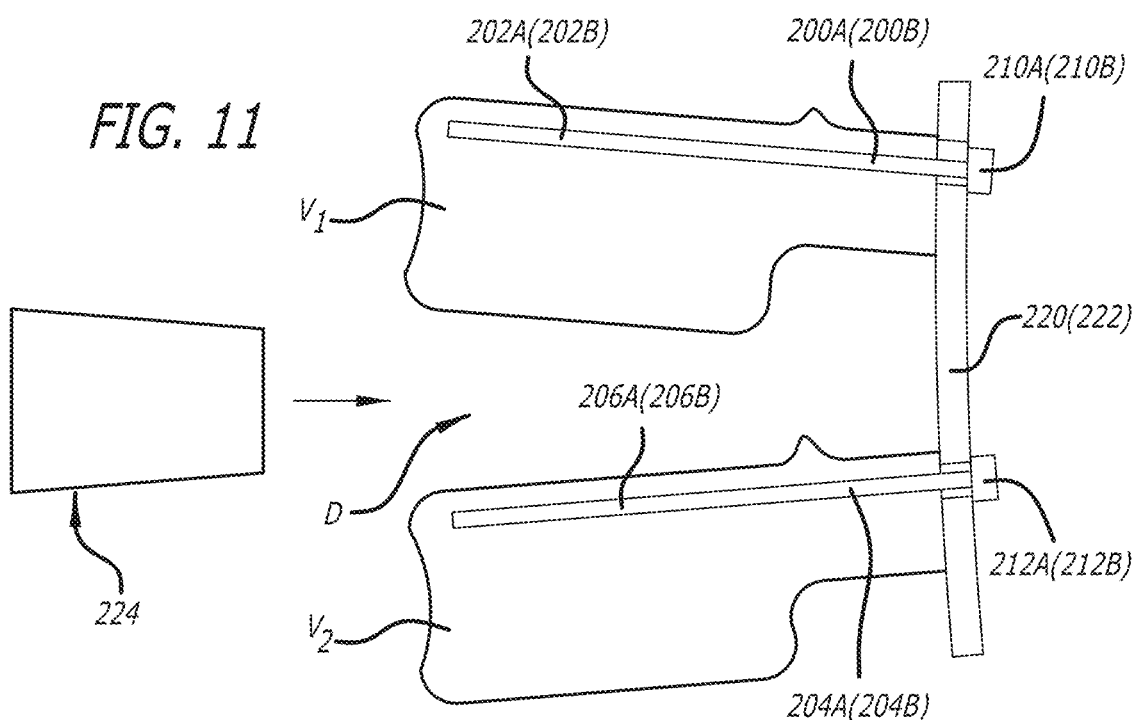
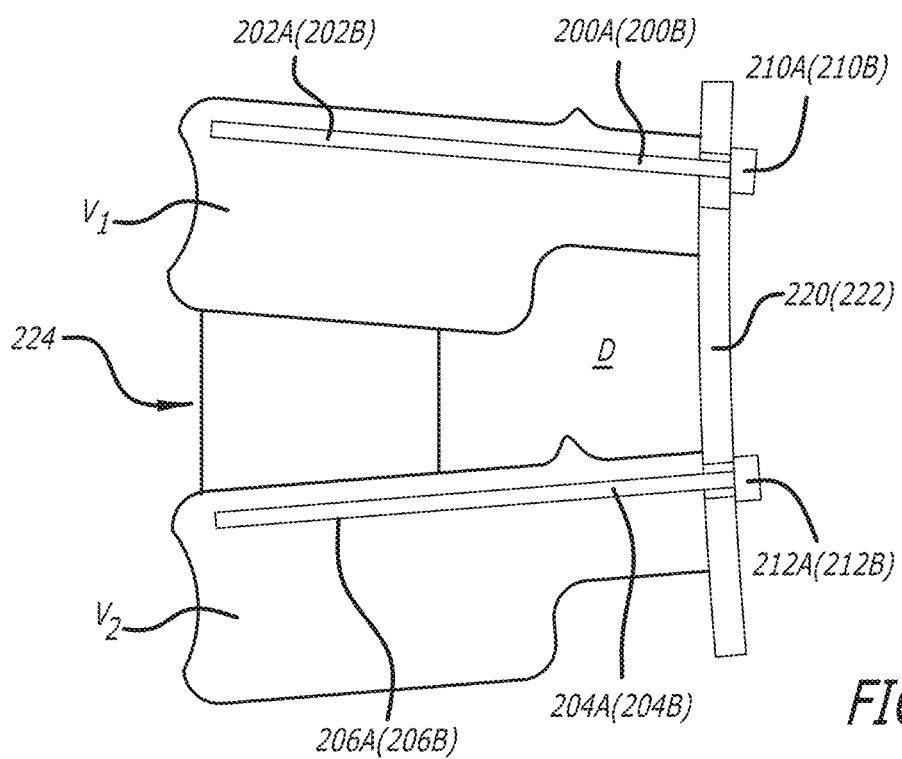

PATIENT-POSITIONING SYSTEM, COMPUTER-CONTROL AND DATA-INTEGRATION SYSTEM, SURGICAL COMPONENTRY, AND SURGICAL METHODS OF USING SAME

The present application claims benefit of Provisional Application No. 63/401,462, filed Aug. 26, 2022, and Provisional Application No. 63/449,867, filed Mar. 3, 2023; all of which are incorporated by reference herein.

BACKGROUND OF THE INVENTION

Field of the Invention

The present disclosure relates to a patient-positioning system, computer-control and data-integration system, and surgical componentry. The patient-positioning system can be used to manipulate the patient prior to, during, and after surgery to globally or regionally articulate the patient's body to facilitate stabilization of the patient's spine. And the computer-control and data-integration system can be used to facilitate operation of the patient-positioning system and enabling technologies use to perform surgery. Furthermore, the surgical componentry can be used to locally articulate the patient's body and/or the stabilize patient's spine. The present disclosure further relates to methods of using the patient-positioning system, the computer-control and data-integration system, and the surgical componentry that can be used as part of general or specific modalities of care for improving patient-health outcomes.

Background

Conventional spinal surgery has been used to address and correct some spinal deformities, degeneration, and injuries to improve patient-health outcomes. And specialized surgical tables and surgical componentry have been developed to facilitate such conventional spinal surgery. However, such conventional spinal surgery and the specialized tables and surgical componentry developed therefor has some limitations. Such specialized tables oftentimes provide limited access to some portions of the patient's spine, and such specialized surgical componentry oftentimes do not facilitate access to and stabilization of the patient's spine to a desired degree. Accordingly, there is an need for improved surgical tables and improved surgical componentry to provide increased access to and stabilization of the patient's spine to a desired degree. These improvements, as discussed below, can take the form of a patient-positioning system and improved surgical componentry that can be used with or without the patient-positioning system. These improvements can be effectuated using a computer-control and data-integration system usable during surgery to enhance use of the patient-positioning system and the improved surgical componentry. And when using the patient-positioning system, the computer-control and data-integration system, and/or the improved surgical componentry, additional systems, methods, and enabling technologies can be utilized to further facilitate improved patient-health outcomes.

SUMMARY

The subject of the present disclosure relates to a patient-positioning system, computer-control and data-integration system, and surgical componentry, and methods for using the patient-positioning system, the computer-control and data-integration system, and the surgical componentry.

In one aspect, the present disclosure provides a method of performing spinal surgery on a patient's spine, the method including providing a structure to position a patient on a patient-positioning system; articulating the patient between at least a first position and a second position; accessing a first portion of the patient via a first incision or incisions and accessing a second portion of the patient via a second incision or incisions; manipulating the first portion of the patient using a first surgical pathway via the first incisions or incisions; and manipulating the second portion of the patient using a second surgical pathway via the second incisions or incisions; where manipulation of the first portion and the second portion of the patient can occur simultaneously by different surgeons to afford parallel performance of two different surgical work-flows by the different surgeons.

In another aspect, the present disclosure provides a method of performing spinal surgery on a patient's spine, the method including providing a structure to position a patient on a patient-positioning system; articulating the patient between at least a first position and a second position; accessing a first spinal portion of the patient via a first incision or incisions and accessing a second spinal portion of the patient via a second incision or incisions; manipulating the first spinal portion of the patient using a first surgical pathway via the first incisions or incisions; and manipulating the second spinal portion of the patient using a second surgical pathway via the second incisions or incisions; where manipulation of the first spinal portion and the second spinal portion of the patient can occur simultaneously by different surgeons to afford parallel performance of two different surgical work-flows by the different surgeons; where the first spinal portion is one of a posterior portion and a lateral portion of patient's spine, and the second spinal portion is the other of the posterior portion and the lateral portion of the patient's spine; and where each of the two different surgical work-flows can include compression, decompression, alignment, and/or stabilization of the first spinal portion and the second spinal portion.

In yet another aspect, the present disclosure provides a method of performing spinal surgery on a patient's spine, the method including positioning an apparatus to position a patient on a patient-positioning system; articulating the patient between at least a first position and a second position; accessing a first spinal portion of the patient via a first incision or incisions and accessing a second spinal portion of the patient via a second incision or incisions; manipulating the first spinal portion of the patient using a first surgical pathway via the first incisions or incisions; and manipulating the second spinal portion of the patient using a second surgical pathway via the second incisions or incisions; where manipulation of the first spinal portion and the second spinal portion of the patient can occur simultaneously by different surgeons to afford parallel performance of two different surgical work-flows by the different surgeons; and where the first spinal portion is one of a posterior portion and a lateral portion of patient's spine, and the second spinal portion is the other of the posterior portion and the lateral portion of the patient's spine.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 2 is a side, elevational view of the first embodiment of the patient-positioning system depicted in FIGS. 1A-1C;

FIG. 3A is a top, plan view of the first embodiment of the patient positioning system depicted in FIGS. 1A-1C;

FIG. 3B is a top, plan view, identical to FIG. 3A, of the first embodiment of the patient positioning system depicted in FIGS. 1A-1C;

FIG. 10 is a representational view of a computer-control and data-integration system according to the present disclosure employing a computer/display displaying a manipulatable patient avatar thereon;

FIG. 11 is a lateral representational view of a level of a human spine being treated to facilitate insertion of an interbody spinal implant into a disc space between an upper vertebral body and a lower vertebral body using a first embodiment of a first distraction-aiding post inserted into the upper vertebral body and a second distraction-aiding post inserted into the lower vertebral body, and a lordotic rod engaged to the first distraction-aiding post and the second distraction-aiding post;

FIG. 12 is a lateral representational view, similar to FIG. 11, depicting the level of the human spine with the interbody implant inserted into the disc space, and the first embodiment of the first distraction-aiding post and the second distraction-aiding post adjusted in position relative to the lordotic rod;

DETAILED DESCRIPTION

Figure 1A:
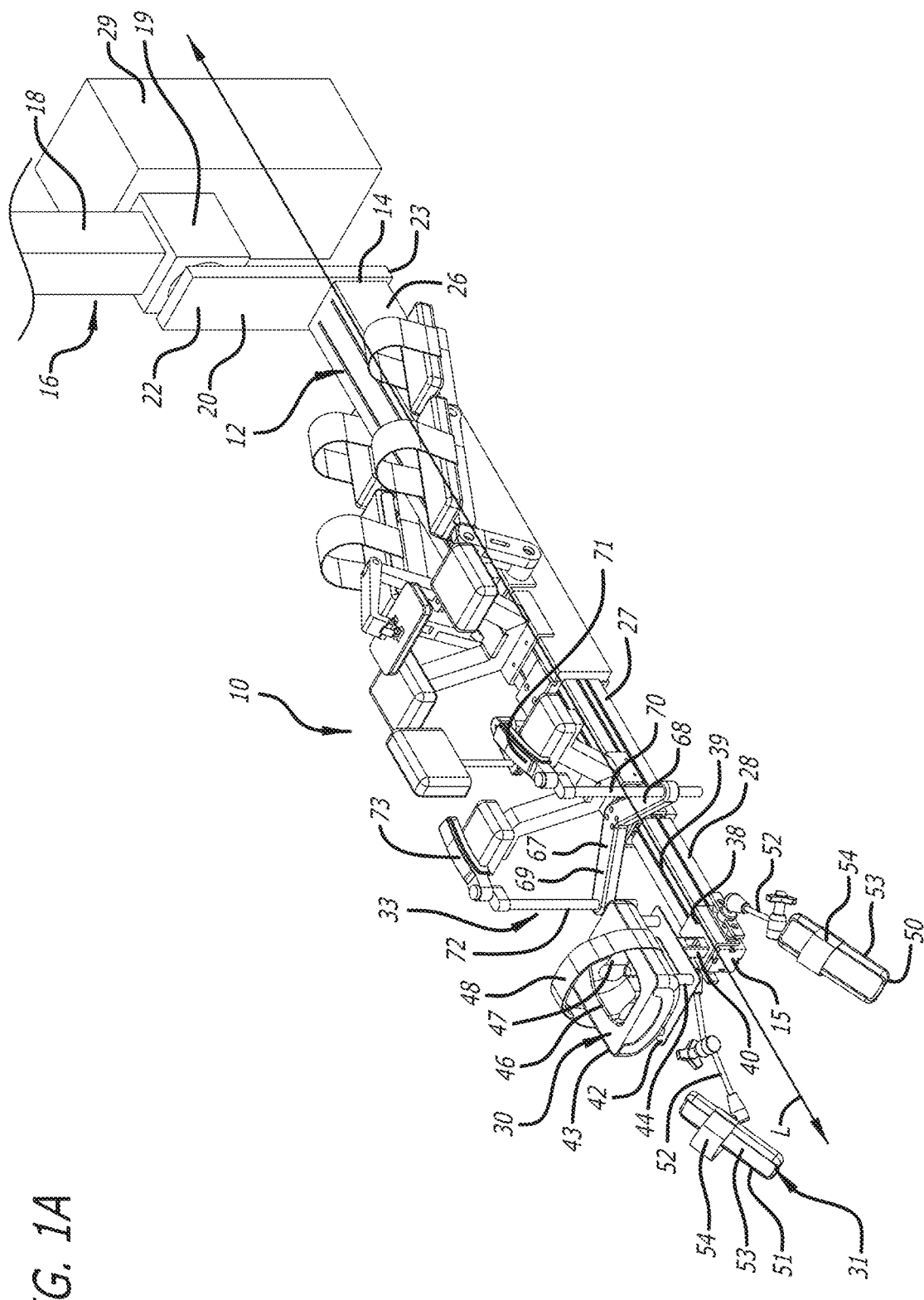
FIG. 1A is a top, side, perspective view of a first embodiment of a patient-positioning system according to the present disclosure.

I. Patient-Positioning System.

The present disclosure is directed in part to embodiments of a patient-positioning system using for manipulating a patient for surgery. A first embodiment of the patient-positioning system is disclosed in FIGS. 1A-3B and is generally indicated by the numeral 10, and a second embodiment of the patient-positioning system is disclosed in FIGS. 4-8 and is generally indicated by the numeral 110.

The patient-positioning system according to the present disclosure can be used for interoperative patient positioning and manipulation, and in doing so, can be used to support and biomechanically articulate the patient prior to, during, and after surgery, while simultaneously affording open space around portions of the patient to provide access thereto. And, as discussed below, such access can include simultaneous access to portions of the patient through different surgical pathways. When using the patient-positioning system, the patient can be articulated relative to three planes prior to, during, and after surgery, and embodiments of the patient-positioning system discussed below facilitate harmonious articulation of the patients in these three planes. The three planes include a coronal plane, a sagittal plane, and a transverse plane. The embodiments of the patient-positioning system, for example, can incorporate structure(s) to facilitate tilting of the patient to the right-side and the left-side in the coronal plane, angulation of the patient upwardly and downwardly and/or provide or extension and flexion of the patient's spine in the sagittal plane, and rotation of the patient and/or for twisting or untwisting of the patient's spine in the transverse plane. Such articulation of the patient using adjustment of structure(s) of the patient-positioning system affords access to critical areas of the patient for surgery thereon. And the articulation of the patient using the patient-positioning system can account for the coupled motion in one or more of various spinal units making up the patient's spine when the patient is articulated in one or more of the three planes.

The open space around the patient afforded by the patient-positioning system can provide considerable freedom of movement to, for example, provide one or more surgeons and other operating-room personnel, as well as other enabling technologies such as one or more surgical robots, one or more navigation systems, and/or one or more radiographic imaging devices for accessing the patient. And additional access can be provided by adjustment of portions of the patient-positioning system. Such access and adjustment can be ergonomically beneficial to the surgeon or surgeon(s). To illustrate, using the patient-positioning system, not only can the position and orientation of the patient be articulated, the position and orientation of the patient can be articulated relative to the surgeon(s) so that the surgeon(s) can efficiently access the critical areas of the patient. The use of the patient-positioning system is advantageous, because the patient can be articulated into position relative to the surgeon(s) to afford simultaneous access, simultaneous manipulation, and parallel surgical work-flows. In doing so, the patient-positioning system can be "surgeon-centric." The patient can be brought into position relative to the surgeon(s) to enhance corresponding ergonomics for the surgeon(s), and, for example, allow the surgeon(s) to remain in a single position during surgery and/or at least limit need for the surgeon(s) to move from the single position during surgery. In addition to providing such access, the articulation of the patient using the patient-positioning system during surgery can serve to prevent pressure sores, nerve injuries, ocular injuries, blood stasis and clotting, and improve breathing to prevent infection.

As discussed below, in order to provide access to the critical areas of the patient, the patient-positioning system can incorporate structure(s) used to raise and lower the patient, used for right-side and left-side lateral tilting of the patient in the coronal plane (for example, ranging from approximately 0°±15° or even more), used for upward and downward angulation of the patient, used for extension and flexion of the patient in the sagittal plane (for example, ranging between approximately 0° to ±30° or even more), and used to rotate the patient between prone, left lateral, right lateral, and supine positions in the transverse plane (for example, ranging between 0° and) 360°. And the patient-positioning system can be used to subject the patient's spine to distraction or compression for additional access to the critical areas of the patient. Furthermore, various patient supports of the patient-positioning system for directly contacting and supporting the patient can be moved into and out of position relative to the patient to provide still additional access to the critical areas of the patient. As discussed below, the simultaneous access through the different surgical pathways afforded by patient-positioning system can allow the surgeon(s), the surgical robot(s), navigation system(s), and/or the radiographic imaging device(s) to work on the patient in parallel, and such simultaneous access, for example, can afford surgery on a portion of a patient's spine from different directions. Furthermore, movement of the patient-positioning system, the surgical robot(s), navigation system(s), and/or the radiographic imaging device(s) can be synchronized with or independent from one another.

A. First Embodiment of Patient-Positioning System

A first embodiment of the patient-positioning system can include one or more beams or supports, and/or beam portions or support portions that are used in supporting the various patient supports. The one or more beams or beam portions, for example, can include a longitudinally-oriented beam having one or more beam portions attached to one another that can be substantially aligned with the cranial-caudal axis of the patient supported thereby. To illustrate, the patient-positioning system can include a first end, an opposite second end, and at least a first beam portion of the longitudinally-oriented beam, and a second beam portion of the longitudinally-oriented beam. The first beam portion can extend from the first end toward the second end and terminate at a second beam portion, and the second beam portion can extend from the first beam portion toward the second end and terminate at the second end.

The first beam portion and the second beam portion can each be telescopically adjustable to facilitate contraction and expansion of lengths thereof, and can be adjustable relative to one another. For example, each of the first beam portion and the second beam portion can be contractable and expandable between a contracted first position and an expanded first position thereof, and the first beam portion and the second beam can be telescopically and/or pivotally interconnected relative to one another to afford pivotal movement between a first angled orientation and a second angled orientation therebetween. The contraction and the expansion of the first beam portion and the second beam portion affords length adjustment of the longitudinally-oriented beam to accommodate anatomical dimensions of various patients and/or can be used to correspondingly subject the spine of the patient supported by the patient-positioning system to distraction or compression. And the pivotal interconnection of the first beam portion and the second beam portion to tilt the patient to the right-side and the left-side in the coronal plane, and/or afford accommodation of patients having spinal deformities, degeneration, and injuries.

The longitudinally-oriented beam can be supported by a supporting structure provided at a head-end or a foot-end of the patient. The supporting structure can include vertically-oriented portions(s) for supporting the longitudinally-oriented beam. For example, the vertically-oriented portion(s) can be one or more support columns supported by portions of the supporting structure. The longitudinally-oriented beam can be moveable upwardly and downwardly relative to the vertically-oriented portion(s) via a slide mechanism, and/or the vertically-oriented portions(s) can be telescopic or include telescopic portions to facilitate raising and lowering of the longitudinally-oriented beam. As such, the vertically-oriented portion(s) can be used to raise or lower the patient supported by the patient-positioning system. Additionally, the vertically-oriented portion(s) can be moveable laterally relative to portions of the supporting structure. The longitudinally-oriented beam can be supported at the lateral sides of the vertically-oriented portion(s) and/or supported at inward side(s) of the vertically-oriented portion(s) facing the longitudinally-oriented beam.

The supporting structure can include an interconnection between the longitudinally-oriented beam and the vertically-oriented portion(s) that can afford downward and upwards angulation of the longitudinally-oriented beam to angle the patient upwardly and downwardly and/or provide extension or flexion of the patient in the sagittal plane. Furthermore, the interconnection between the longitudinally-oriented beam and the vertically-oriented portion(s) can be used in rotating the longitudinally-oriented beam to rotate the patient between prone, left lateral, right lateral, and/or supine positions in the transverse plane. As such, the supporting structure can be used for raising/lowering, angulating, and rotating the longitudinally-oriented beam, and correspondingly raising/lowering, angulating, and rotating the various patient supports supported thereby. And while the supporting structure can be supported by and moveable relative to the floor of an operating room, the supporting structure and the vertically-oriented portion(s) can be supported relative to the ceiling of the operating room.

Portions of the patient can be directly contacted and supported above and/or below the longitudinally-oriented beam using the various patient supports. The various patient supports, and if necessary, various posts supporting the various patient supports relative to the longitudinally-oriented beam can be adjusted relative to the patient to facilitate support thereof prior to, during, and after surgery and facilitate access to the critical areas of the patient when supported in the various positions and orientations. Such adjustment can be used to adjust positions and orientations of the various supports and the one or more posts to articulate the patient's body and facilitate support there during and after rotation of the patient between the prone, left lateral, right lateral, and/or supine positions. The access afforded to the patient's body afforded by such adjustment of the patient-positioning system can provide, as discussed above, simultaneous access through different surgical pathways to allow, for example, the surgeon(s) and other operating-room personnel, the surgical robot(s), navigation system(s), and/or the radiographic imaging device(s) to work on the patient in parallel, and such simultaneous access, for example, can afford surgery on a portion of a patient's spine from different directions.

The various patient supports can include various armatures that can extend, retract, translate, pivot, swing, and swivel toward and away from the patient that can be supported directly by the longitudinally-oriented beam and/or by the one or more posts that extend outwardly from the longitudinally-oriented beam. The same or additional ones of the various armatures can be used to support the patient during transitions between the prone, left lateral, right lateral, and/or supine positions. Furthermore, the one or more posts can be telescopic and/or include telescopic portions, and/or can be pivotally interconnected to the longitudinally-oriented beam and/or include pivotally interconnected portions that afford positioning of the various patient supports relative to the longitudinally-oriented beam. Thus, the various patient supports also can be moveable into and out of position relative to the patient to both support and facilitate access to the critical areas of the patient prior to, during, and after surgery.

The armatures of the various patient supports can terminate in patient-contacting portions for contacting and supporting the patient. To illustrate, each of the patient-contacting portions can include a plate portion, as well as a pad or cushion portion and/or a clamp portion supported by the plate portion. The plate portions can be moveably interconnected with the armatures of the various patient supports. Adjustment of the various patient supports and moveable interconnection of the patient-contacting portions afford orientation of the cushion/clamp portions to facilitate contact with and support of portions of the patient. The pad/cushion/clamp portions can include opposing portions for capturing portions of the patient's body therebetween. Some of the patient-contacting portions are primary supports that can directly contact and capture portions of the patient's body therebetween, and some of the patient-contacting portions are ancillary supports that are simply used to directly contact and support portions of the patient's body. For example, the primary supports can be used in supporting and controlling the position of main portions of the patient's body including the thorax, the pelvis, and legs of the patient via capture thereof, and the ancillary supports can be used to support the head and other appendages of the patient's body and be positioned adjacent to the appropriate primary support. To illustrate, ancillary supports for supporting the head, right arm, and left arm of the patient can be positioned adjacent the primary support for supporting the thorax.

The adjustment of the primary and ancillary supports can be used to articulate the patient's body and facilitate support thereof during and after rotational adjustment of the patient between the prone, left lateral, right lateral, and/or supine positions using the patient-positioning system. And the access afforded to the patient's body afforded by such adjustment of the patient-positioning system can provide, as discussed above, simultaneous access through different surgical pathways to allow, for example, the surgeon(s), the surgical robot(s), navigation system(s), and/or the radiographic imaging device(s) to work on the patient in parallel, and such simultaneous access, for example, can afford surgery on a portion of a patient's spine from different directions.

The movement afforded by the longitudinally-oriented beam, the beam portions, the supporting structure, the supporting structure portions, the various patient supports including the various armatures, the one or more posts, and the primary and ancillary supports can be effectuated via manual adjustment and/or automation. When automated, various motors, actuators, transmissions, and controllers, and if necessary, counterweights can be used to facilitate adjustment of the longitudinally-oriented beam, the beam portions, the supporting structure, the supporting structure portions, the various armatures, the one or more positions, and the primary and ancillary supports. And, when the patient-contacting portions are properly positioned relative to the patient, the longitudinally-oriented beam, the beam portions, the supporting structure, the supporting structure portions, the various armatures, the one or more posts, and the primary and ancillary supports can be locked into such positions or adjusted to facilitate articulation of the patient's body.

1. Description of First Embodiment Depicted in FIGS. 1A-3B

FIGS. 1A-3B depict a patient-positioning system 10 according to the first embodiment of the present disclosure. The patient-positioning system 10 can incorporate the above-discussed features of the first embodiment of the present disclosure. The patient-positioning system 10 includes a longitudinally-oriented beam 12 having a first end 14, a second end 15, and a longitudinal axis L (FIG. 1A) extending through the first end 14 and the second end 15, and a supporting structure 16 provided adjacent the first end 14 of the longitudinally-oriented beam 12. As depicted in FIGS. 1A-2, the support structure 16 can include a telescopic beam 18 and an end portion 19 attached thereto. The telescopic beam 18 can be vertically-oriented, and can be attached relative to a ceiling or a floor of an operating room. As depicted in FIGS. 1A-2, the telescopic beam 18 is attached relative to the ceiling of the operating room. The telescopic beam 18 be expanded and contracted to move the end portion 19 between a lower first vertical position (FIGS. 1A-2) and an upper second vertical position. Because the longitudinal-oriented beam 12 is connected relative to the end portion 19, the longitudinally-oriented beam can descend and ascend relative to a floor of the operating during expansion and contraction, respectively, of the telescoping beam 18.

To interconnect the longitudinal beam 12 relative to the telescoping between, the patient-positioning system 10 can include a transverse arm portion 20 including a first end 22 and a second end 23. The first end 22 of the can be rotatably attached to the end portion 19, and the longitudinal beam 12 can be rotatably attached to the second end 23. The end portion 19 can include an actuator (not shown) and an axle 24 rotatable by the actuator. The axle 24 can be attached to the first end 22 to facilitate rotation of the transverse arm portion 20 and the longitudinally-oriented beam 12 about a first axis extending through the transverse arm portion 20 adjacent the first end 22 thereof. Furthermore, the longitudinal beam 12 can include an actuator (not shown) and an axle (not shown) rotatable by the actuator. The axle can be attached to the second end 23 to facilitate rotative of the longitudinally-oriented beam 12 about a second axis extending through the transverse arm portion 20 adjacent the second end 23 thereof. As such, the longitudinally-oriented beam 12 (and a patient supported thereon) can be rotated about the first and/or second axes.

The longitudinally-oriented beam 12 can be telescopic, and include a first portion 26, a second portion 27, and a third portion 28 configured for telescopic movement. The first portion 26 is supported relative to the supporting structure 16 via the attachment of the first end 14 of the longitudinally-oriented beam 12 to the transvers arm portion 20, the second portion 27 is at least partially expandable outwardly and contractable inwardly with respect to the first portion 26, and the third portion 28 is at least partially expandable outwardly and contractable inwardly with respect to the second portion 27. Although not shown, portions of the longitudinally-oriented beam 12 can be pivotally attached to one another to afford pivotal adjustment thereof. A counter-weight 29 can be attached to the end portion 19 opposite from the longitudinally-oriented beam to provide a counter-balance thereto. Furthermore, various patient supports can be supported relative to the longitudinally-oriented beam 12 on one of the first portion 26, the second portion 27, and the third portion 28 including a head-support portion 30, arm-support portions 31, a thorax-support portion 32, shoulder hold-down portion 33, and a lateral thorax-support portion 34. And the various patient supports also can include a pelvic-support portion 36 and a leg-support portion 37 supported by the longitudinally-oriented beam 12. As discussed below, the various patient supports can be used to support a patient in the prone position relative to the longitudinally-oriented beam.

The head-support portion 30 and the arm-support portions 31 can be attached relative to the third portion 28 of the longitudinally-oriented beam 12. As depicted in FIGS. 1A, 2, and 3A, for example, a first support collar 38 can be slidably received on the third portion 28, and the third portion 28 can include a first track portion 39 facilitating slidable movement of the first support collar 38 thereon. A locking mechanism (not shown) can be used to lock the first support collar 38 in position along the first track portion 39. And the head-support portion 30 can include a post portion 40 (that can be telescoping) that extends upwardly from the first support collar 38, and can be used to support other portions of the head-support portion 30.

As depicted in FIGS. 1A, 2, and 3A, the head-support portion 30 can include a support-plate portion 42 and a head-cradle portion 43. The support-plate portion 42 can be attached to the upstanding post portion 40, and can support the head-cradle portion 43 thereon using various pedestals 44 spacing the head-cradle portion 43 apart therefrom. Furthermore, the head-cradle portion 43 can include a depression 46 configured for contacting and supporting the head of the patient, and various apertures 47 in the depression 46 corresponding to the airways of the patient accessible. With the patient positioned in the prone position and the face of the patient received in the depression 47, the airways of the patient can be accessed via the various apertures 47, and via the space between the support-plate portion 42 and the head-cradle portion 43. A strap portion 48 also can be provided to secure the head of the patient to the head-cradle portion 43. Using the strap portion 48, the head of the patient can be captured and such capture allows, as discussed below, rotation of the patient.

The arm-support portions 31 can include a first portion 50 positioned on a first side of the first support collar 38 and a second portion positioned on a second side of the first support collar 38. Each of the first portion 50 and the second portion 51 can include an linkage portion 52, a support-plate portion 53, and a cuff portion 54. Each of the linkage portions 52 can extend outwardly from the first support collar 38, and can support and facilitating positioning and repositioning of the support-plate portions 53. The support-plate portion 53 can be convex to contact and support the forearms of the patient, and the cuff portions 54 can be used secure the forearms of the patient to the arm-support portions 31.

Figure 1B:
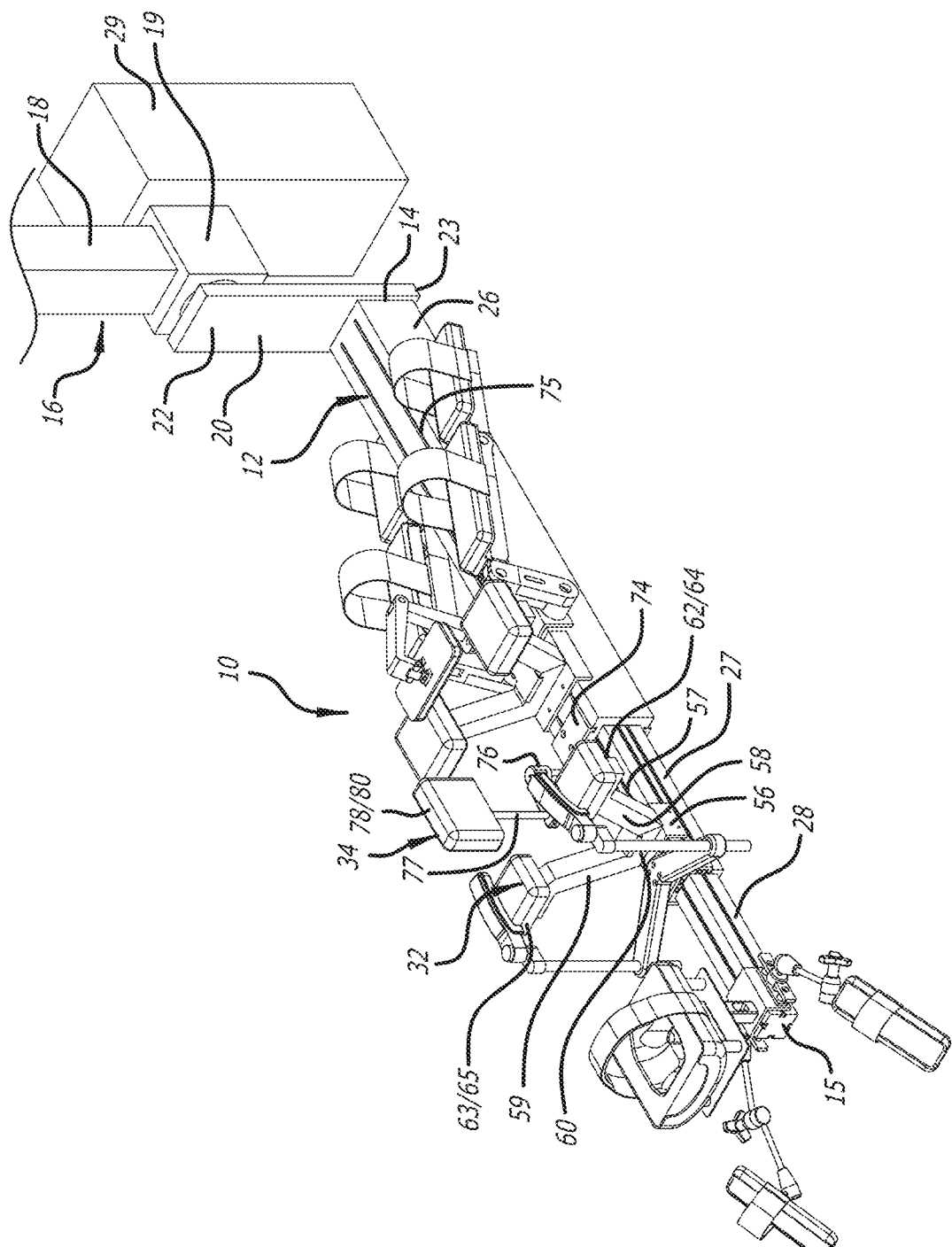
FIG. 1B is a top, side, perspective view, identical to FIG. 1A, of the first embodiment of the patient-positioning system.

The thorax-support portion 32 can be attached relative to the second portion 27 of the longitudinally-oriented beam 12. As depicted in FIGS. 1B, 2, and 3A, for example, a second support collar 56 can be slidably received on the second portion 27, and the second portion 27 can include a second track portion 57 facilitating slidable movement of the second support collar 56 thereon. A locking mechanism (not shown) can be used to lock the second support collar 56 in position along the second track portion 57. And the thorax-support portion 32 can include a first post portion 58 (that can be telescoping), a second post portion 59 (that can be telescoping), and a base portion 60. Each of the first post portion 58 and the second post portion 59 can extend upwardly and outwardly relative to the second support collar 56, and the base portion 60 can be supported by the second support collar 56 and support the first post portion 58 and the second post portion 59 thereon. The first post portion 58 and the second post portion 59 can be used to support other portions of the thorax-support portion 32.

As depicted in FIGS. 1B, 2, and 3A, the thorax-support portion 32 can include a first plate portion 62 supported by the first post portion 58, and a second plate portion 63 supported by the second post portion 59. The first plate portion 62 and the second plate portion 63 can support a first pad 64 and second pad 65, respectively, for contacting and supporting portions of the thorax of the patient. To illustrate, with the patient supported in the prone position, the first pad 64 can contact and support the left chest of the patient, and the second pad 65 can contact and support the right chest of the patient. To facilitate contact and support of the thorax of the patient using the first pad 64 and the second pad 65, the first plate portion 62 can be moveably attached to the first post portion 58, and the second plate portion 63 can be moveably attached to the second post portion 59. For example, the first plate portion 62 and the second plate portion 63 can be configured to rotate, swivel, and/or pivot toward the first end 14, toward the second end 15, toward a first lateral side of the longitudinally-oriented beam 12, toward a second lateral side of the longitudinally-oriented beam 12, and in directions therebetween. To that end, for example, ball joints (not shown) can be used to attach the first plate portion 62 to the first post portion 58 and to attach the second plate portion 63 to the second post portion 59. Such rotation, swiveling, and/or pivoting of the first plate portion 62 and the second plate portion 63 allows orientation and reorientation of the first pad 64 and/or the second pad 65 to facilitate contact thereof with the patient, and locking mechanisms (not shown) can be used to maintain such contact by locking the position of the first plate portion 62 relative to the first post portion 58 and/or locking the position of the second plate portion 63 relative to the second post portion 59.

Additional movement of the first pad 64 and the second pad 65 can be afforded by moveable attachment of the first post portion 58 and/or the second post portion 59 relative to the base portion 60 and/or the second support collar 56, and/or by moveable attachment of the base portion 60 relative to the second support collar 56. For example, the first post portion 58 and/or the second post portion 59 can be configured to rotate, swivel, and/or pivot, as discussed above, relative to the base portion 60 and/or the second support collar 56, and the base portion 60 can be configured to rotate, swivel, and/or pivot, as discussed above, relative to the second support collar 56. To that end, for example, ball joints (not shown) can be used to moveably attach the first post portion 58 relative to the base portion 60 and/or the second support collar 56, moveably attach the second post portion 59 relative to the base portion 60 and/or the second support collar 56, and/or moveably attach the base portion 60 relative to the second support collar 56. Such rotation, swiveling, and/or pivoting of the first post portion 58, the second post portion 59, and/or the base portion 60 also allows orientation and reorientation of the first pad 64 and/or the second pad 65 to facilitate contact thereof with the patient, and locking mechanisms (not shown) can be used to maintain such contact by locking the position of the first post portion 58, the second post portion 59, and/or the base portion 60 in position. Furthermore, either or both of the first post portion 58 and the second post portion 59 can be pivotally attached the base portion 60, and moveable from an upper position (FIG. 1A) to a lower position that pivots downward and away from the patient to increase access thereto. When using the pivotal feature, one of the first post portion 58 and the second post portion 59 can remain in position to facilitate support of the thorax of the patient, and the other of the first post portion 58 and the second post portion 59 can pivot downward and away to increase access to a corresponding lateral side of the patient.

The shoulder hold-down portion 33 can be attached relative to the second portion 27 of the longitudinally-oriented beam 12. As depicted in FIGS. 1A, 2, and 3A, for example, a third support collar 66 can be slidably received on the second portion 27, and be slidable along the second track portion 57 like the second support collar 56. A locking mechanism (not shown) can be used to lock the third support collar 66 in position along the second track portion 57. The shoulder hold-down portion can also be supported by the second support collar 56 instead of using the third support collar 66. And the shoulder hold-down portion 33 can include a fork portion 67 having a first extension 68 and a second extension 69. The first extension 68 can support a first post 70 and a first shoulder-contacting portion 71, and the second extension 69 can support a second post 72 and a second shoulder-contacting portion 73. The first post 70 and the second post 72 can be rotatably moveable and moveable upwardly/downwardly within apertures formed in the first extension 68 and the second extension 69, respectively, and can be locked in position relative to the fork portion 67 using locking mechanisms (not shown). The first shoulder-contacting portion 71 and the second shoulder-contacting portion 73 can be pivotally attached to the first post 70 and the second post 72, respectively, and can be correspondingly pivoted out of and into position to contact portions of the shoulders and/or back of the patient. Thus, after the left chest and the second chest of the patient are contacted to the first pad 64 and the second pad 65, the first shoulder-contacting portion 71 can be contacted to the left shoulder/back of the patient, and the second shoulder-contacting portion 73 can be contacted to the right shoulder/back of the patient. Such contact can be afforded by rotatable and upward/downward movement of the first post 70 and the second post 72, and pivotal movement of the first shoulder-contacting portion 71 and the second shoulder-contacting portion 73. With the chest and shoulders/back sandwiched or clamped between the first pad 64 and the first shoulder-contacting portion 71 and between the second pad 65 and the second shoulder-contacting portion 73, the thorax of the patient can be captured and such capture allows, as discussed below, rotation of the patient.

The lateral thorax-support portion 34 can be attached relative to the first portion 26 of the longitudinally-oriented beam 12. As depicted in FIGS. 1B, 2, and 3B, for example, a fourth support collar 74 can be slidably received on the first portion 26, and the first portion 26 can include a third track portion 75 facilitating slidable movement of the fourth support collar 74 thereon. A locking mechanism (not shown) can be used to lock the fourth support collar 74 in position along the third track portion 75. And the lateral thorax-support portion can include an arm portion 76, a post portion 77, and a support plate portion 78. The arm portion 76 can be pivotally attached relative to the fourth support collar 74 via receipt of a post 79 attached to the fourth support collar 74 through an aperture formed therein. Furthermore, the post portion 77 can be rotatably moveable and moveable upwardly/downwardly within another aperture formed in the arm portion 76, and can be locked in position relative to the arm portion 76 using a locking mechanism (not shown). The support plate portion 78 can support a pad 80, and the right lateral side of the patient can be contacted to the pad 80 via pivotable movement of the arm portion 76, and via rotatable and upward/downward movement of the post portion 77. With, as discussed above, the chest and shoulders/back sandwiched or clamped between the first pad 64 and the first shoulder-contacting portion 71 and between the second pad 65 and the second shoulder-contacting portion 73, the pad 80 of the lateral thorax-support portion 34 can be contacted to the right lateral side of the patient to allow, as discussed below, rotation of the patient. To facilitate, if necessary, contact of the pad 80 to the left lateral side of the patient, the orientation of the fourth support collar 74 on the first portion 26 of the longitudinally-oriented beam 12 can be adjusted.

Figure 1C:
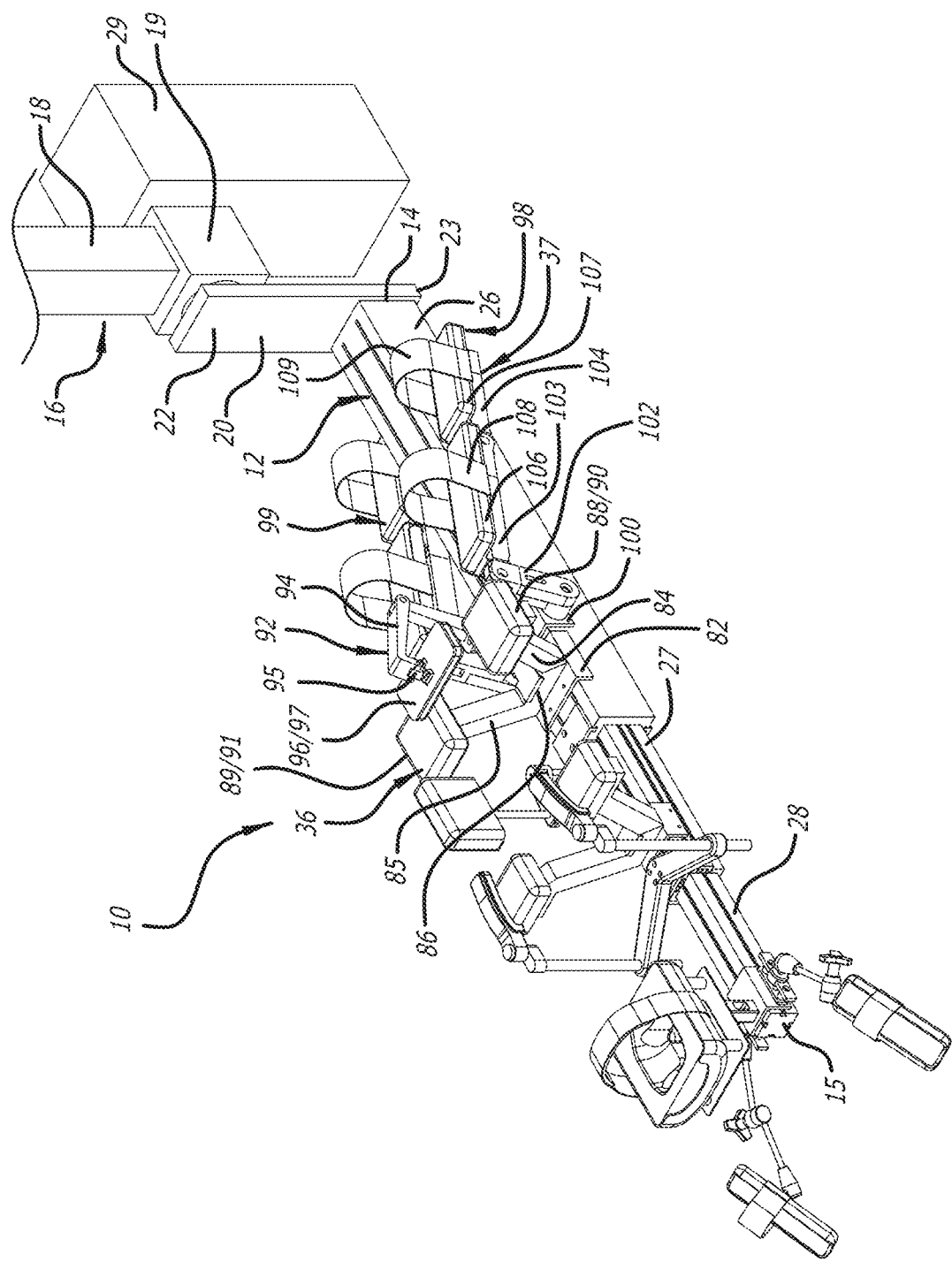
FIG. 1C is a top, side, perspective view, identical to FIGS. 1A and 1B, of the first embodiment of the patient-positioning system.

The pelvic-support portion 36 can be attached relative to the first portion 26 of the longitudinally-oriented beam 12. As depicted in FIGS. 1C, 2, and 3B, for example, a fifth support collar 82 can be slidably received on the first portion 26, and be slidable along the third track portion 75 like the fourth support collar 74. A locking mechanism (not shown) can be used to lock the fifth support collar 82 in position along the third track portion 75. And the pelvic-support portion 36 can include a first post portion 84 (that can be telescoping), a second post portion 85 (that can be telescoping), and base portion 86. Each of the first post portion 84 and the second post portion 85 can extend upwardly and outwardly relative to the fifth support collar 82, and the base portion 86 can be supported by the fifth support collar 82 and support the first post portion 84 and the second post portion 85 thereon. The first post portion 84 and the second post portion 85 can be used to support other portions of the pelvic-support portion 36.

As depicted in FIGS. 1C, 2, and 3B, the pelvic-support portion 36 can include a first plate portion 88 supported by the first post portion 84, and a second plate portion 89 supported by the second post portion 85. The first plate portion 88 and the second plate portion 89 can support a first pad 90 and second pad 65, respectively, for contacting and supporting portions of the pelvis of the patient. To illustrate, with the patient supported in the prone position, the first pad 90 can contact and support the left front pelvic area of the patient, and the second pad 91 can contact and support the right front pelvic area of the patient. To facilitate contact and support of the pelvis of the patient using the first pad 90 and the second pad 91, the first plate portion 88 can be moveably attached to the first post portion 84, and the second plate portion 89 can be moveably attached to the second post portion 85. For example, the first plate portion 88 and the second plate portion 89 can be configured to rotate, swivel, and/or pivot toward the first end 14, toward the second end 15, toward a first lateral side of the longitudinally-oriented beam 12, toward a second lateral side of the longitudinally-oriented beam 12, and in directions therebetween. To that end, for example, ball joints (not shown) can be used to attach the first plate portion 88 to the first post portion 84 and to attach the second plate portion 89 to the second post portion 85. Such rotation, swiveling, and/or pivoting of the first plate portion 88 and the second plate portion 89 allows orientation and reorientation of the first pad 90 and/or the second pad 91 to facilitate contact thereof with the patient, and locking mechanisms (not shown) can be used to maintain such contact by locking the position of the first plate portion 88 relative to the first post portion 84 and/or locking the position of the second plate portion 89 relative to the second post portion 85.

Additional movement of the first pad 90 and the second pad 91 can be afforded by moveable attachment of the first post portion 84 and/or the second post portion 85 relative to the base portion 86 and/or the fifth support collar 82, and/or by moveable attachment of the base portion 86 relative to the fifth support collar 82. For example, the first post portion 84 and/or the second post portion 85 can be configured to rotate, swivel, and/or pivot, as discussed above, relative to the base portion 86 and/or the fifth support collar 82, and the base portion 86 can be configured to rotate, swivel, and/or pivot, as discussed above, relative to the fifth support collar 82. To that end, for example, ball joints (not shown) can be used to moveably attach the first post portion 84 relative to the base portion 86 and/or the fifth support collar 82, moveably attach the second post portion 85 relative to the base portion 86 and/or the fifth support collar 82, and/or moveably attach the base portion 86 relative to the fifth support collar 82. Such rotation, swiveling, and/or pivoting of the first post portion 84, the second post portion 85, and/or the base portion 86 also allows orientation and reorientation of the first pad 90 and/or the second pad 91 to facilitate contact thereof with the patient, and locking mechanisms (not shown) can be used to maintain such contact by locking the position of the first post portion 84, the second post portion 85, and/or the base portion 86 in position. Furthermore, either or both of the first post portion 84 and the second post portion 85 can be pivotally attached the base portion 86, and moveable from an upper position (FIG. 1C) to a lower position that pivots downward and away from the patient to increase access thereto. When using the pivotal feature, one of the first post portion 84 and the second post portion 85 can remain in position to facilitate support of the pelvis of the patient, and the other of the first post portion 84 and the second post portion 85 can pivot downward and away to increase access to a corresponding lateral side of the patient.

The pelvic-support portion 36 can also include a pelvic hold-down portion 92 that, in similar fashion to the shoulder hold-down portion 33, is used to capture the pelvis of the patient. The pelvic hold-down portion 92 can include a support base 93, a pivotal armature portion 94, a pivotal connection 95, a plate portion 96, and a pad portion 97. The support base 93 can be attached to the base portion 86, and the pivotal armature portion 94 can be pivotally attached to the support base 93. Furthermore, the plate portion 96 can be pivotally attached to the pivotal arm portion 93 opposite from support base 93 via the pivotal connection 95, and the pad portion 97 can be supported by the plate portion 96. Thus, after the left front portion of the pelvis is contacted to the first pad 90, and the right front portion of the pelvis is contacted to the second pad 92, the pad portion 97 can be contacted to the buttocks of the patient via movement thereof out of and into position to facilitate such contact. Such contact of pad portion 97 can be afforded by pivotal movement of the pivotal armature portion 94 relative to the support base 93, pivotal movement of the pivotal armature portion 94 itself, and pivotal movement of the plate portion 96 relative to the pivotal armature portion 94. With the left and right front areas of the pelvis and the buttocks sandwiched or clamped between the first pad 90 and the second pad 92, and the pad portion 97, the pelvis of the patient can be captured and such capture allows, as discussed below, rotation of the patient.

The leg-support portion 37 can be attached relative to the first portion 26, and can include a first lateral portion 98 (for supporting the left leg of the patient) positioned on a first side of the first portion 26, and a second lateral portion 99 (for supporting the right leg of the patient) positioned on a second side of the first portion 26. As depicted in FIGS. 1C, 2, and 3B, for example, a sixth support collar 100 can be slidably received on the first portion 26, and be slidable along the third track portion 75 like the fourth support collar 74. A locking mechanism (not shown) can be used to lock the sixth support collar 100 in position along the third track portion 75. And the first portion 98 and the second portion 99 can each include a first link portion 102, a second link portion 103, and a fourth link portion 104. For each of the first lateral portion 98 and the second lateral portion 99, a first end of the first link portion 102 can be pinned to the sixth support collar 100, a second end of the first link portion 102 can be pinned to a first end of the second link portion 103, and a second end of the second link portion 103 can be pinned to a first end of the third link portion 104. A second end of the third link portion 104 of each of the first portion 98 and the second portion 99 can be free. Additional support linkages or struts (not shown) can be used to support and facilitate pivotal movement of the first link portion 102 relative to the sixth support collar 100, the first link portion 102 and the second link portion 103 relative to one another, and the second link portion 103 and the third link portion 104 relative to one another. In addition to the pivotal movement therebetween, each of the first link portion 102, the second link portion 103, and the third link portion 104 can be telescoping to increase or decrease the lengths thereof to afford further manipulation of the first lateral portion 98 and the second lateral portion 99 of the leg-support portion 37.

As depicted in FIGS. 1C, 2, and 3B, each of the first lateral portion 98 and the second lateral portion 99 can include a first plate/pad portion 106 attached to the second link portion 103 thereof, and a second plate/pad portion 107 attached to the third link portion 104 thereof. The first plate/pad portions 106 can be used to support the upper legs of the patient, and the second plate/pad portions 107 can be used to support the lower legs of the patient. Using pivotal movement of the first link portions 102, the second link portions 103, and the third link portions 104, the upper legs can be adjusted relative to the pelvis of the patient, and the upper legs and the lower legs can be adjusted relative to one another. Each of the first lateral portion 98 and the second lateral portion 99 can include a first cuff 108 attached relative to the second link portion 103 thereof for securing the upper legs thereto, and a second cuff 109 attached relative to the third link portion 104 thereof for securing the lower legs thereto. Using the first cuffs 108 and the second cuffs 109, the upper legs and the lower legs, respectively, can be captured and such capture allows, as discussed below, rotation of the patient.

As discussed above, the head-support portion 30 can be used to support and capture the head of the patient; the thorax-support portion 32 can be used to support and capture the thorax of the patient; the pelvic-support portion 36 can be used to support and capture the pelvis of the patient; and the leg-support portion 37 can be used to support and capture the legs of the patient. When portions of the patient's body are captured in such a manner, the patient can be rotated via rotation of the longitudinally-oriented beam 12 between prone, left lateral, right lateral, and supine positions. Additionally, the first portion 26, the second portion 27, and the third portion 28 of the longitudinally-oriented beam 12 can be rotatable with respect to another to coordinate correspondingly twisting or untwisting (or counter-rotation) the patient's spine within safety parameters preventing injury.

Furthermore, in addition to the adjustment of the head-support portion 30, the arm-support portions 31, the thorax-support portion 32, the shoulder hold-down portions 33, the lateral thorax-support portion 34, the pelvic-support portion 36, and the leg-support portion 37, the positions of the first support collar 28, the second support collar 56, the third support collar 66, the fourth support collar 74, the fifth support collar 82, and the sixth support collar 100 can be positioned and repositioned along the first track portion 39, the second track portion 57, and the third track portion 75 to accommodate patients of different heights. Furthermore, while the first support collar 28 is positioned on the third portion 28, the second support collar 56 and the third support collar 66 are positioned on the second portion 27, and the fourth support collar 74, the fifth support collar 82, and the sixth support 100 are positioned on the first portion 26, the present disclosure is not so limited. These support collars can be positioned on different ones of the first portion 26, the second portion 27, and the third portion 28 of the longitudinally-oriented beam 12.

Additionally, the padding portions of each of the head-support portion 30, the thorax-support portion 32, the lateral thorax-support portion 34, the pelvic-support portion 36, and the leg-support portion 37 can include padding for contacting the patient, and if necessary adhesives, sticky pads, and/or tape can be used to secure the patient's body relative thereto.

B. Second Embodiment of Patient-Positioning System

A second embodiment of the patient-positioning system can include two cantilevered patient support portions with a first of the cantilevered support portions being provided at the head-end of the patient, and a second of the cantilevered support portions being provided at the foot-end of the patient. One of the two cantilevered patient support portions can support the upper body of the patient and the other of the two cantilevered support portions can support the lower body of the patient. The two cantilevered support portions can move independently of one another. Actuators controlling such movement can also be independent from another, but can be choreographed with one another using the controllers to facilitate torsion, compression, traction, and rotation of the upper body and lower body of the patient. These actuators (and other actuators of the patient-positioning system) can be coordinated with movements the surgical robot(s), the navigation system(s), and/or the radiographic imaging device(s), and other tools and equipment to facilitate movement into ideal positions to facilitate the surgical goal.

The first cantilevered support portion can be supported by and extending outwardly from a first support structure at the head-end, and a second cantilevered support portion can be supported by and extending outwardly from a second support structure at the foot-end. The first support structure and the second support structure can be integrated with or separate from one another. Furthermore, like the first embodiment of the patient-positioning system, the first cantilevered support portion and the second cantilevered support portion can be supported relative to a ceiling or a floor of an operating room. The first support structure and the second support structure can each include one or more vertically-oriented portion(s) that support the first cantilevered support portion and the second cantilevered support portion, respectively, and afford movement thereof. For example, the vertically-oriented portion(s) can be one or more support columns supported by portions of the first support structure and the second support structure. Furthermore, the first cantilevered support portion and the second cantilevered support portion can be supported at the lateral sides of the vertically-oriented portion(s) and/or supported at inward side(s) of the vertically-oriented portion(s) facing the first cantilevered support portion and the second cantilevered support portion.

The vertically-oriented portion(s) of the first support structure and the second support structure can be used for raising/lowering the patient, tilting the patient to the right-side and the left-side in the coronal plane, angulating the patient upwardly and downwardly and/or providing extension or flexion of the patient in the sagittal plane, rotating the patient between prone, left lateral, right lateral, and supine positions through 360° and/or twisting or untwisting of the patient's spine in the transverse plane. To that end, the first support structure and the second support structure can include various motors, actuators, transmissions, and controllers to facilitate such movement. For example, the first support structure and the second support structure can include one or more actuators to raise and lower the first cantilevered support portion and the second cantilever support portion, respectively. Furthermore, the vertically-oriented portion(s) of the first support structure and the second support structure can each be rotatable about a vertical axis, and can correspondingly include motors to facilitate tilting of the patient to the right-side and left-side in the coronal plane. Additionally, the vertically-oriented portion(s) of the first support structure and the second support structure can each include interconnections with the first cantilevered support portion and the second cantilevered support portion and motors to facilitate angulating thereof in the sagittal plane. And the vertically-oriented portion(s) of the first support structure and the second support structure can include the same or other interconnections with the first cantilevered support portion and the second cantilevered support portion and motors to facilitate rotation thereof in the transverse plane. The vertically-oriented portion(s) of the first support structure and the second support structure also can be moveable laterally relative to portions of the first support structure and the second support structure.

Proximal ends of the first cantilevered support portion and the second cantilevered support can be interconnected and supported relative to the first support structure and the second support structure, respectively, for the movements described above. And opposite distal ends of the first cantilevered support portion and the second cantilevered support portion can be attached to one another or separated from one another by a gap. An upper portion of the patient can be supported by the first cantilevered support portion, and a lower portion of the patient can be supported by the second cantilevered support portion. The first cantilevered support portion and the second cantilevered support portion can incorporate the above-discussed various patient supports including the various armatures, the one or more posts, and the primary and ancillary supports of the first embodiment to support the patient thereon. Portions of the patient can be supported above and/or below the first cantilevered support portion and the second cantilevered support portion using the various patient supports. When the positions and orientations of the first cantilevered support portion and the second cantilevered support portions are adjusted, the upper and lower portions of the patient's body can be articulated relative to one another to tilt the patient to the right-side and the left-side in the coronal plane, angulate the patient upwardly and downwardly and/or provide extension or flexion of, for example, the thoracic and lumbar portions the patient's spine in the sagittal plane, and/or rotate the patient between prone, left lateral, right lateral, and supine positions through 360° or twist or untwist the patient's spine in the transverse plane. When twisting or untwisting the patient's spine, the first cantilevered support portion and the second cantilevered support portion can be rotated in opposite directions to correspondingly adjust the patient's spine within safety parameters preventing injury. The movement of first cantilevered support portion and the second cantilevered support portion, and other movement of the second embodiment of the patient-positioning system can be effectuated via manual adjustment and/or automation using various motors, actuators, transmissions, and controllers.

The distal ends of the first cantilevered portion and the second cantilevered portion can be pivotally connected to one another by a universal joint that affords articulation therebetween. A pin or pins can be used to maintain the pivotal connection, and when the pin or pins are removed, the first cantilevered portion and the second cantilevered portion can be disconnected from one another. Furthermore, a pivot point between the first cantilevered portion and the second cantilevered portion is created at the universal joint, and that pivot point would correspondingly create a pivotal axis between the upper and lower portions of the patient's body relative to one another. Furthermore, when the first cantilevered portion and the second cantilevered portions are not pivotally connected to one another, a virtual pivot point between the first cantilevered portion and the second cantilever also be created via constraining the relative movement thereof, and that virtual pivot point also would correspondingly create a virtual pivotal axis between the upper and lower portions of the patient's body.

The adjustment of the first cantilevered portion and the second cantilevered portion with respect to one another can be used to articulate the patient's body and facilitate support thereof during and after rotational adjustment of the patient between the prone, left lateral, right lateral, and/or supine positions using the patient-positioning system. And the access afforded to the patient's body afforded by such adjustment of the patient-positioning system can provide, as discussed above, simultaneous access through different surgical pathways to allow, for example, the surgeon(s), the surgical robot(s), navigation system(s), and/or the radiographic imaging device(s) to work on the patient in parallel, and such simultaneous access, for example, can afford surgery on a portion of a patient's spine from different directions.

1. Description of Second Embodiment Depicted in FIGS. 4-8

Figure 4:
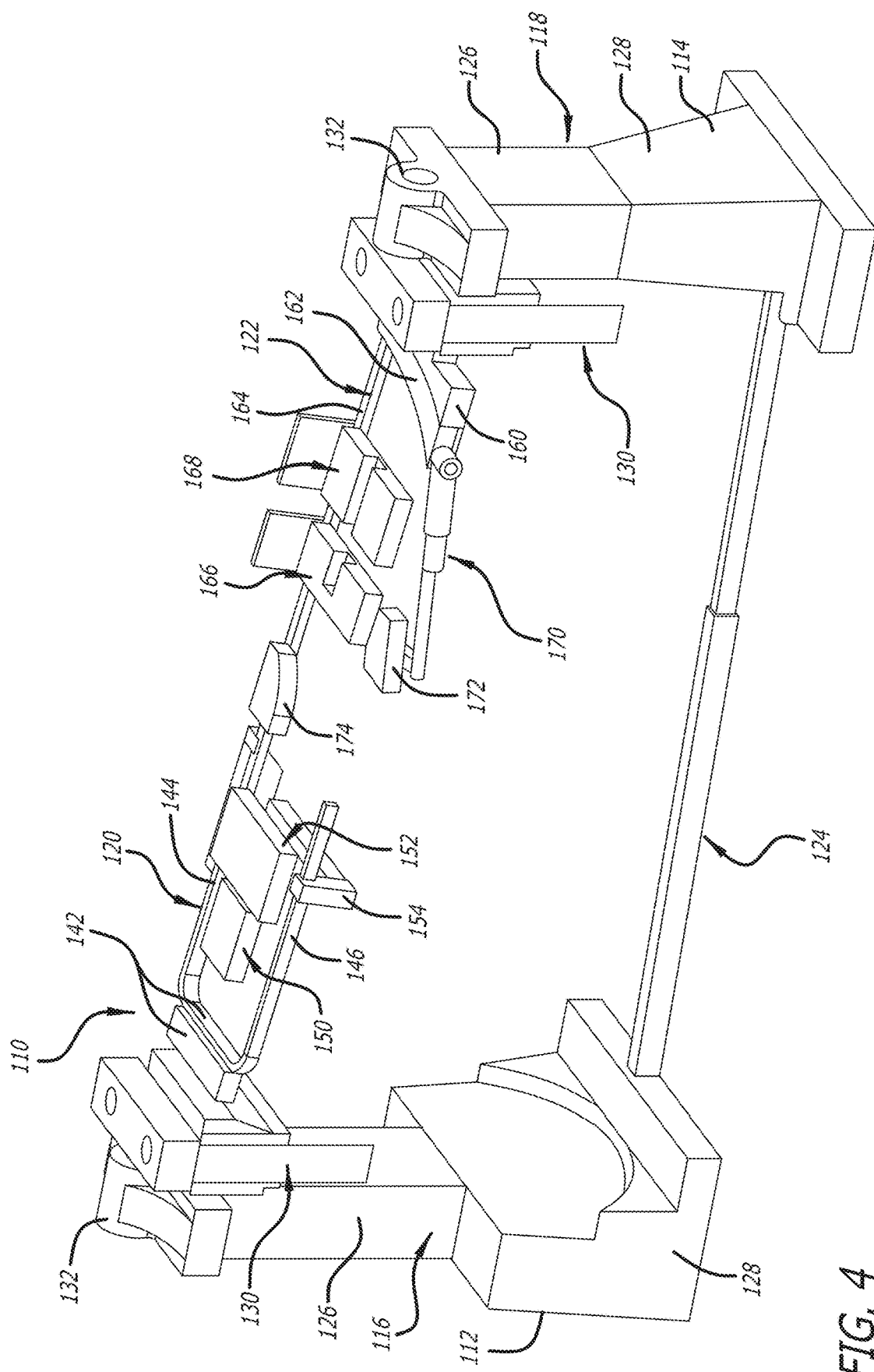
FIG. 4 is a top, side, perspective view of a second embodiment of a patient-positioning system according to the present disclosure.
Figure 5:
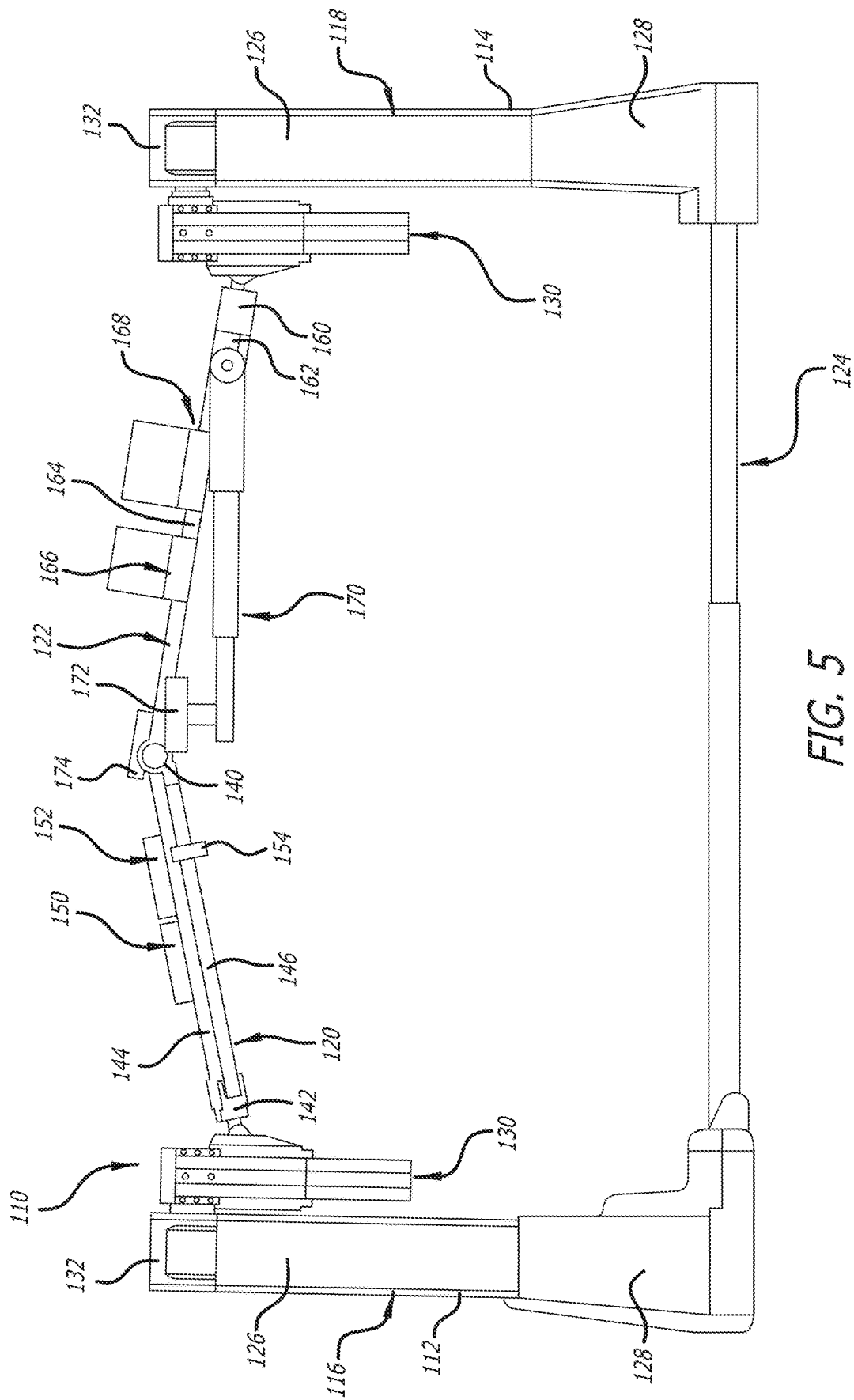
FIG. 5 is a side, elevational view of the second embodiment of the patient-positioning such of FIG. 4.
Figure 6:
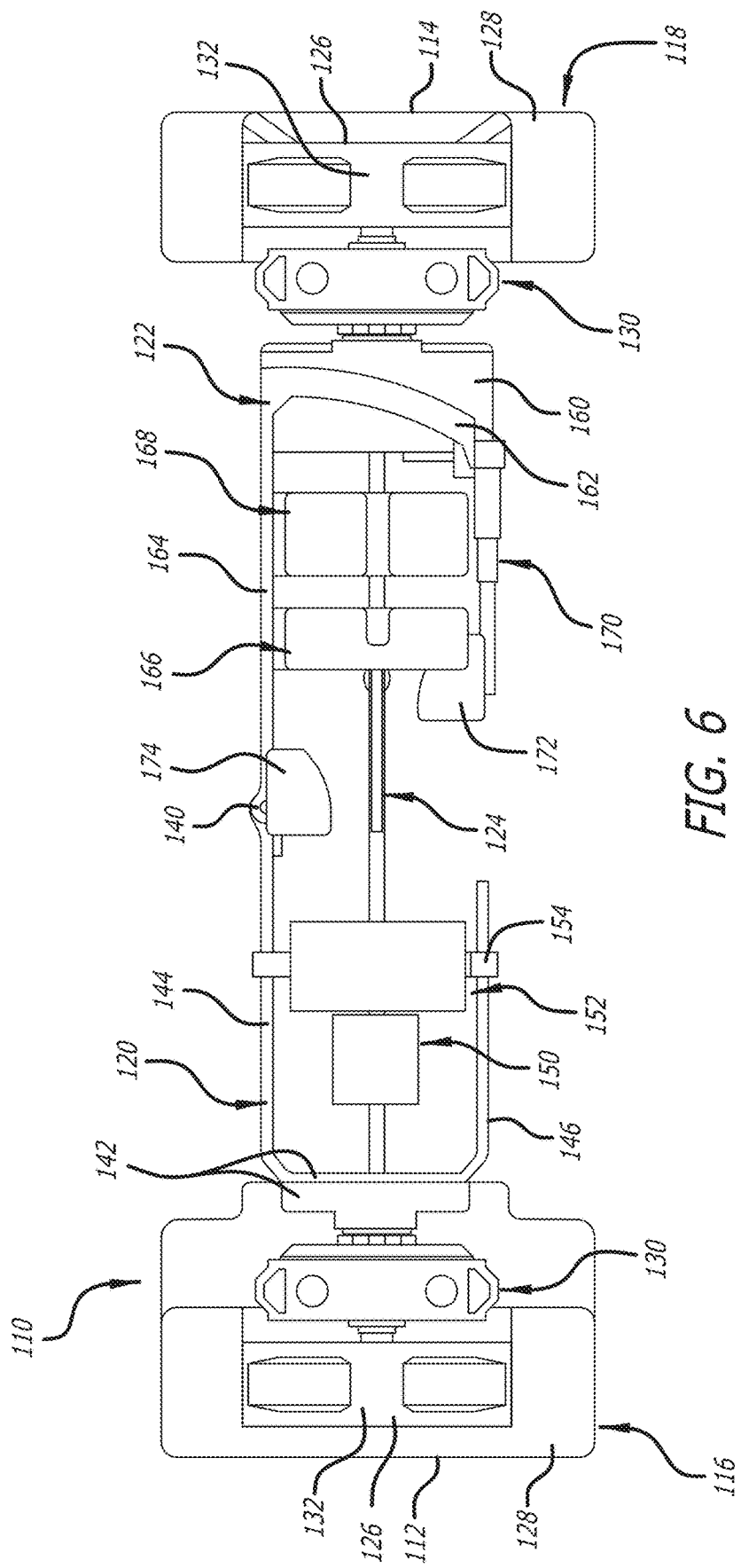
FIG. 6 is a top, plan view of the second embodiment of the patient-positioning system of FIG. 4.

FIGS. 4-8 depict a patient-positioning system 110 according to the second embodiment of the present disclose. The patient-positioning system 110 can incorporate the above-discussed features of the second embodiment of the present disclosure. As depicted in FIGS. 4-6, the patient-positioning system 110 includes a first end 112, an opposite second end 114, a first support structure 116 at the first end 112, and a second support structure 118 at the second end 114. The first support structure 116 can moveably support a first cantilevered support portion 120, and the second support structure 118 can moveably support a second cantilevered support portion 122. Furthermore, the first support structure 116 and the second support structure 118 can be separated from or interconnected to one another. As depicted in FIGS. 4-6, a longitudinal beam 124 extends between the first support structure 116 and the second support structure 118. The length of the longitudinal beam 124 can be expanded and contracted using an actuator or actuators (not shown).

Portions of the first support structure 116 and the second support structure 118 can be similar to and include features of similar structures in U.S. Pat. No. 7,343,635, which is hereby incorporated by reference herein, for supporting the first cantilevered support portion 120 and the second cantilevered support portion 122. Portions of the first support structure 116 and the second support structure 118 also can be similar to and include features of U.S. Pat. No. 9,402,775, which is hereby incorporated by reference herein, for supporting the first cantilevered support portion 120 and the second cantilevered support portion 122.

The first support structure 116 and the first cantilevered support portion 120 can be used in supporting the head and the upper torso of the patient, and the second support structure 118 and the second cantilevered support portion 122 can be used in support the pelvis and legs of the patient. As such, the first support structure 116 and portions of the first cantilevered support portion 120 are positioned at the head-end of the patient, and the second support structure 118 and portions of the second cantilevered support portion 122 are positioned at the foot-end of the patient.

As depicted in FIGS. 4 and 5, the first support structure 116 and the second support structure 118 each can include vertically-oriented portions including one or more support columns 126 and base portions 128 supporting the support columns 126. Furthermore, each of the columns 126 can be configured to facilitating raising and lowering the first cantilevered support portion 120 and the second cantilevered support portion 122, respectively. To raise and lower the first cantilevered support portion 120 and the second cantilevered support portion 122, the columns 126 can be expandable and contractable between an expanded first configuration and an unexpanded second configuration using an actuator or actuators (not shown), and/or the columns 126 can include tracks and trucks moveable upwardly and downwardly on the tracks using an actuator or actuators (not shown), and the first cantilevered support portion 120 and the second cantilevered support portion 122 can be supported relative to the trucks. Additionally, the longitudinal beam 124 can extend between the each of the base portions 128, and expansion and contract of the longitudinal beam 124 can be used to correspondingly move the first support structure 116 and the second support structure 118 toward and away from one another.

The first support structure 116 and the second support structure 118 can include portions configured for tilting portions of the patient to the right-side and the left-side in the coronal plane, angulating the patient upwardly and downwardly and/or providing extension or flexion of the patient's spine in the sagittal plane, and/or rotating the patient between prone, left lateral, right lateral, and supine positions through 360° or twisting or untwisting the patient's spine in the transverse plane. To that end, each of the first support structure 116 and the second support structure 118 can include rack portions 130 that are rotatably attached relative to the support columns 126, to which the first cantilevered support portion 120 and the second cantilevered support portion 122 can be pivotally attached, and on which heights of the first cantilevered support portion 120 and the second cantilevered support portion 122 can be adjusted. The rack portions 130 each can include a fail-safe mechanism preventing disconnection of the first cantilevered portion 120 and the second cantilevered portion 122 therefrom.

The rack portions 130 can each be rotatable via interconnection with actuators 132 supported by the columns 126, and actuation of the actuators 132 can be used to rotate the first cantilevered portion 120 and the second cantilevered portion 122 to rotate the patient between prone, left lateral, right lateral, and supine positions through 360° or twisting or untwisting the patient's spine in the transverse plane. The patient can be angulated via pivoting of the first cantilevered portion 120 and the second cantilevered portion 122 upwardly and downwardly relative to the rack portions 130 via the pivotal attachment thereof using an actuator or actuators (not shown) provided in the rack portions 130, and as necessary, via adjustment of the heights of the first cantilevered portion 120 and the second cantilevered portion 122 on the rack portions 130, raising and lowering of the columns 126 via expansion/contraction of the columns 126, and/or movement of the trucks along the tracks. And the longitudinal beam 124 can be expanded and contracted between an expanded first configuration and an unexpanded second configuration to accommodate the pivoting of the first cantilevered support portion 120 and the second cantilevered support portion 122 to angulate the patient.

Figure 9:
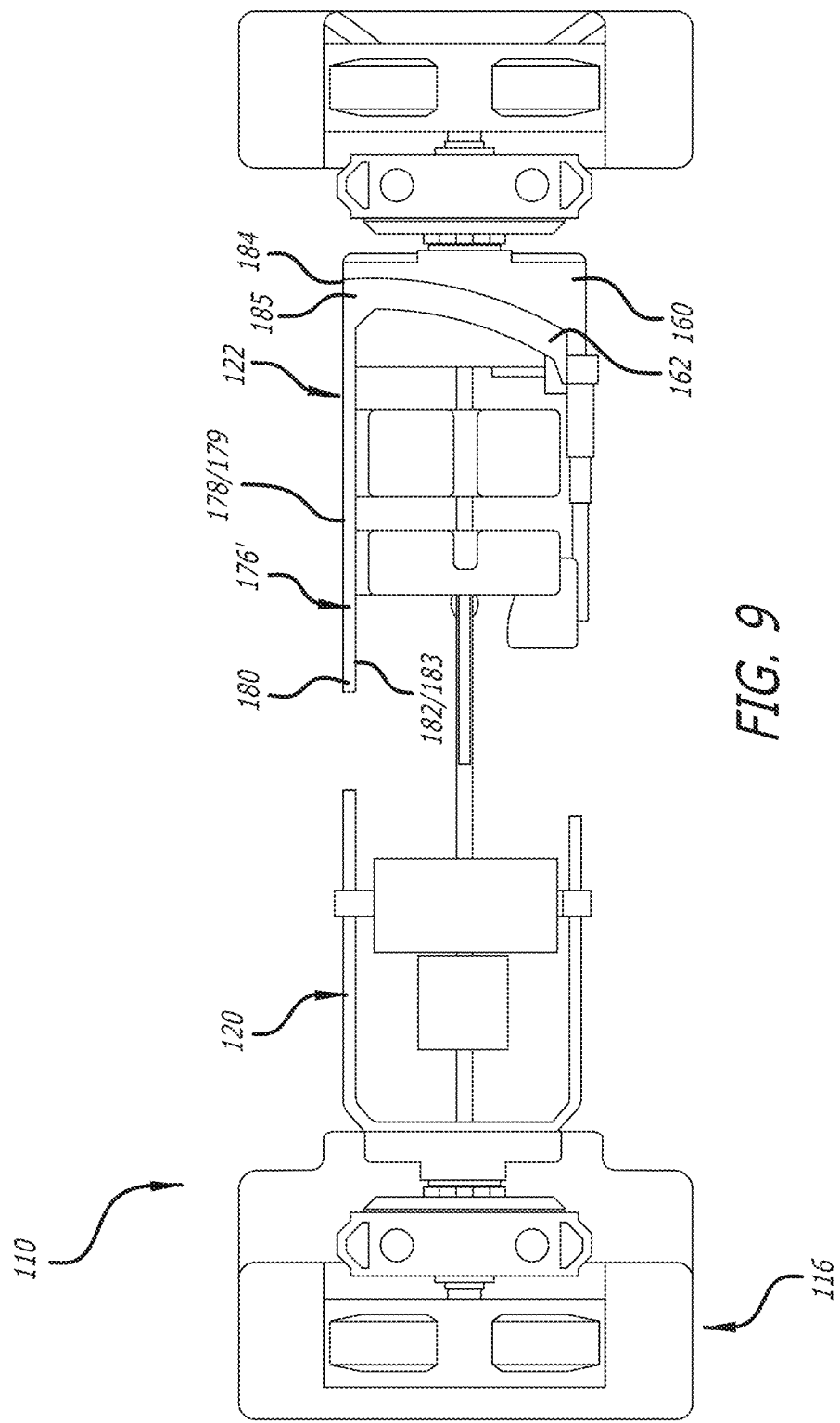
FIG. 9 is a top, plan view of a modified version of the second embodiment of the patient-positioning system of FIG. 4.

The first cantilevered support portion 120 and the second cantilevered support portion 122 can be moveably attached to one another via a universal joint 140. The universal joint 140 can afford pivotal movement between the first cantilevered support portion 120 and the second cantilevered support portion 122. The universal joint 140 can be disconnectable to facilitate detachment of the first cantilevered support portion 120 and the second cantilevered support portion 122 relative to one another. When the universal joint 140 joins the first cantilevered support portion 120 and the second cantilevered support portion 122, adjustment of the first cantilevered support portion 120 and the second cantilevered portion 122, as discussed above, can require a degree of coordination to prevent unwanted binding portions of the patient-positioning system 110 during movement thereof. As depicted in FIG. 9, the patient-positioning system 10 can be modified such that the first cantilevered support portion 120 and the second cantilevered support portion 122 are separated from one another without a moveable connection therebetween. Either way, the movement of the first cantilevered support portion 120 and the second cantilevered support portion 122 can be constrained or deactivated to prevent injury to the patient.

The first cantilevered support portion 120 can include an end portion 142, a first side portion 144, and a second side portion 146. The first cantilevered support portion 120 can be moveably attached, as discussed above, relative to the rack portion 130 of the first support structure 116 via moveable attachment of the end portion 142 thereto. The first side portion 144 and the second side portion 146 are opposite from one another and extend outwardly from the end portion 142, and the first side portion 144 can extend from the end portion 142 to the universal joint 140. Additionally, the first cantilevered support portion 120 can include various patient support portions for supporting corresponding portions of the patient thereon. The first cantilevered support portion 120 can support a head-support portion 150 and a thorax-support support portion 152 using a cradle portion 154 moveable along the first side portion 144 and the second side portion 86. Portions of the cradle portion 154 can slide along the first side portion 144 and the second side portion 146 to facilitate proper positioning of the head-support portion 150 and the thorax-support portion 152. Furthermore, the head-support portion 150 and the thorax-support portion 152 can each include padding for contacting and supporting the patient.

Figure 7:
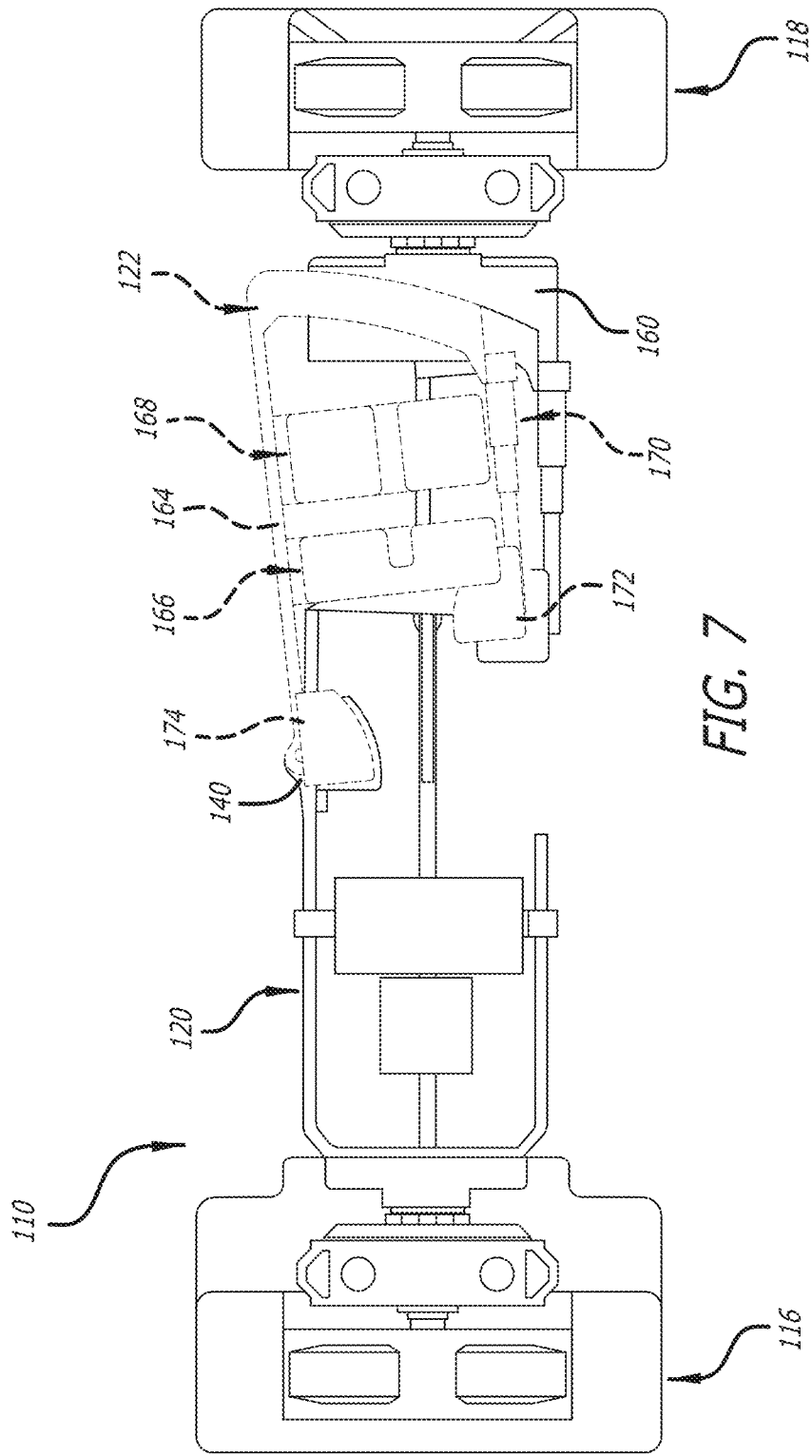
FIG. 7 is a top, plan view, similar to FIG. 6, showing movement of portions of a cantilevered portion of the second embodiment of the patient-positioning system of FIG. 4 in a first direction.
Figure 8:
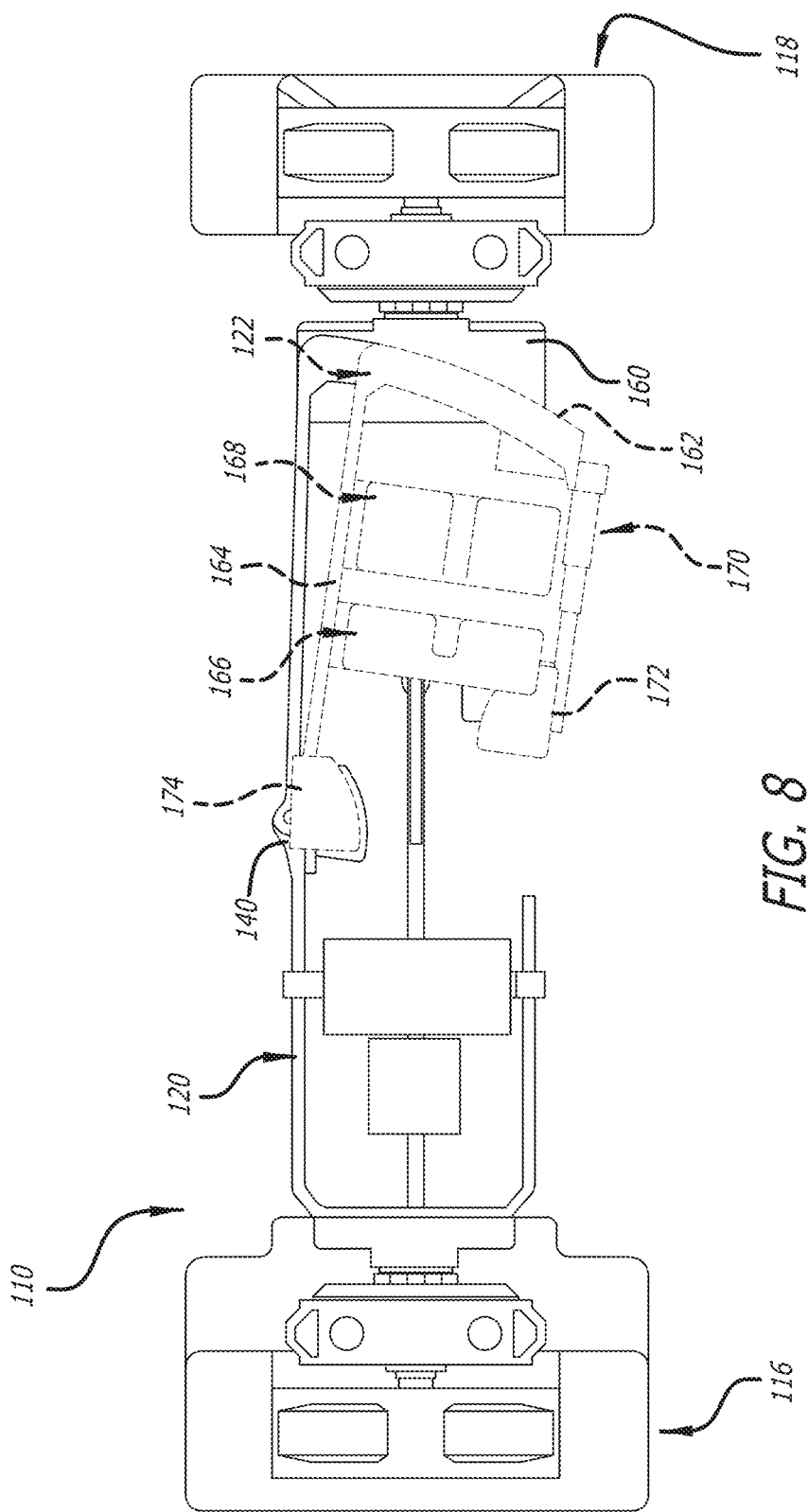
FIG. 8 is a top, plan view, similar to FIGS. 6 and 7, showing movement of the portions of the cantilevered portion of the second embodiment of the patient-positioning system of FIG. 4 in a second direction opposite the first direction.

The second cantilevered support portion 122 can include a base portion 160, an end portion 162, and a side portion 164. The second cantilevered support portion 122 can be moveably attached, as discussed above, relative to the rack portion 130 of the second support structure 118 via moveable attachment of the base portion 160 thereto. The end portion 162 and the side portion 164 also can be moveable relative to the base portion 160. As depicted in FIGS. 6-8, the side portion 164 can extend from the end portion 162 to the universal joint 140, and be pivotally attached relative to the first side portion 144 of the first cantilevered support portion 120. The moveable relationship of the end portion 162 with respect to the base portion 160 allows the end portion 162 and the side portion 164 to pivot relative to the universal joint 140 between a first position (FIG. 7) and a second position (FIG. 8). As discussed below, the pivotal movement (via movement of the end portion 162 relative to the base portion 160) affords tilt of portions of the patient to the right-side and the left-side in the coronal plane. Additionally, the second cantilevered support portion 122 can include various patient support portions for supporting corresponding portions of the patient thereon. The side portion 164 can support an upper-leg support portion 166 and a lower-leg support portion 168. Additionally, the end portion 162 can support a moveable pelvic support 170 with a first pelvic-support portion 172, and the side portion 164 can support a second pelvic-support portion 174. The moveable pelvic support 170 can be telescopic to expand and contact to facilitate engagement with and disengagement from a pelvic area of the patient. Furthermore, the first pelvic-support portion 172, the second pelvic-support portion 174, the upper-leg support portion 166, and the lower-leg support portion 168 can include padding for contacting and support the patient.

The movement of the of the end portion 162 and the corresponding right-side and left-side tilting of the lower portion of the body of the patient in the coronal (FIGS. 7 and 8) plane can be used to open access to one of the lateral sides thereof. Such access can be afforded by moving the patient's iliac crest down and away from the patient's ribs and correspondingly moving the skin of the patient closer to the patient's spine. The movement of the end portion 162 and the corresponding right-side and left-side tilting of the lower portion of the body of the patient in the coronal plane can also be used in straightening the patient's spine to correct, for example, degenerative lumbar scoliosis.

When the patient-positioning system 110 is modified such that the first cantilevered support portion 120 and the second cantilevered support portion 122 are separated from one another without a moveable connection therebetween, a modified side portion 176', as depicted in FIG. 9, including a first portion 178 and a second portion 179 can be used instead of side portion 164. To illustrate, portions of the first portion 178 and the second portion 179 can be stacked together, and portions thereof can be pivotally connected to one another via a pivotal connection 180 at a first end 182 of the first portion 178 and a first end 183 of the second portion 179. Furthermore, the first portion 178 can include a second end 184 attached to the base portion 160, and the second portion 179 can include a second end 185 attached to the end portion 162. The pivotal attachment of the first ends 182 and 183 allows the end portion 162 and the second portion 179 of the modified side portion 176' to pivot relative to the base portion 160 and the first portion 178 of the modified portion 176' to, as discussed able, tilt portions of the patient to the right-side and the left-side in the coronal plane.

While the second cantilevered portion 122 is shown having the pivotal portions that facilitate tilting of the lower portion of the body of the patient to the right-side and the left-side in the coronal plane, the first cantilevered support portion 120 can be similarly equipped to facilitate tilting of the upper portion of the body of the patient in the coronal plane. Furthermore, the head-support portion 150, the thorax-support portion 152, the first pelvic-support portion 172, the second pelvic-support portion 174, the upper-leg support portion 166, and/or the lower-leg support portion 168 can include clamping portions that (along with adhesives, sticky pads, and/or tape) can be used to fixedly hold the patient in position with respect thereto. Furthermore, the thorax-support portion 152 and the pelvic-support portion 174 can be configured similarly to the thorax-support portion 32 and the pelvic-support portion 36 described above. Such fixation can allow the patient to be rotated 360° using the patient-positioning system 110. Furthermore, the rotation of the patient's thorax and pelvis in opposite directions using the patient-positioning system 110 can be coordinated to twist or untwist the patient's spine within safety parameters preventing injury.

II. Surgical Planning and Surgery Using Computer-Control and Data-Integration System, Patient-Positioning System, Surgical Robot(s), Navigation System(s), and/or Radiographic Imaging Device(s).

The positions and orientations of the longitudinally-oriented beam, the beam portions, the supporting structure, portions of the supporting structure, the various armatures, the one or more posts, and the primary and ancillary supports of the first embodiment of the patient-positioning system prior to, during, and after surgery could be preplanned and/or controlled depending on the surgery being performed. Furthermore, the positions and orientations of the first support structure, the second support structure, portions of the support structures, the first cantilevered support portion, the second cantilevered support portion, the various armatures, the one or more posts, and the primary and ancillary supports of the second embodiment of the patient-positioning system prior to, during, and after surgery also could be preplanned and/or controlled depending on the surgery to being performed.

A computer-control and data-integration system 190, as depicted in FIG. 10, can control the position and orientation of the patient via control of the positions of the patient-positioning system (such as, for example, the first embodiment 10 and the second embodiment 110 thereof) via control of the motors, actuators, transmissions, and/or controllers thereof, and receive and integrate information collected from motors, actuators, transmissions, and/or controllers, and various operating-room equipment used in performing the surgery. As seen in FIG. 10, the computer-control and data-integration system 190 can employ a computer/display 192 and a patient avatar 194 displayed thereon viewable prior to, during, and after surgery that corresponds to a view or views of the patient. The computer/display 192 can receive and integrate information collected by the operating-room equipment, display such information for use during the surgery, and facilitate articulation of the patient via manipulation of the patient-positioning system 10/110 via, for example, user interaction with the patient avatar 194. To facilitate such articulation, the computer-control and data-integration system 190 can fuse data inputted thereinto, feedback received from operation of the patient-positioning system 10/110, and data from the manufacturer/developer to limit articulation of the patient to prevent injury, afford planning of the surgery, and guide articulation of the patient prior to, during, and after surgery.

The view(s) afforded by the patient avatar 194 can correspond to a cross-section or cross-sections of the patient in the sagittal plane, the coronal plane, and/or the transverse plane. As depicted in FIG. 10, the patient avatar 194 corresponds to the cross-section of the patient P in the sagittal plane. However, the view(s) afforded by the patient avatar 194 are not limited to such traditional orthogonal views. For example, the patient avatar 194 can include a view or views that are oblique to the traditional orthogonal views. These oblique view(s) can be specific to and optimized for each patient, and can correspond to actual physical characteristics of that patient. Furthermore, as discussed below, the patient avatar 194 can be used to model and control movement of the patient prior to, during, and after surgery.

Information regarding the patient's characteristics and condition can be inputted into the computer-control and data-integration system 190 to model movement of the patient for the patient avatar 194. For example, such information can be gathered in a pre-operative patient evaluation, and can include physical characteristics of the patient such as patient anatomical dimensions, patient body weight, patient body mass, weight of different portions of the patient's body, and mass of different portions of the patient's body, as well as biomechanical limitations of the patient's anatomical kinematics to inform the patient avatar 194. Additional information regarding implants that have previously been used and/or information regarding surgical componentry including implants and instrumentation that will be used can also be inputted to model movement of the patient for the patient avatar 194. As such, the patient avatar 194 can be a virtual model (or twin) of the patient that can be adjusted to reflect the patient's characteristics and condition, and the implants and instrumentation that have or will be used. During use thereof, the patient avatar 194 can simulate movement of all or portions of the patient's body, and display probabilistic measures to predict possible surgical outcomes. For example, the patient avatar 194 can be used to simulate all or portions of the patient's spine, and in doing so, predict a simulated instantaneous axis of rotation in the patient's spine and how that simulated instantaneous axis of rotation is affected by different surgeries. Also, by simulating such movement, the limits of articulation of the patient's body can be determined, and such limits can be used by the computer-control and data-integration system 190 to constrain operation of the patient-positioning system 10/110 to prevent injury to the patient.

Beside simulating movement of the patient's body, the avatar 194 can be used to interact with the computer-control and data-integration system 190 and visualize how positions and orientations of portions of the patient-positioning system 190 can be adjusted to articulate the patient in view of the model of the patient's characteristics and condition and the use of the implants and instrumentation. By taking the patient's characteristics and condition, and the use of the implants and instrumentation into account, the computer-control and data-integration system 190 can visualize via use of the patient avatar 194 how portions of the patient-positioning system 10/110 can be adjusted to correspondingly articulate the position and orientations of the patient's body to provide access to different portions thereof for surgeries. In doing so, the patient avatar 194 can show the limits of such articulation in view of the patient's characteristics and condition, use of the implants and instrumentation, and articulation of the patient-positioning system 190 to provide a desired surgical result. Then, the surgery can be planned using the avatar 194 and according to the desired access to the patient's body.

During surgery, the patient avatar 194 can also be used to control movement of the patient using the patient-positioning system 10/110. In doing so, the patient avatar 194 can visualize in real-time the position and orientation of the patient, determine, for example, the instantaneous axis of rotation in the patient's spine, and/or visualize potential positions and orientations of the patient afforded by the patient-positioning system 10/110 (in view of the limits of the articulation in view of the patient's characteristics and condition, and the use of the implants and instrumentation). Articulation of the patient using the patient-positioning system 10/110 can then be controlled via interaction with patient avatar 194. In doing so, the computer-control and data-integration system 190 can fuse predictive virtual data and physical feedback to afford articulation of the patient using the patient avatar 194. The computer/display 192 can include a touch screen, a touch pad, mouse, keyboard, and/or other input device the affords the user interaction with the patient avatar 194. The user interaction can articulate the patient avatar 194 on the computer/display 192 into various desired positions and orientations. Thereafter, the patient-positioning system 10/110 can be manipulated under control of the computer-control and data-integration system 190 to articulate the patient in a similar or substantially similar manner to that of the patient avatar 194. Accordingly, such interaction with the patient avatar 194 allows the patient to be moved in ways that afford access to different portions of the patient's body.

Additionally, sensor(s) such as imaging device(s) can be used to determine the position and orientation of the patient relative to the patient-positioning system 10/110, and information from these sensor(s) can provide the physical feedback to the computer-control and data-integration system 190 to adjust the patient avatar 194 to correspond to the patient's actual position. Additional sensor(s) such as stress sensor(s) can be provided on the patient, and on patient-contacting portions and in actuators of the patient-positioning system 10/110 to also provide such physical feedback and determine, via evaluation of the patient's characteristics and condition by the computer-control and data-integration system 190 in view of the stress applied thereto, if undue stress is being applied to the patient. As such, information from these sensor(s) can provide feedback the computer-control and data-integration system 190 so that manipulation of the patient-positioning system 10/110 can be constrained or deactivated to prevent injury to the patient.

The computer-control and data-integration system 190 can incorporate artificial intelligence (AI) and machine-learning to better simulate and control movement the patient prior to, during, and after surgery. The AI can be used in the virtual model embodied in the patient avatar 194 to predict movement of the patient for the simulation, and, once real-time outcomes are known for the actual movement of the patient using the patient-positioning system 10/110, the machine-learning can be used to better predict such movement and control the patient-positioning system 10/110 accordingly.

As discussed below, the surgical robot(s), the navigation system(s), the radiographic imaging device(s), and other operating room equipment also can be interconnected with the computer-control and data-integration system 190, and potentially controlled thereby. Then, the positions and orientations of the operating-room equipment can be adjusted to correspondingly articulate the positions and orientations thereof and of the patient to enable a particular surgery and as the particular surgery progresses to facilitate performance thereof. For example, the computer-control and data-integration system 190 can position and reposition the patient-positioning system 10/110, the surgical robot(s), the navigation system(s), and/or the radiographic imaging device(s) can positioned and repositioned relative one another and to the patient in a synchronized or independent fashion. The movement can be controlled by the AI incorporated into the computer-control and data-integration system 190 to, for example, ideally position and orient the operating-room equipment and insure the safety of patient. As with use of the avatar, machine learning can be used with the AI to continually improve use of the operating-room equipment.

III. Maintaining Sterility when Using Patient-Positioning System.

Some of the componentry of the patient-positioning system may move in and out of sterile field during use thereof. For example, when the primary and ancillary supports are moved into and out of position to provide access to critical areas of the patient, portions of the various armatures, the one or more posts, and the primary and ancillary supports may move below the waist of the surgeon in and out of the sterile field. To sterilize the componentry that enters or re-enters the sterile field, sprayers and/or directed radiation can be utilized to sterilize such componentry. For example, the sprayers can be used to spray chemical sterilants onto the componentry, and/or the componentry can be exposed to the directed radiation to facilitate sterilization thereof.

Specially-configured layers of surgical draping also can be used to maintain the sterile field around the patient, and can be sprayed with the chemical sterilants and/or exposed to the directed radiation. Such specially-configured layers of surgical draping can be used to surround and encompass portions of the patient-positioning system, and the componentry of the patient-positioning system can be adjusted under the specially-configured layers of surgical draping that are sterile to maintain sterility during such adjustment. For example, various layers of the specially-configured layers of surgical draping also can be peeled away from some or all of the componentry as the componentry is moved in and out of the sterile field. Such specially-configured surgical draping also can be vacuum-sealed around some or all of componentry and/or portions of the patient's body, and can include insulation for maintaining the body temperature of the patient prior to, during, and after surgery.

Diverticula may be present in the draping that allow for robotic arms, appendages, and/or other tools and equipment to enter and exit the diverticula for holding the torso, the pelvis, or other body parts of the patient to facilitate at times exposure of areas of body for surgical approach and at other times for use as a supporting, restraining, or clamping member or members.

For example, use of the draping affords use of the robotic arms, appendages, and/or other tools and equipment for support functions when the patient is in a prone position and the legs, the Iliac crest, and the chest are supported thereby, and also use thereof for placing implants, moving parts of the patient's spine, and/or manipulating the patient's body when the patient is rotated from the prone position to other positions. Likewise, the use of the draping affords use of the robotic arms, the appendages, and/or the other tools and equipment when the patient is similarly supported in a right lateral, a left lateral, and/or supine position. And the use of the draping affords use of the robotic arms, the appendages, and/or the other tools and equipment for placing implants, moving parts of the patient's spine, and/or manipulating the patient's body when the patient is rotated in other positions. If necessary, the robotic arms, appendages, and/or other tools and equipment can move into and out of the same or different portions of the draping to perform same or different functions. Furthermore, the robotic arms, appendages, and/or other tools and equipment that move into and out of the draping via the diverticula are not necessarily attached to portions of the patient-positioning system, and can instead be positioned independently on the floor, the ceiling, and/or the walls of the operating room, be suspended from a platform or platforms, held by other robotic arm or arms, and/or held by a surgeon or surgeons.

Features that could be used or modified for use with the specially-configured draping and the patient-positioning system can include those of draping disclosed in U.S. Pat. Nos. 11,051,899 and 11,432,903, and U.S. Ser. Nos. 15/923,883, 15/923,944, and 17/308,319, which are hereby incorporated by reference herein.

Additionally, the sterility of the different surgical pathways and areas surrounding the different surgical pathways can be maintained via use of the patient-positioning system. As discussed above, the patient-positioning system can afford simultaneous access to portions of the patient through the different surgical pathways. During use of the patient-positioning system, the different surgical pathways and areas therearound can be maintained within the sterile field and/or sterilized if moved out of and back into the sterile field.

IV. Navigation and Radiographic Imaging Using Patient-Positioning System.

The articulation of the patient using the patient-positioning system can also be used to improve outcomes when using the navigation system(s) and/or the radiographic imaging device(s). For example, the navigation system(s) and the radiographic imaging device(s) can employ various cameras and imagers. Furthermore, if using imaging such as fluoroscopy, for example, the componentry of the patient-positioning system can be made from radiolucent materials to improve images generated thereby. During use of the cameras and imagers, the patient can be articulated by the patient-positioning system relative to the cameras and the imagers to facilitate imaging of a desired portion or portions of the patient's body. The cameras and images also can be moveable relative to the patient-positioning system and the patient to also facilitate imaging of the desired portion or portions of the patient's body. Thus, whether using the articulation of the patient by the patient-positioning system, movement of the camera and imagers, or both, the desired portions or portions of the patient's body can be accessed and imaged. Moreover, the adjustment of the patient-positioning system (and corresponding articulation of the patient) can be coordinated with the movement of the cameras and imagers to provide ideal or close to ideal placement thereof relative to the patient. As discussed above, the controls of the navigation system(s) and/or the radiographic imaging device(s) can be integrated with the computer-control and data-integration system to further improve outcomes, and facilitate the synchronized or independent movement of the patient-positioning system and the cameras and imagers.

The adjustment of the patient-positioning system also can aid the maintenance of the sterile field. By adjusting the patient-positioning system (and correspondingly articulating the patient) relative to the cameras and imagers, the camera and imagers can remain in the sterile field. For example, rather than rotating the cameras and imagers around the patient to access the desired portion or portions of the patient's body, the patient can be rotated using the patient-positioning system. As such, if the cameras and images are located above the patient, the cameras and imagers can remain in the sterile field during articulation of the patient.

V. Use of Manifold With Patient-Positioning System.

The patient-positioning system can be used in conjunction with a manifold portion that can be incorporated in or separate from the patient-positioning system that is used to interconnect lines, tubes, and wires extending to the patient with lines, tubes, and wires extending to respective equipment and surgical apparatus. For example, the lines, tubes, and wires can include one or more cardiorespiratory monitor (CRM) lines, intravenous (IV) lines, peripherally inserted central catheter (PICC) lines, somatosensory evoked potential (SEP) lines, endotracheal (ET) tubes, Foley catheters, and other lines, tubes, and wires used to facilitate surgery. The manifold portion can serve as a collection point to where the lines, tubes, and wires extending to the patient are interconnected with lines, tubes, and wires are extending to the respective equipment and the surgical apparatus that allows the patient's body to be articulated by the patient-positioning system with limited interference from the lines, tubes, and wires.

VI. Surgical Methods for Use with Patient-Positioning System.

1. Global and Localized Articulation Combined With Simultaneous Access.

The patient-positioning system can afford "global" or "regional" articulation of the patient's spine in the above-referenced planes, and various implants and instrumentation and the manipulation, implantation, and stabilization thereof can afford "localized" articulation of a portion of the patient's spine. To illustrate, the patient-positioning system can be used in generally articulating an area of the patient's spine via global or regional articulation, where regional articulation provides more finely-tuned articulation of that area than global articulation. And the patient-positioning system and/or the implants and instrumentation can be used in specifically articulating that area of the patient's spine via localized articulation. In some instances, for example, global, regional, and local articulation can be used to facilitate distraction of adjacent vertebral bodies. As such, the patient-positioning system itself serves as a surgical instrument for manipulating the patient's spine.

The patient-positioning system of the present disclosure also can afford use of a surgical method relying on simultaneous access to portions of a patient's spine. To illustrate, such simultaneous access afforded by use of the patient-positioning system can afford two or more surgical pathways to the patient's spine that are accessible simultaneously. For example, a posterior surgical pathway can be via a posterior incision or incisions in the patient's body, and a lateral surgical pathway can be via a lateral incision or incisions in the patient's body. Using such simultaneous access, the instrumentation at each of the incisions (such as, for example, elevators, retractors, spreaders, etc.) can remain in place as each of the surgical pathways are utilized.

Conventional surgeries employing two different surgical pathways typically require positioning of the patient in a first position and placement of a first set of instrumentation to gain access to a surgical pathway via a first incision or incisions, and then require removal of the first set of instrumentation and closure of the first incision or incision, before positioning of the patient in a second position and placement of a second set of instrumentation to gain access to a surgical pathway via a second incision or incisions. Unlike such conventional surgeries, the surgeon(s) and/or the surgical robot(s) can use both of surgical pathways simultaneously or in back-and-forth manner without having to remove the instrumentation at the first incision or incisions to gain access to the second incision or incisions, or vice versa. As such, surgical work-flows performed by the surgeon(s) and/or the surgical robot(s) at each of the first incision or incision(s) and the second incision or incision(s) can occur in parallel via the simultaneous manipulation of the patient's spine via these different incisions and corresponding different surgical pathways. To illustrate, the simultaneous use of different surgical work-flows allow the surgeon(s) and/or the surgical robot(s) to work in parallel to one another to facilitate simultaneous manipulation of, for example, the patient's spine at different locations to improve the overall surgical result at one or both of the different locations. In certain surgeries, the parallel surgical work-flows via different surgical pathways can facilitate simultaneous manipulation of all three columns of the patient's spine, i.e., an anterior column, a middle column, and a posterior column as described by Dr. Francis Denis. Specifically, for example, use of the parallel surgical work-flows can protect a bone screw interface, prevent subsidence of interbody implants through vertebral endplates, and/or minimize pseudoarthrosis by maintaining anatomical structural integrity.

During use of the patient-positioning system, a level or levels of the patient's spine can be simultaneously accessed from two different surgical pathways such as, for example, a posterior surgical pathway and a lateral surgical pathway. Such simultaneous access can facilitate simultaneous manipulation, implantation, and/or stabilization of the patient's spine via use of various implants and/or instrumentation relative thereto. As such, the patient-positioning system can be used to facilitate simultaneous access and corresponding simultaneous manipulation of the patient's spine, and surgical work-flows, as described below, can occur in parallel via the different surgical pathways. Furthermore, such parallel surgical work-flows can rely on use of the global and regional articulation afforded by the patient-positioning system and with specially-configured implants and instrumentation use for localized articulation. For example, sets of distraction-aiding posts, sets of lordotic rods, interbody spinal implants, distractors, and/or tension bands can be used in a surgical method relying on simultaneous access, simultaneous manipulation, and/or parallel surgical work-flows.

As discussed below, the sets of distraction-aiding posts can be, for example, screw and/or nails that can be inserted through pedicles and into vertebral bodies from a posterior first surgical pathway. The distraction-aiding posts can be headless or include heads that can be countersunk, so that portions thereof have zero or limited protrusion above the lamina of the pedicles to provide a "zero profile." The distraction-aiding posts can be used in facilitating distraction between the vertebral bodies of adjacent vertebrae, especially where bone of the vertebrae has been weakened. The lordotic rods can be attached to and extend between the distraction-aiding posts placed in the pedicles of adjacent vertebrae. The lordotic rods can be used to stabilize the adjacent vertebrae, and serve as a "track" that controls and limits the degree of distraction between vertebral bodies of the adjacent vertebrae. As discussed below, insertion of the interbody spinal implant can benefit from the distraction afforded by the use of the distraction-aiding posts and the lordotic rods, and also provide a lattice through which additional screws, or rods can be inserted to aid spinal stabilization.

For example, when using the simultaneous access afforded by use of the patient-positioning system and the specially-configured implants and instrumentation, a first incision or incisions can be formed in a posterior portion or portions of the patient's body to afford posterior access to the patient's lumbar spine via a posterior first surgical pathway, and a second incision or incisions can be formed in a lateral portion or portions of the patient's body to afford lateral and/or anterior access to the patient's lumbar spine via a lateral second surgical pathway. The posterior first surgical pathway can allow for implantation of the distraction-aiding posts and the lordotic rods, and the lateral second surgical pathway can allow for lateral and/or anterior implantation of the interbody spinal implant. As discussed below, the distraction-aiding posts also can be used in various different manners.

2. Use of Surgical Componentry Including Distraction-Aiding Posts and Lordotic Rods to Facilitate Distraction.

As depicted in FIG. 11, a level of the patient's spine can be treated to facilitate insertion of the interbody spinal implant into a disc space D between an upper vertebral body $V_1$ and a lower vertebral body $V_2$ using a first pair of distraction-aiding posts 200A and 200B and a second pair of distraction-aiding posts 204A and 204B. The first pair of distraction-aiding posts 200A and 200B can be inserted through each pedicle of an upper vertebrae on either side of a spinous process thereof (with element number 200B being in parenthesis in FIG. 11 signifying it is behind post 200A), and distal end portions 202A and 202B of the first pair of the distraction-aiding posts 200A and 200B can be inserted to impinge on or extend into portions of the corresponding vertebral-body endplate from an underside thereof. And, the second pair of distraction-aiding posts 204A and 204B can be inserted through each pedicle of a lower vertebrae on either side of a spinous process thereof (with element number 204B being in parenthesis in FIG. 11 signifying it is behind post 204A), and distal end portions 206A and 206B of the of the second pair of the distraction-aiding posts 204A and 204B can be inserted to impinge on or extend into portions of the corresponding vertebral-body endplate from an underside thereof. The distraction-aiding posts 200A, 200B, 204A, and 204B can each provide a solid construct, especially where the bone of the vertebrae has been weakened, to facilitate distraction. Furthermore, the distraction-aiding posts 200A, 200B, 204A, and 204B can include proximal end portions 210A, 210B, 212A, and 212B, respectively, and these end portions can be manipulated to facilitate distraction of the upper vertebral body $V_1$ and the lower vertebral body $V_2$.

As depicted in FIGS. 11 and 12, the first lordotic rod 220 can be positioned relative to proximal end portions 210A and 212A of the distraction-aiding posts 200A and 204A, respectively, on a first side of the spinous processes, and a second lordotic rod 222 (with element number 222 being in parenthesis in FIG. 11 signifying it is behind rod 220) can be positioned relative to proximal end portions 210B and 212B of the distraction-aiding posts 200B and 204B, respectively, on a second side of the spinous processes. Each of the first lordotic rod 220 and the second lordotic rod 222 can include upper and lower slots or apertures for facilitating engagement with the proximal end portions 210A, 2106, 212A, or 212B. For example, upper portions of the first lordotic rod 220 and the second lordotic rod 222 can include slots for facilitating engagement with the end portions 210A and 2106, respectively, and lower portions of the first lordotic rod 220 and the second lordotic rod 222 can include apertures for facilitating engagement with the end portions 212A and 212B, respectively. Lengths and curvatures of the first lordotic rod 220 and the second lordotic rod 222, and shapes of the slots formed in the first lordotic rod 220 and the second lordotic rod 222 can be varied and specially configured according to the dimensions of the patient, and the type of surgery being performed on thereon.

The proximal end portions 210A, 210B, 212A, and 212B, as depicted in FIGS. 11 and 12, can be mechanically-fastened relative to the respective one of the first lordotic rod 220 and the second lordotic rod 222 using a post-rod interconnection of mechanical fasteners and the slots or the apertures. The lengths and curvatures of the first lordotic rod 220 and the second lordotic rod 222, and the shapes of the slots formed in the first lordotic rod 220 and the second lordotic rod 222 serve in constraining the distraction of the upper vertebral body $V_1$ and the lower vertebral body $V_2$ to the desired degree of lordosis. In doing so, the distal end portions 210A and 210B can slide within the slots formed in and along the lengths and curvatures of the of the first lordotic rod 220 and the second lordotic rod 222 following the tracks defined thereby.

After affixation of the first lordotic rod 220 and the second lordotic rod 222, the interbody spinal implant 224 can be inserted via the second lateral surgical pathway into the disc space between the upper vertebral body $V_1$ and the lower vertebral body $V_2$. The distraction-aiding posts 200A, 200B, 204A, and 204B, and the interbody spinal implant 224 can be used in distracting the upper vertebral body $V_1$ and the lower vertebral body $V_2$ apart from one another. Furthermore, the first lordotic rod 220 and the second lordotic rod 222 can be used in controlling and limiting the degree of distraction between the vertebral body $V_1$ and the lower vertebral body $V_2$. The constraints of the lengths and curvatures of the first lordotic rod 220 and the second lordotic rod 222, and the shapes of the slots of the first lordotic rod 220 and the second lordotic rod 222 guide the distraction of the upper vertebral body $V_1$ and the lower vertebral body $V_2$. And the play afforded by the loose attachment of the end portions 210A and 210B to the first lordotic rod 220 and the second lordotic rod 222 allows the interbody spinal implant 224 to be worked into the disc space until such play is limited or ceases at the desired degree of lordosis between the upper vertebral body $V_1$ and the lower vertebral body $V_2$.

Thereafter, the end portions 210A and 2108 can be fixedly attached to the first lordotic rod 220 and the second lordotic rod 222 to stabilize the upper vertebral body $V_1$ and the lower vertebral body $V_2$ and maintain the desired degree of lordosis therebetween.

As such, the interbody spinal implant 224 and the interaction of the distraction-aiding posts 200A, 200B, 204A, and 204B with the first lordotic rod 220 and the second lordotic rod 222 can work together to create an ideal degree of lordosis through such distraction. Furthermore, stress points applied between the patient's spine and the interbody spinal implant 224 and via the interaction of the distraction-aiding posts 200A, 200B, 204A, and 204B with the first lordotic rod 220 and the second lordotic rod 222 can be shared during use thereof. Correspondingly, forces applied between the patient's spine and each individual component, whether implant or instrumentation, is correspondingly reduced.

Furthermore, the access afforded by the posterior first surgical pathway and the lateral second surgical pathway, and use of the patient-positioning system also allows the distraction-aiding posts 200A, 200B, 204A, and 204B and the interbody spinal implant 224 to be manipulated simultaneously or in back-and-forth manner to facilitate insertion the interbody spinal implant 224 into the disc space D. For example, the proximal end portions 210A, 210B, 212A, and 212B can be manipulated from the posterior first surgical pathway, and simultaneously, the interbody spinal implant 224 can be manipulated from the lateral second surgical pathway to facilitate distraction of the upper vertebral body $V_1$ and the lower vertebral body $V_2$ to position the interbody spinal implant 224 in the disc space D.

The surgical method using the sets of distraction-aiding posts, sets of lordotic rods, and interbody spinal implants can be repeated for additional levels of the spine above and/or below the first level treated with additional and/or longer lordotic rods. The lordotic posts also can serve in stabilizing the treated level of the patient's spine, so that the surgeon(s) and/or the surgical robot(s) can operate to loosen sclerotic tissues adjacent thereto. After positioning of the interbody spinal implant 224 is complete, the distraction-aiding posts and/or the lordotic rods can remain in position or be removed from the patient's body.

3. Use of Surgical Componentry Including Distractors and Tension Bands with Distraction-Aiding Posts to Facilitate Distraction.

Figure 13:
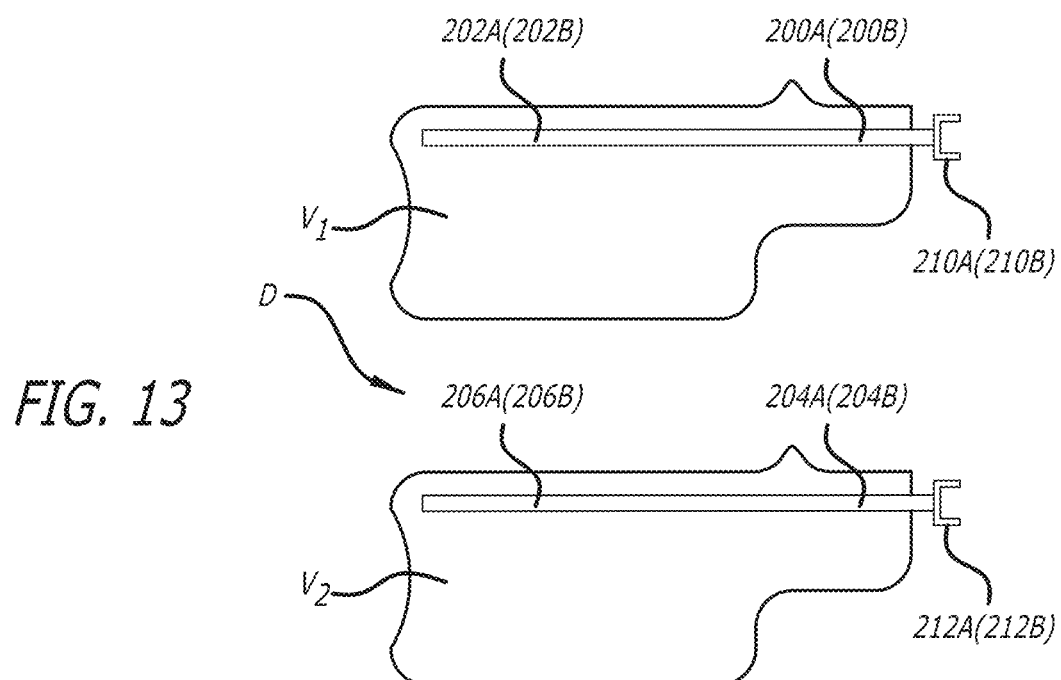
FIG. 13 is a lateral representational view of a level of a human spine being treated using a second embodiment of a first distraction-aiding post inserted into an upper vertebral body and a second distraction-aiding post inserted into a lower vertebral body.
Figure 14:
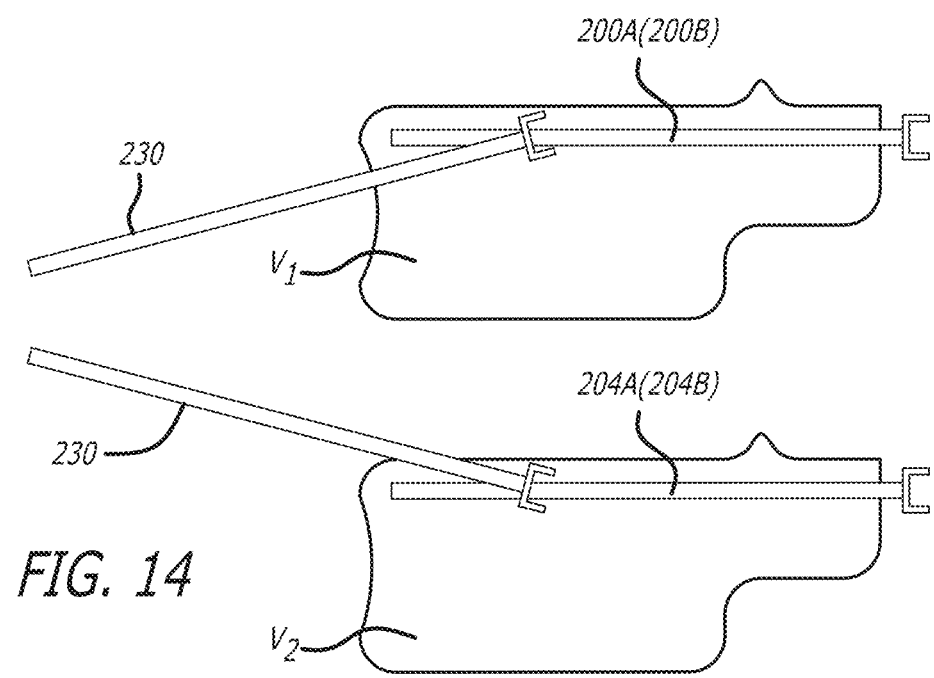
FIG. 14 is a lateral representational view, similar to FIG. 13, depicting the second embodiment of the first distraction-aiding post and the second distraction-aiding post respectively engaged by a first embodiment of distractors.
Figure 16:
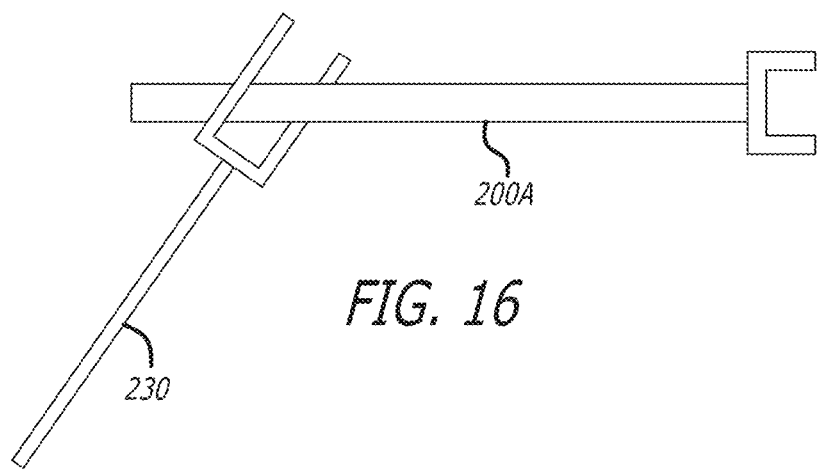
FIG. 16 is a side view depicting engagement of the first embodiment of the distractor of FIGS. 14 and 15 engaged to the second embodiment of the distraction-aiding post of FIG. 13.
Figure 17:
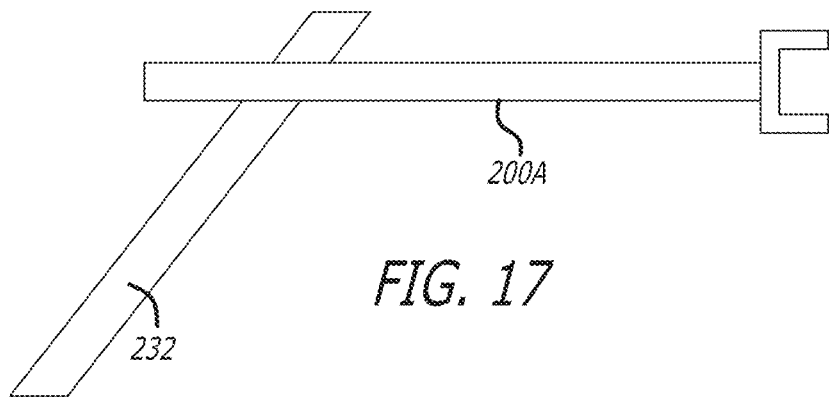
FIG. 17 is a side view depicting engagement of a second embodiment of a distractor engaged to the second embodiment of the distraction-aiding post of FIG. 13
Figure 18:
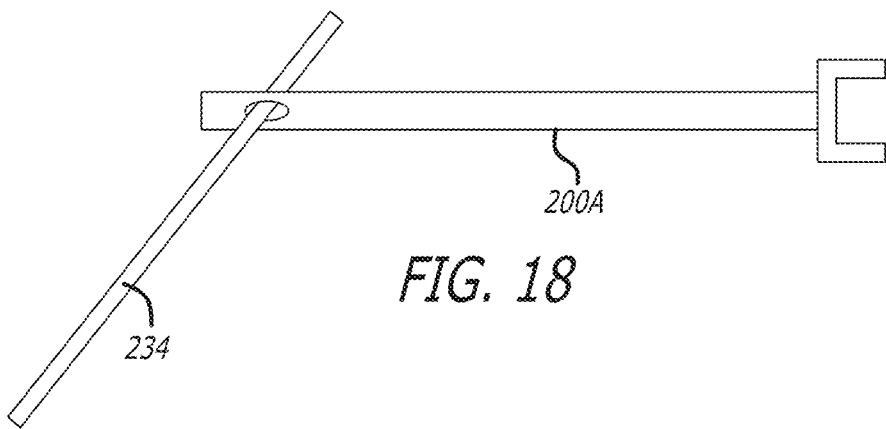
FIG. 18 is a side view depicting engagement of a third embodiment of a distractor engaged to the second embodiment of the distraction-aiding post of FIG. 13.

The distraction-aiding posts 200A, 200B, 204A, and 204B can also be used with one or more distractors 230, 232, and 234 (FIGS. 16-18) to distract the upper vertebral body $V_1$ and the lower vertebral body $V_2$ apart from one another to facilitate insertion of the interbody spinal implant into the disc space D. For example, as depicted in FIG. 13, the first pair of distraction-aiding posts 200A and 200B and the second pair of distraction-aiding posts 204A and 204B can be inserted in similar fashion to that described above. The distraction-aiding posts 200A, 200B, 204A, and 204B can include the end portions 210A, 210B, 212A, and 212B of FIGS. 11 and 12, or can be modified (FIGS. 13-15) to include U-shaped or hook portions facilitating attachment of one or more tension bands 240. Furthermore, the distractors 230 (FIGS. 14 and 15), 232, and/or 234 can be used to engage the distraction-aiding posts 200A, 2008, 204A, and 204B via the lateral second surgical pathway to distract the upper vertebral body $V_1$ and the lower vertebral body $V_2$ apart from one another. The distractors 230, 232, and 234 can be instruments with distal end portions configured to engage the distraction-aiding posts 200A, 200B, 204A, and 204B. For example, as depicted in FIGS. 16-18, the distal end portions can include a U-shaped portion on the distractor 230, a flattened edge on the distractor 232, or be sized as with distractor 234 for receipt through apertures formed in the distraction-aiding posts 200A, 200B, 204A, and 204B. After such engagement, the distractors 230, 232, and/or 234 can be manipulated to push against the distraction-aiding posts 200A, 200B, 204A, and 204B, and correspondingly distract the upper vertebral body $V_1$ and the lower vertebral body $V_2$ anteriorly to increase lordosis and facilitate insertion of an interbody spinal implant. To aid such distraction, proximal ends of the distractors 230, 232, and 234 can be engaged to an expander configured to apply force therethrough to the distraction-aiding posts 200A, 200B, 204A, and 204B. If necessary, the distractors 230, 232, and 234 can perforate the upper vertebral body $V_1$ and the lower vertebral body $V_2$ to engage the distraction-aiding posts 200A, 200B, 204A, and 204B.

Figure 15:
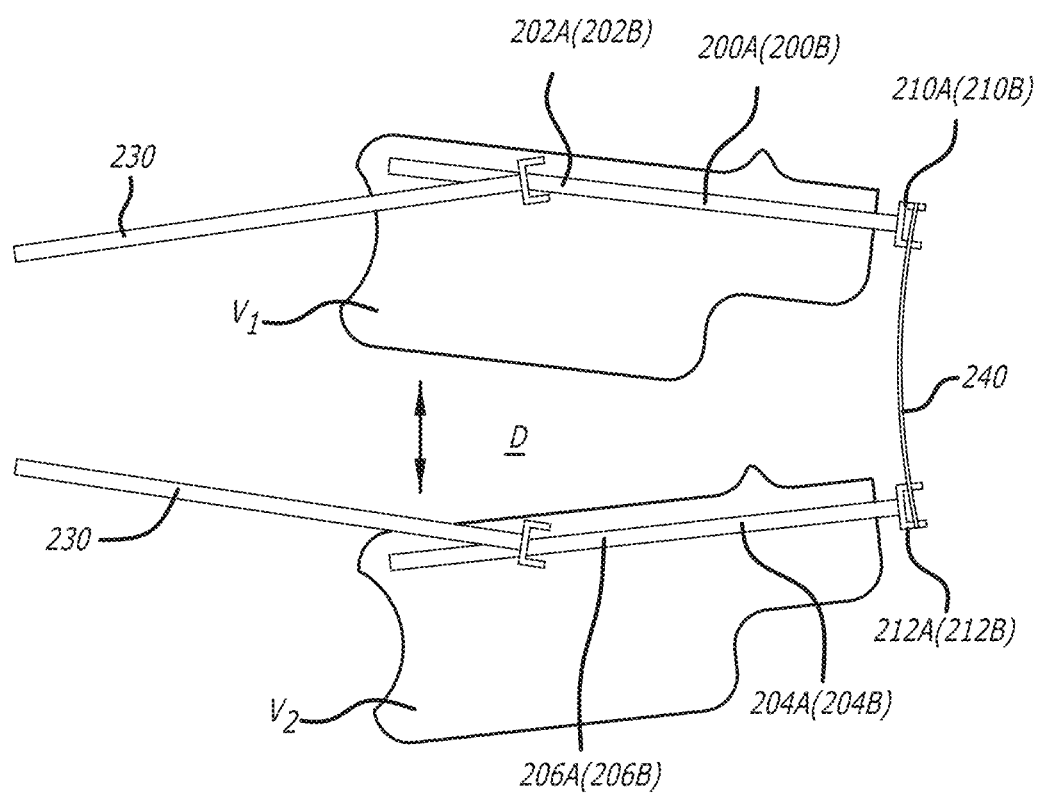
FIG. 15 is a lateral representational view, similar to FIGS. 13 and 14, depicting distraction of the upper vertebral body and the lower vertebral body relative to one another via engagement of the distractors against the second embodiment of the first distraction-aiding post and the second distraction-aiding post, and use of a tension band to aid the distraction.

Additionally, as depicted in FIG. 15, the tension bands 240 can be used with or without the distractors 230, 232, and/or 234 to facilitate distraction of the upper vertebral body $V_1$ and the lower vertebral body $V_2$. The tension bands 240 can be positioned via the posterior first surgical pathway in similar fashion to the first lordotic rod 220 and the second lordotic rod 222, and be attached between the proximal end portions 210A and 212A and between the proximal end portions 210B and 212B. The tension bands 240 be made of biologic or synthetic materials, and can be resilient such that the resiliency thereof pulls or squeezes the proximal end portions 210A and 212A and the proximal end portions 210B and 212B together. Furthermore, various tension bands 240 having different tensions can be provided, and a suitably-tensioned tension band 240 can be selected. The tension bands 240 can have a low profile relative to the pedicles of the adjacent vertebrae, and by pulling or squeezing these end portions together using the tension bands 240, the anterior distraction between the upper vertebral body $V_1$ and the lower vertebral body $V_2$ can be correspondingly increased to increase lordosis and facilitate insertion of the interbody spinal implant. The tension bands 240 can also be used in preventing parallel distraction at posterior portions of the upper vertebral body $V_1$ and the lower vertebral body $V_2$.

4. Use of Surgical Componentry Including Tension Bands with Expandable Interbody Spinal Implant.

Figure 19:
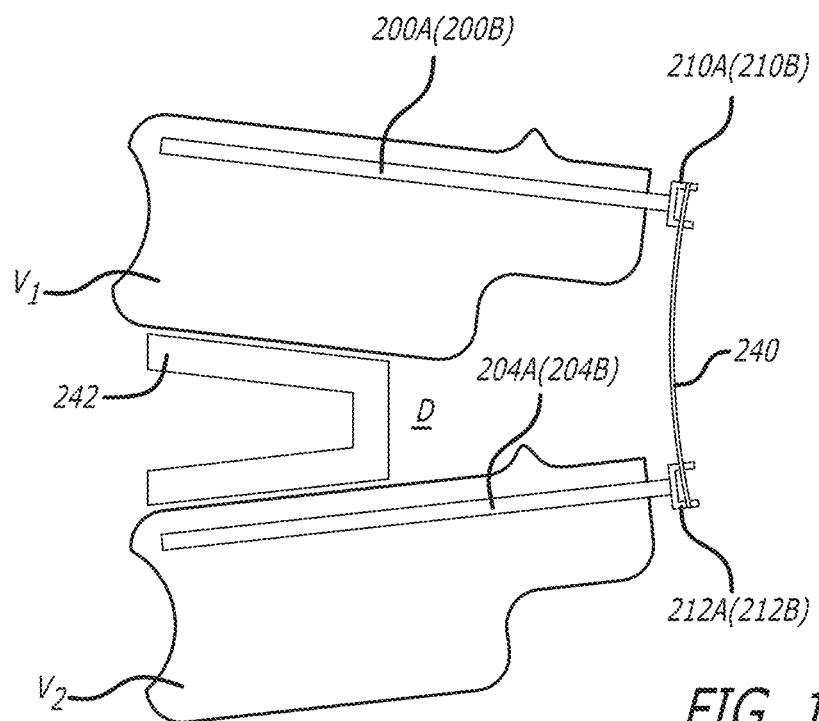
FIG. 19 is a lateral representational view, similar to FIGS. 13-15, depicting use of an expandable implant inserted between the upper vertebral body and the lower vertebral body.

The tension bands 240, as depicted in FIG. 19, can also be used in conjunction with an expandable interbody spinal implant 242 to facilitate distraction of the upper vertebral body $V_1$ and the lower vertebral body $V_2$. The expandable interbody spinal implant 242 can be inserted via the second lateral surgical pathway into the disc space between the upper vertebral body $V_1$ and the lower vertebral body $V_2$. Together with the pulling or squeezing afforded by resiliency of the tension bands 240, the expandable interbody spinal implant 242 can be used in distracting the upper vertebral body $V_1$ and the lower vertebral body $V_2$. Like the constrained guidance afforded by the sliding of the distal end portions 210A and 2108 within the slots of the first lordotic rod 220 and the second lordotic rod 222, the use of the tension bands 240 and the expandable interbody spinal implant 242 guides the distraction of the upper vertebral body $V_1$ and the lower vertebral body $V_2$. After the expansion of the expandable interbody spinal implant 242 provides the desired degree of lordosis, the expansion of the expandable interbody spinal implant 242 can be locked into position to stabilize the upper vertebral body $V_1$ and the lower vertebral body $V_2$ and maintain the desired degree of lordosis therebetween.

As discussed above, the combination of the simultaneous access afforded by use of the patient-positioning system with the specially-configured implants and instrumentation affords distraction of the upper vertebral body $V_1$ and the lower vertebral body $V_2$. However, use of the patient-positioning system also has an added benefit. As discussed above, besides affording simultaneous access, the patient-positioning system can be used for global and regional articulation of the patient. Thus, the positions and orientations of the componentry of the patient-positioning system can be adjusted to globally and regionally articulate the positions and orientations of the patient in preparation for and/or during the local articulation of the adjacent vertebral bodies, and the simultaneous access and the use of the specially-configured implants and instrumentation can be used for the local articulation to facilitate distraction of the upper vertebral body $V_1$ and the lower vertebral body $V_2$.

5. Use of Surgical Componentry Including Stabilization Plates and Interconnection Using Mechanical Fasteners.

Figure 20:
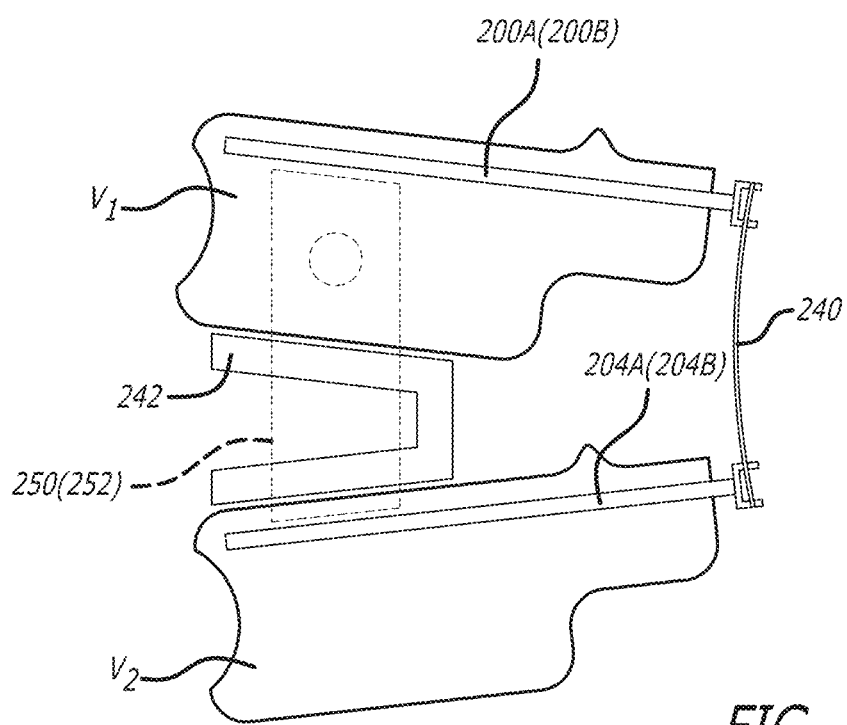
FIG. 20 is a lateral representational view, similar to FIGS. 13-15 and 19, depicting use of a plate portion extending between the second embodiment of the first distraction-aiding post and the second distraction-aiding post.

In addition to facilitating distraction of the adjacent vertebral bodies, the distraction-aiding posts 200A, 200B, 204A, and 204B can also be interconnected with one another using one or more stabilization plates to further stabilize the upper vertebral body $V_1$ and the lower vertebral body $V_2$, and maintain the desired degree of lordosis therebetween. As depicted in FIG. 20, a first stabilization plate 250 can be attached between the distracting-aiding posts 200A and 204A, and a second stabilization plate 252 (with element number 252 being in parenthesis in FIG. 20 signifying it is behind the first stabilization plate 250) can be attached between the distraction-aiding posts 200B and 204B. The first stabilization plate 250 and the second stabilization plate 252 can be used with or without use of the tension bands 240 and the expandable spinal implant 242. The first stabilization plate 250 and the second stabilization plate 252 can be inserted through portions of the upper vertebral body $V_1$ and the lower vertebral body $V_2$ to facilitate contact with the distraction-aiding posts 200A, 200B, 204A, and 204B. If the expandable interbody implant 242 remains in position, the first stabilization plate 250 can be provided on one lateral side of the expandable interbody implant 242, and the second stabilization plate 252 can be provided on the other lateral side of the expandable interbody implant 242. The first stabilization plate 250 and the second stabilization plate 252 can also be interconnected with the expandable interbody implant 242 to prevent expulsion thereof and to further stabilize the upper vertebral body $V_1$ and the lower vertebral body $V_2$.

The interbody spinal implant 224 and the expandable interbody spinal implant 242 can also be interconnected with the distraction-aiding posts 200A, 200B, 204A, and 204B using, for example, mechanical fasteners. The mechanical fasteners can be received through bony portions of the upper vertebral body $V_1$ and the lower vertebral body $V_2$, and such fastening serves to prevent expulsion of the interbody spinal implant 224 and the expandable interbody spinal implant 242, and to further stabilize the adjacent vertebral bodies. The distraction-aiding posts 200A, 200B, 204A, and 204B can also include portions that penetrate through the endplates into the disc space that can be configured to mechanically engage the interbody spinal implant 224, the expandable interbody spinal implant 242, the first stabilization plate 250, and/or the second stabilization plate 252. After positioning of the distraction-aiding posts 200A, 200B, 204A, and 204B, the interbody spinal implant 224, the expandable interbody spinal implant 242, the first stabilization plate 250, and/or the second stabilization plate 252 can be brought into engagement therewith. Such engagement also can serve prevent expulsion of the interbody spinal implant 224, the expandable interbody spinal implant 242, the first stabilization plate 250, and/or the second stabilization plate 252, and to further stabilize the adjacent vertebral bodies.

6. Use of Surgical Componentry Including Anteriorly-Inserted Posts.

Figure 21:
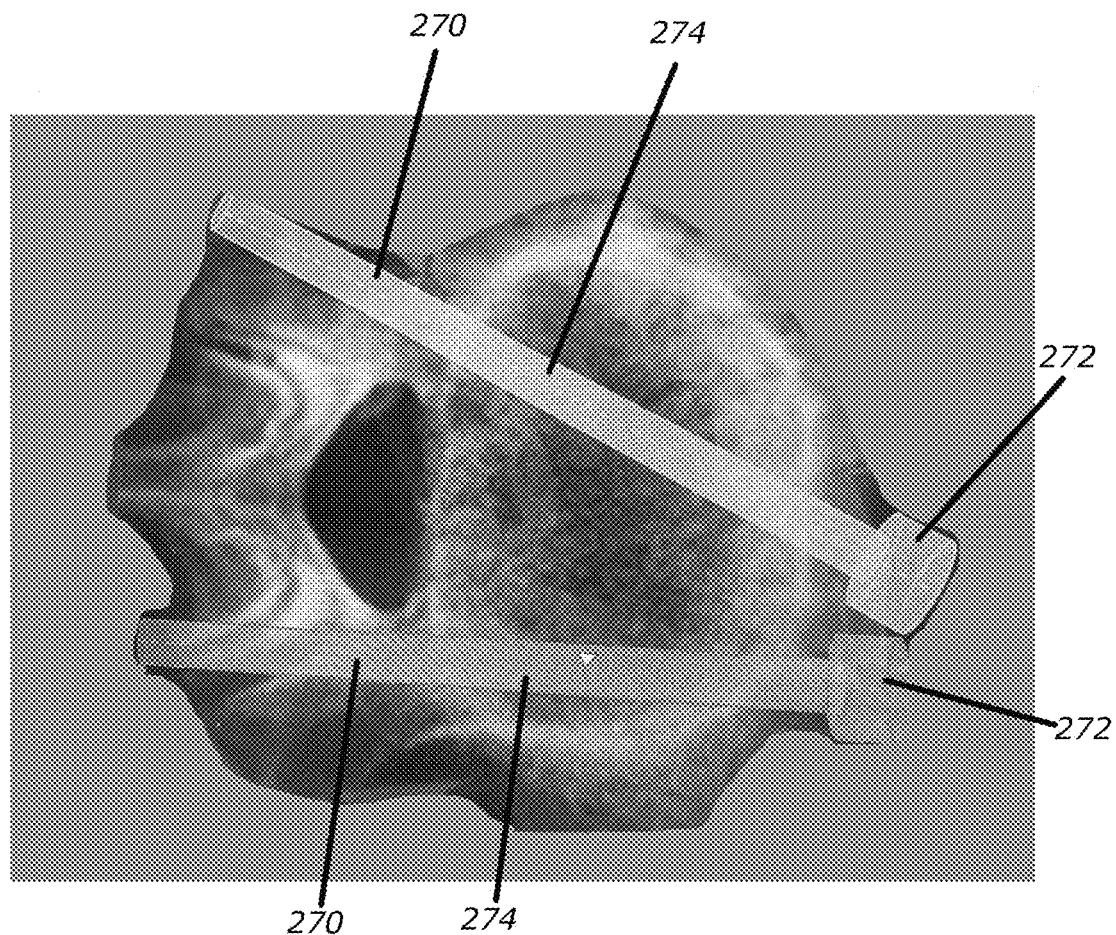
FIG. 21 is a top radiographic view of a vertebrae with a first post and a second post depicted representationally inserted from anterior direction into the vertebrae.
Figure 22:
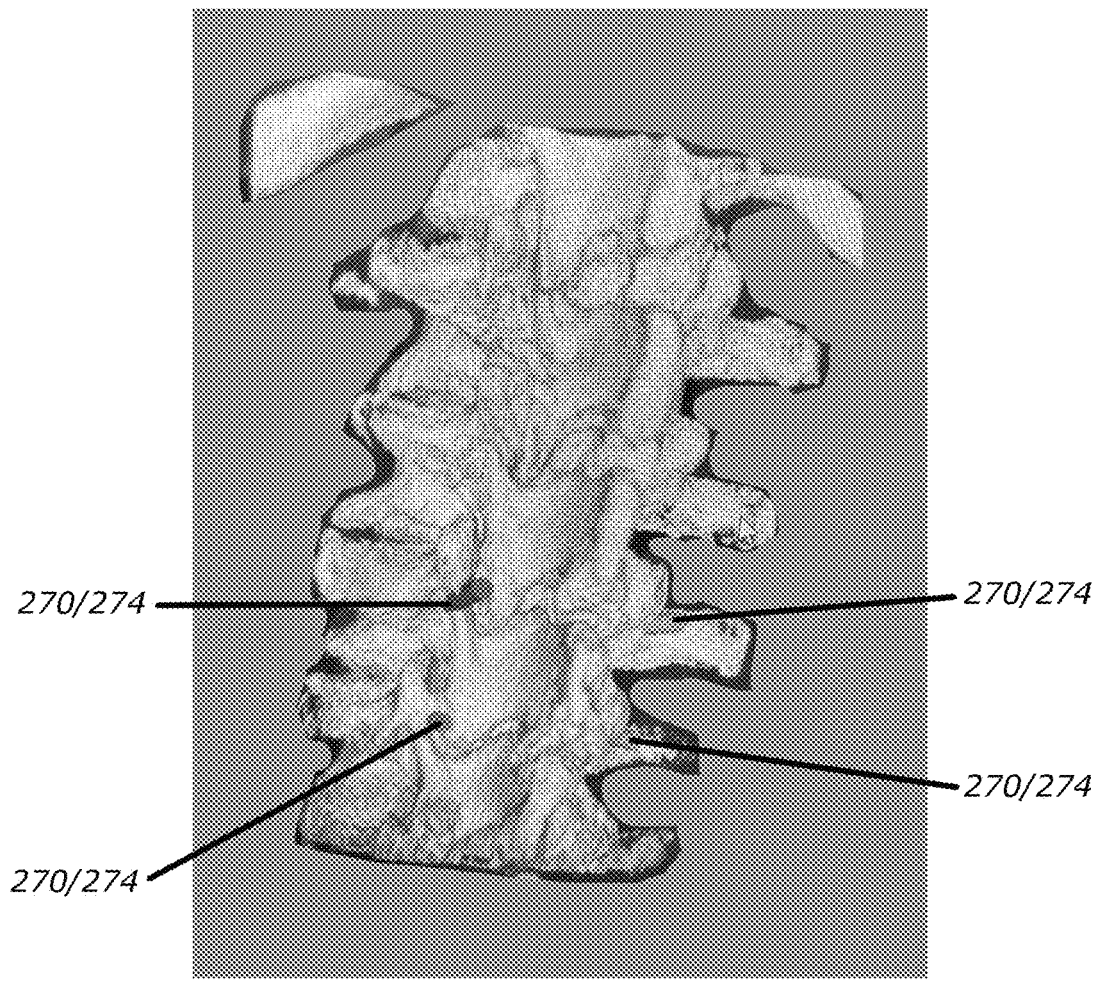
FIG. 22 is a computer-generated depiction of a posterior portion of a human spine from the sagittal plane perspective with the first post and the second post of FIG. 21 extending outwardly from pedicles of an upper vertebrae, and an additional third post and an additional fourth post extending outwardly from pedicles of a lower vertebrae.
Figure 23:
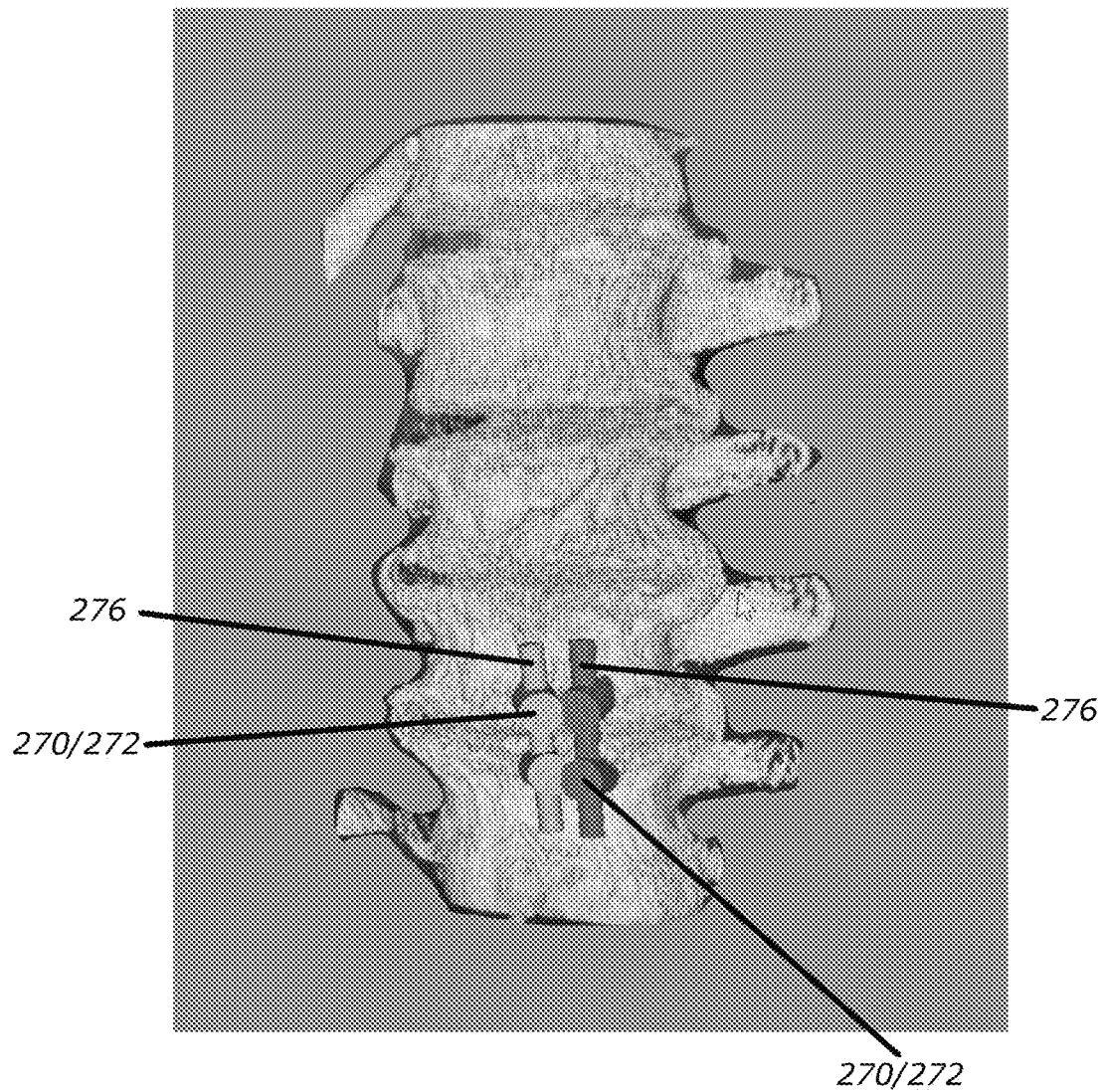
FIG. 23 is a computer-generated depiction of an anterior portion of a human spine with the first post and third post of FIG. 22 interconnected via a first rod, and the second post and the fourth post of FIG. 22 interconnected via a second rod.

As depicted in FIGS. 21-23, various posts 270 can be inserted anteriorly through portions of a vertebral body and corresponding pedicles. The posts 270 each includes a head portion 272 and a shaft portion 274 The shaft portions 274 can be inserted to impinge on or extend into portions of the hard bone of the vertebrae, and the head portions can impinge on anterior portions of the vertebral body. Like the distracting aiding posts 200A, 200B, 204A, and 204B, the posts 270 can each provide a solid construct, especially where the bone of the vertebrae has been weakened, to facilitate distraction. The shaft portions 274, as depicted in FIG. 22, also provide a "low profile" upon exiting the pedicles, and the head portions 274 can be interconnected using rods 276 extending between the head portions 274 adjacent the anterior portions of the vertebral body.

VII. Integration and Interaction of Patient-Positioning System, Computer-Control and Date-Integration System, and Other Operating-Room Equipment in Operating Room.

Figure 24:
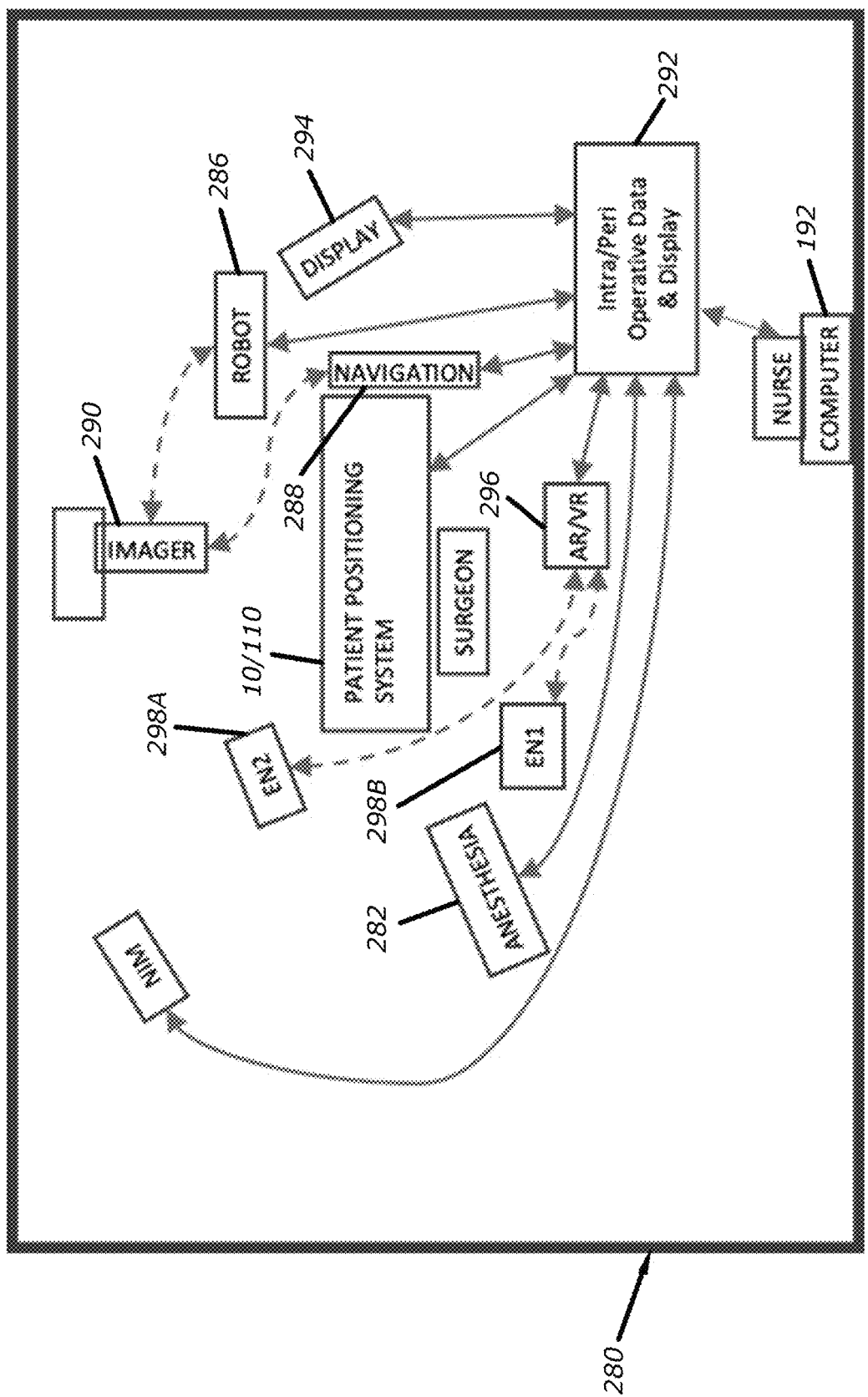
FIG. 24 is a schematic representation of an operating room used to perform surgery on a patient using a patient-positioning system and a computer-control and data-integration system according to the present disclosure.

FIG. 24 is a depiction of an operating room 280 in which the patient-positioning system (including the first embodiment 10 and the second embodiment 110) can be used with the above-discussed surgery componentry to facilitate addressing and correcting of spinal diseases of the patient including spinal deformities, degeneration, and injuries. As depicted in FIG. 24, the patient-positioning system 10/110 can be positioned in a centralized location in the operating room 280, and other enabling technologies such as operating-room equipment for performing the surgery and/or aiding in the performance of the surgery can be positioned therearound. To illustrate, the operating-room equipment can include anesthesia/respiratory equipment 282, neuro-integrity monitoring equipment 284, surgical robot(s) 286, navigation system(s) 288, and/or radiographic imaging device(s) 290 that can be positioned around the patient supported by the patient-positioning system 10/110, and be operated by surgeon(s), nurse(s), surgical assistant(s), and/or other operating-room personnel. As discussed below, the operating-room equipment can communicate interactively with one another and/or the computer-control and data-integration system 190. The above-discussed manifold can also be positioned in the operating room 280 adjacent the patient-positioning system 10/110.

The computer/display 192 of the computer-control and data-integration system 190 can also be included in the operating room 280, and can integrate information collected from the above-referenced operating-room equipment. To that end, wired or wireless connections between the computer/display 192 and the above-referenced operating-room equipment can provide a data flow transferring information to the computer-control and data-integration system 190 and/or between the operating-room equipment. The wireless connections, for example, can be via 5G/LTE, Bluetooth, and/or Wi-Fi communication. And the computer/display 192 can control operation of the above-referenced operating room equipment, perform the data integration and fusion in real-time, and transfer the information between the above-referenced operating-room equipment to afford interaction therebetween. In addition to or instead of the computer/ display 192, the computer-control and data integration system 190 can include a separate computer/display or computers/displays 292 to control operation of the above-referenced operating-room equipment, perform the data integration and fusion in real-time, and transfer the information between the above-referenced operating-room equipment to afford interaction therebetween via wired or wireless connections. The additional computer(s)/display(s) 292 can be provided inside or outside of the operating room 280, and can be used to provide additional processing power to the computer-control and data-integration system 190. Accordingly, the personnel (such as, for example, the nurse(s) under the direction of the surgeon(s)) inside and outside of the operating room 280 can use the computer/ display 192 and/or the separate computer(s)/display(s) 292 to control operation of the patient-positioning system 10/110 and articulation of the patient avatar 194, as well as control operation of the above-referenced operating room equipment.

One or more display screens 294 can be positioned in the operating room 280 to display pertinent information from the above-referenced operating-room equipment and from the computer-control and data-integration system 190. For example, like the computer/display 192 and the additional computer(s)/display(s) 292, the display screen(s) 294 can display the patient avatar 194 and the information associated therewith. Furthermore, in addition to the display screen(s) 294, augmented reality (AR), virtual reality (VR), and/or mixed reality (MR) equipment 296 are other enabling technologies that can be used by the operating-room personnel to visualize information supplied by the operating-room equipment to facilitate the surgery. The information facilitating the use of the AR/VR equipment 296 can be provided to the computer-control and data-integration system 190, and such information can also be displayed on the computer/ display 192, the additional computer(s)/displays(s) 292, and the display screens 296. Other enabling technologies referenced by 298A and 298B can be provided in the operating room 280 adjacent the patient-positioning system 10/110.

VIII. Data Flows Developed During Care Pathway, Integration of Data Flows in Care Pathway, and Interaction of Computer-Control and Data-Integration System with Operating-Equipment Using Data Flows.

Figure 25:
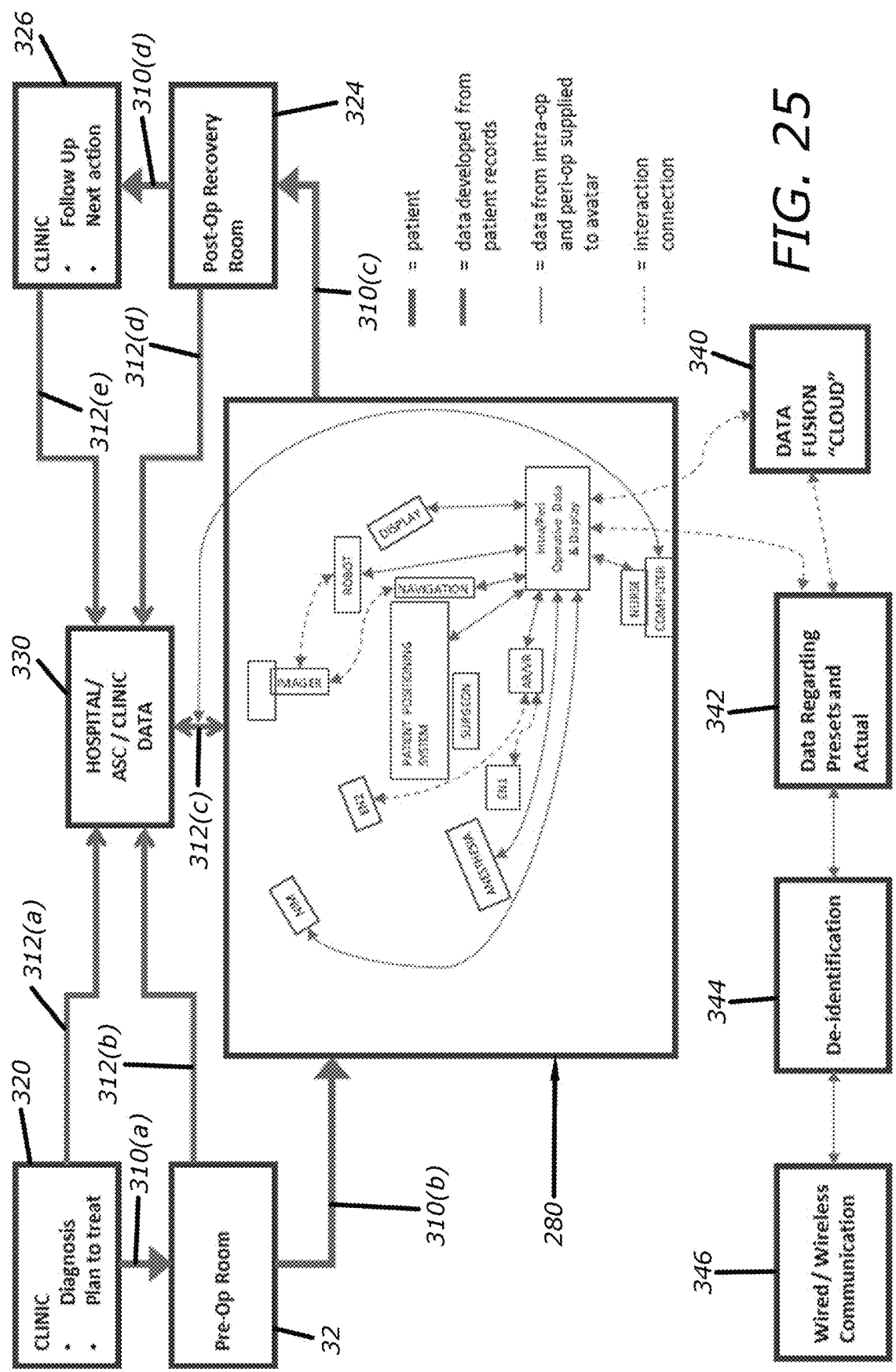
FIG. 25 is a schematic representation of care pathway(s) and data pathway(s) for used for addressing and correcting maladies of a patient incorporating the operating room of FIG. 24.

As depicted in FIG. 25, the performance of surgery on the patient in the operating room 280 is part of care pathway(s) 310 and data pathway(s) 312 for addressing and correcting maladies of the patient (including, for example, spinal deformities, degeneration, and injuries). During the care pathway(s) 310, the patient can progress from location to location to facilitate treatment of the maladies, and during the data pathway(s) 312, data can be developed regarding the patient at the locations along the care pathway(s) 310. Such data then can be transferred along the data pathway(s) 312 for ultimate integration into various parts of the care pathway(s) 310.

To illustrate, the care pathway(s) 310, as depicted in FIG. 25, can begin with box 320 representing a clinic or a doctor's office where the maladies of the patient can be diagnosed and a plan to treat the maladies is developed. One the day of the surgery, the patient will progress along care pathway 310($a$) to a pre-operative room at a hospital or an ambulatory surgery center represented by box 322 where the patient is prepared for surgery, then the patient will progress along care pathway 310($b$) to the operating room 280 at the hospital or the ambulatory surgery center for performance of the surgery, and then the patient will progress along care pathway 310($c$) to a post-operative room at the hospital or the ambulatory surgery center represented by box 324 where the patient recovers from the surgery. Thereafter, the patient will progress along care pathway 310($d$) back to the clinic or the doctor's office represented by box 326 for surgery follow-up and determination (if any) of the next steps to treat the maladies.

Data can be developed at each location during progression of the patient along the care pathway(s) 310. To illustrate, data can be developed before surgery at box 320 (such as, for example, the patient's characteristics and condition at the time of diagnosis), and that data can be transferred via a data pathway 312($a$) to a data repository at the clinic, the doctor's office, a hospital, and/or an ambulatory surgery center represented by box 330. Data can also be developed before surgery at box 322 (such as, for example, the patient's characteristics and condition at the time of surgery), and that data can be transferred via a data pathway 312($b$) to the data repository represented by box 330.

On the day of the surgery, as depicted in FIG. 25, data from the data repository represented by box 330 can be transferred along a data pathway 312($c$) to the computer-control and data-integration system 190 and the other operating-room equipment in the operating room 280. The data from the data repository represented by box 330 can be the patient's characteristics and condition including the patient anatomical dimensions, the patient body weight, the patient body mass, the weight of different portions of the patient's body, and the mass of different portions of the patient's body, as well as the biomechanical limitations of the patient's anatomical kinematics. And the data also can be additional information regarding the implants that have previously been used and/or information regarding the surgical componentry including the implants and the instrumentation that will be used. The data from the data repository represented by box 330 can facilitate creation of the virtual model of the patient that is the patient avatar 194. Additionally, data developed during surgery can be transferred via the data pathway 312($c$) to the data repository represented by box 330.

After surgery, data can be developed at the post-operative room at the hospital or the ambulatory surgery center represented by box 324 and at the clinic or the doctor's office represented by box 326, and the data can be transferred via data pathways 312($d$) and 312($e$), respectively, for use in future treatment of and/or surgery on the patient.

As discussed above, the computer/display 192 and/or the additional computer(s)/display(s) 294 can be used to control operation of the above-referenced operating room equipment, perform the data integration and fusion in real-time, and transfer the information between the above-referenced operating-room equipment to afford interaction therebetween. As depicted in FIG. 25, the computer/display 192 and/or the additional computer(s)/display(s) 294 can also communicate offsite to a cloud computer center identified by box 340 to facilitate performance of the data integration and fusion, or other operation facilitating use of the computer-control and data-integration system 190, the patient-positioning system 10/110, and the operating-room equipment. The offsite cloud computer at box 340 can provide real-time processing power to aid or supplant performance of such operations by the computer/display 192 and/or the additional computer(s)/display(s) 294, and can be connected via wired and/or wireless connections to the computer-control and data-integration system 190.

The computer-control and data-integration system 190 and/or the cloud computer can also communicate with manufacturers/developers via box 342 to receive presets for the patient-positioning system for performance of different surgeries via box 342. These presets can be used in visualizing how positions and orientations of portions of the patient-positioning system 190 can be adjusted to articulate the patient for a particular surgery. Additionally, the data developed via use of the computer-control and data-integration system 190, the patient-positioning system 10/110, and the enabling technologies can be communicated to the manufacturers/developers via box 342, so that best practices using same can be updated and refined for continued product improvement. The data communicated can also correspond to electrical and/or mechanical measurement sensor signals recorded during use of the motors, actuators, transmissions, and controllers of the patient-positioning system 10/110.

Data corresponding to the performance of different particular surgeries can be forwarded to the manufacturers//developers from different installations of the computer-control and data-integration system 190, the patient-positioning system 10/110, and/or the enabling technologies. The data communicated can be raw or in fused form after the data integration and fusion, and can describe the below-discussed work-flows and effectiveness of the below-discussed work-flows for different particular surgeries corresponding to operation of the computer-control and data-integration system 190, the patient-positioning system 10/110, and/or the enabling technologies. This data can be compared and aggregated by the manufacturers/developers, and the compared/aggregated data and corresponding analysis of the data can afford updating and refining best practices for different particular surgeries to aid use of the computer-control and data-integration system 190, the patient-positioning system 10/110, and/or the enabling technologies. The best practices can then be communicated back to the individual installations for use therein. For example, the presets from the manufacturers/developers ultimately can be synced with data developed through use of the computer-control and data-integration system 190, the patient-positioning system 10/110, and/or the enabling technologies. Furthermore, the data corresponding to the electrical and/or mechanical measurement sensor signals can also be forwarded to the manufacturers/developers, and such data can be analyzed to determine, for example, if parts of the patient-positioning system 10/110 are suffering from failure, and to schedule service/maintenance thereof and/or to evaluate for quality-control purposes.

The data corresponding to the performance of different particular surgeries that is forwarded to the manufacturers//developers from different installations of the computer-control and data-integration system 190, the patient-positioning system 10/110, and/or the enabling technologies can be manipulated to de-identify specific patients at box 344 by stripping identifying information therefrom. Furthermore, the manufacturers/developers can receive and send such data from some or all of the individual installations of the computer-control and data-integration system 190, the patient-positioning system 10/110, and the enabling technologies via wired and/or wireless connections at box 346.

IX. Care of Patient in Context of Continuous or Intermittent Needs, Care Pathways for One or More Diagnosis, Cycles of Care, Episodes of Care, Specific Diagnosis Pathways, Treatment/Therapy Pathway, and Use of Patient-Positioning System, Computer-Control and Data-Integration System, Implants and Instrumentation, and Surgical Methods.

The needs of the patient can be looked at from general to specific modalities of care, and these modalities can describe an episode for improving the patient's health. From general to specific, these modalities can include continuous or intermittent needs, care pathways for one or more diagnosis, cycles of care, episodes of care, specific diagnosis pathways, treatment/therapy pathway, and use of the computer-control and data-integration system 190, the patient-positioning system 10/110, the enabling technologies, the implants and instrumentation, and the surgical methods. As such, the computer-control and data-integration system 190, the patient-positioning system 10/110, the enabling technologies, the implants and instrumentation, and the surgical methods ultimately are used as part of the described episode of care to improve the patient's health.

X. Treatment Cycles Incorporating Computer-Control and Data-Integration System, and/or Enabling Technologies for Performing Surgical Procedures.

A musculoskeletal surgical treatment cycle of the present disclosure can be used in performing surgical procedures on a patient. The treatment cycle of the present disclosure can employ at least two different surgical pathways, and these different surgical pathways can be used in to afford completion of a work-flow of surgical objectives with respect to portions of the patient in a complimentary manner. The surgical objectives can include access, manipulation, stabilization, and closure, and these objectives can be performed in simultaneous, serial, and/or iterative fashions.

As discussed below, the work-flow of the surgical objectives (including access, manipulation, stabilization, and closure) using the at least two different surgical pathways can be used in a surgical procedure to facilitate treatment of subject portions of a patient's spine. For example, when operating on the patient's spine and two different surgical pathways are utilized, a first surgical pathway can be used to provide access to, and manipulation and stabilization of the subject portions of the patient's spine at a primary surgical area, and a second surgical pathway can be used to provide access to, and manipulation and stabilization of the subject portions of the patient's spine at a secondary surgical area. And the manipulation and stabilization at the secondary surgical area can be used in adjusting and stabilizing the subject portions of the patient's spine at the primary surgical area to correspondingly improve surgical results at the primary surgical area. Furthermore, the surgical objectives of the spinal surgical procedure can be performed at the primary surgical area and the secondary surgical area simultaneously, serially, and/or iteratively. The performance of the surgical objectives can ultimately be used to treat portions of the patient's spine to aid in correction of spinal disease resulting from, for example, deformity, degeneration, or injury.

Figure 26:
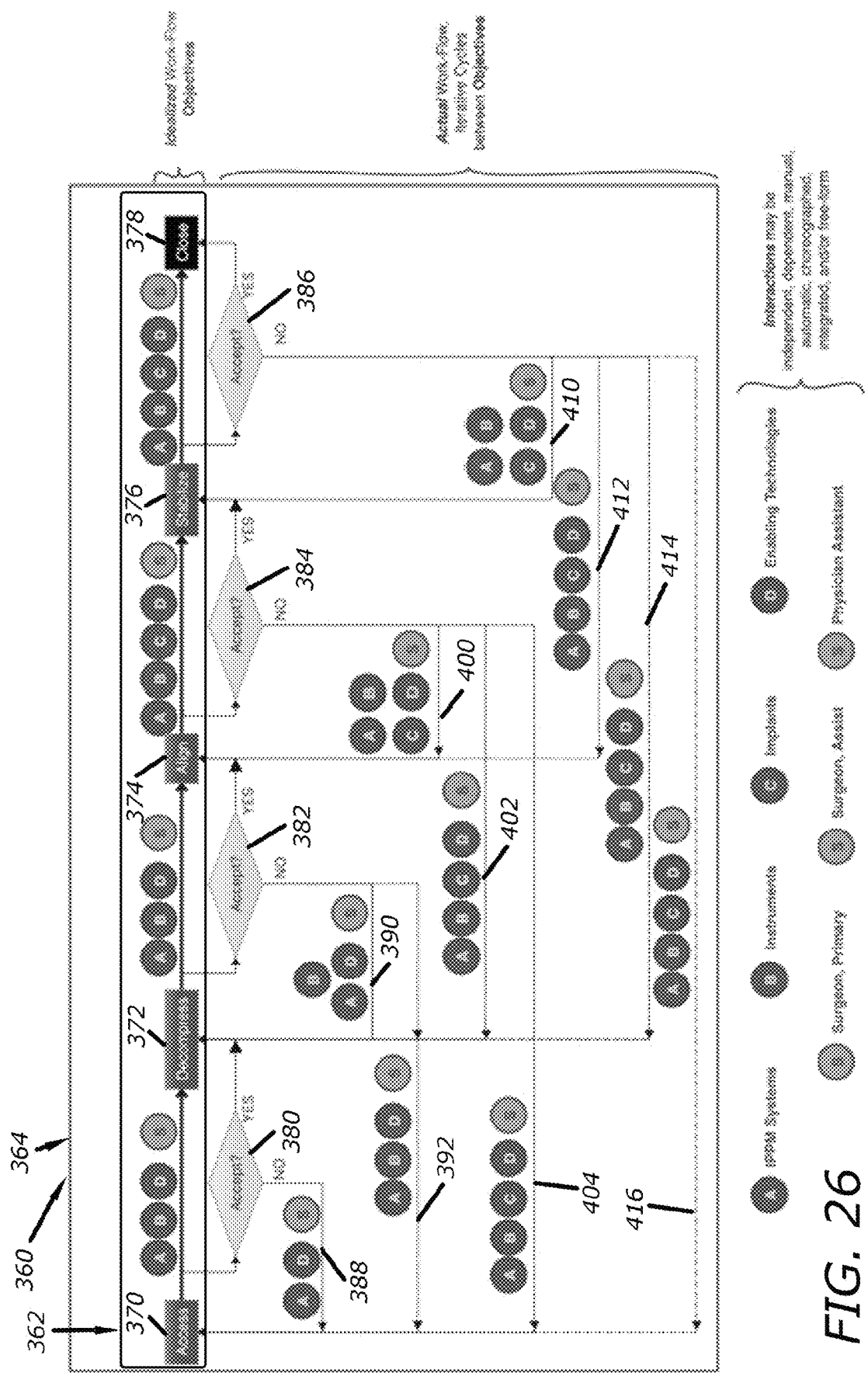
FIG. 26 is a flow-chart of an idealized work-flow of various surgical objectives, and an iterative work-flow affording repetition of the various surgical objectives to achieve a surgical result.

As depicted in FIG. 26, to afford performance a surgical procedure to treat subject portions of the patient's spine, a treatment cycle 360 can follow an idealized work-flow 362 of objectives from access 370, to manipulation (compression/decompression 372 and alignment 374), to stabilization 376, and then to closure 378. The surgical objectives of the idealized work-flow 362 can be performed simultaneously and/or serially. The treatment cycle 360 also can follow an iterative work-flow 364 that affords repetition of the various surgical objectives to improve the surgical result by creating beneficial feedback loops that facilitate such improvement. The surgical objectives of the iterative work-flow 364 can be performed simultaneously, serially, and/or iteratively.

At each of the surgical objectives, various processes, equipment (including a system A (including the patient-positioning system 10/110 and/or the computer-control and data-integration system 190), instruments B, and/or implants C (including the surgical componentry discussed herein)), and enabling technologies D can be used. To illustrate, the system A can be used to support and manipulate different portions of the patient relative to one another in a global manner and control the manipulation of the patient. Furthermore, the instruments B and the implants C can be used to manipulate different portions of the patient relative to one another in global and/or localized manners. For example, the instruments can include interbody implant trials and distractors, and the implants can include screws, rods, plates, interbody devices, and/or corpectomy devices. Additionally, the enabling technologies D can be using in visualizing and performing the surgical objectives, and for example, can include anesthesia/respiratory equipment, neuro-integrity monitoring equipment, surgical robotic system(s), navigation system(s), imaging system(s), AR system(s), VR system(s), and MR system(s), and other powered equipment. The surgical objectives can be performed by a primary surgeon, an assistant surgeon, a physician assistant, and/or other operating-room personal that are collectively referred to as surgeons/assistants and generally indicated by the letter S in FIG. 26. The surgeons/assistants S can use the system A, the instruments B, the implants C, and the enabling technologies D to perform the surgical objectives. And the performance of the surgical objectives by the surgeons/assistants S using the system A, the instruments B, the implants C, and the enabling technologies D can be dependent, independent, manual, automatic, free-form, choreographed, and/or integrated. As such, the robotic systems of the enabling technologies D can be used dependently by or independently of the surgeons/assistants S to perform each of the surgical objectives.

The idealized serial work-flow 362, as depicted in FIG. 26, begins with the access objective 370 to at least two different surgical pathways to the subject portions of the patient's spine. To perform the access objective 370, the surgeons/assistants S and/or the robotic systems of the enabling technologies D can manipulate the patient using the system A, the instruments B, and the enabling technologies D to provide access to the two surgical pathways. For example, surgeons/assistants S and/or the robotic systems of the enabling technologies D can manipulate the patient using the system A, can use the instruments B and/or the enabling technologies D to open the two surgical pathways, and/or can use the instruments B and/or enabling technologies D to facilitate such access. Besides using the enabling technologies D (such as the powered equipment) to open the two surgical pathways, the above-discussed enabling technologies can be used to facilitate such access.

After access 370 to the two surgical pathways is afforded, the idealized work-flow 362 can proceed to the surgical objective of compression/decompression 372. To perform the compression/decompression objective 372, the surgeons/assistants S and/or the robotic systems of the enabling technologies D can use the system A, the instruments B, and the enabling technologies D through one of the two surgical pathways in a global or localized manner to force compression/decompression on the subject portions of the patient's spine. In doing so, the system A, the instruments B, and/or the enabling technologies D can be used in distracting and correspondingly compressing or decompressing areas between adjacent vertebrae that are accessible via the one of the two surgical pathways.

After or simultaneous to compression/decompression 372 of the subject portions of the patient's spine through one of the two surgical pathways, the idealized work-flow 362 can proceed to the surgical objective of alignment 374. To perform the alignment objective 374, the surgeons/assistants S and/or the robotic systems of the enabling technologies D can use the system A, the instruments B, the implants C, and the enabling technologies D through the other of the two surgical pathways in a global or localized manner to force alignment on the subject portions of the patient's spine. In doing so, the system A, the instruments B, the implants C, and the enabling technologies D can be used in distracting and correspondingly aligning adjacent vertebrae relative to one another that are accessible via the other of the two surgical pathways.

After or simultaneous to compression/decompression 372 and alignment 374 of the subject portions of the patient's spine through the other of the two surgical pathways, the idealized work-flow 362 can proceed to the surgical objective of stabilization 376. To perform the stabilization objective 376, the surgeons/assistants S and/or the robotic systems of the enabling technologies D can use the system A, the instruments B, the implants C, and the enabling technologies D through either of the two surgical pathways in a global or localized manner to perform the stabilization objective 376 on the subject portions of the patient's spine. In doing so, the system A, the instruments B, the implants C, and the enabling technologies D can be used to maintain adjacent vertebrae in relation to one another. For example, the implants C (such as, for example, screws, rods, plates, interbody devices, and/or corpectomy devices (including the surgery componentry disclosed herein)) can be mechanically affixed/fastened to the vertebrae and to one another via either of the two surgical pathways to maintain the relationship between the adjacent vertebrae during the stabilization objective 376.

After stabilization 376 of the subject portions of the patient's spine, the idealized work-flow 362 proceeds to the surgical objective of closure 378. During the closure objective 378, the openings that afford access to the two surgical pathways can be closed and the idealized serial work-flow 362 of the treatment cycle 360 can be completed. All or parts of the idealized serial work-flow 362 can be performed simultaneously and/or serially through access 370, compression/decompression 372, alignment 374, stabilization 376, and closure 378 without having to repeat any of these surgical objectives.

The treatment cycle 360, as depicted in FIG. 26, also can afford repetition of the surgical objectives to improve surgical results. In doing so, decision markers can be used after performance each surgical subjective to determine if preceding surgical objective(s) are or are not yet acceptable, so that (if necessary) the preceding surgical objective(s) can be repeated. The decisions regarding acceptability of the surgical objective(s) can be based on one or more criteria sources including, for example, either surgeon-specific criteria/parameters, historical/reference parameters, or some combination of criteria/parameters. To illustrate, the decisions could be based on guidelines regarding optimal-outcome factors, professionally-recognized care pathways, payor or practice standards established by duly-entrusted bodies, and/or simply by a surgeon's clinical judgment and experience. In doing so, the one or more criteria sources can be informed by referential data and/or real-time acquired data developed from sources such as, for example, the enabling technologies D. Furthermore, the decisions regarding acceptability also could be presented to a surgeon as automated outcome choices that are auto populated using the criteria sources informed by the referential data and/or the real-time acquired data and presented via the computer/display 192 and/or the separate computer(s)/display(s) 292. Ultimately, after the decision that the surgical objective(s)

are not yet acceptable, the corresponding repetition thereof creates an iterative process that affords the iterative work-flow 364, as depicted in FIG. 26, that can improve the surgical results. All or parts of the iterative work-flow 364 can be performed simultaneously and/or serially through access 370, compression/decompression 372, alignment 374, stabilization 376, and closure 378, and during repetition thereof.

When following the iterative work-flow 364, and after the access objective 370 is initially completed (as described above for the idealized work-flow 362), it is determined at a first decision marker 380 if the results of the access objective 370 are acceptable. If acceptable, the iterative work-flow 364 can proceed to the compression/decompression objective 372. If not acceptable, the iterative work-flow 364 can return to and repeat via an iterative path 388 the access objective 370, and before doing so and if necessary, the surgeons/assistants S and/or the robotic systems of the enabling technologies D can manipulate the patient using the system A and the enabling technologies D. Thereafter, the access objective 370 (as described above in the idealized work-flow 362) can be repeated until acceptable, and the iterative work-flow 364 can proceed to the compression/decompression objective 372, and continue thereon as depicted in FIG. A.

When continuing to follow the iterative work-flow 364, and after the compression/decompression objective 372 is initially completed (as described above for the idealized work-flow 362), it is determined at a second decision marker 382 if the results of the compression/decompression objective 372 are acceptable. If acceptable, the iterative work-flow 364 can proceed to the alignment objective 374. If not acceptable, the iterative work-flow 364 can return to and repeat via an iterative path 390 to the compression/decompression objective 372, or return to and repeat via an iterative path 392 the access objective 370. Before returning to and repeating the compression/decompression objective 372 and if necessary, the surgeons/assistants S and/or the robotic systems of the enabling technologies D can manipulate the patient using the patient using the system A, the instruments B, and the enabling technologies D. And before returning to and repeating the access objective 370 and if necessary, the surgeons/assistants S and/or the robotic systems of the enabling technologies D can manipulate the patient using the system A, the instruments B, and the enabling technologies D. Thereafter, the iterative work-flow 364 can continue back to the compression/decompression objective 372 or the access objective 370, and continue thereon as depicted in FIG. 26.

When continuing to follow the iterative work-flow 364, and after the alignment objective 374 is initially completed (as described above for the idealized work-flow 362), it is determined at a third decision marker 384 if the results of the alignment objective 374 are acceptable. If acceptable, the iterative work-flow 364 can proceed to the stabilization objective 376. If not acceptable, the iterative work-flow 364 can return to and repeat via an iterative path 400 the alignment objective 374, return to and repeat via an iterative path 402 the compression/decompression objective 372, or return to and repeat via an iterative path 404 the access objective 370. Before returning to and repeating the alignment objective 374 and if necessary, the surgeons/assistants S and/or the robotic systems of the enabling technologies D can manipulate the patient using the patient using the system A, the instruments B, the implants C, and the enabling technologies D. Before returning to and repeating the compression/decompression objective 373 and if necessary, the surgeons/assistants S and/or the robotic systems of the enabling technologies D can manipulate the patient using the system A, the instruments B, the implants C, and the enabling technologies D. And before returning to and repeating the access objective 370 and if necessary, the surgeons/assistants S and/or the robotic systems of the enabling technologies D can manipulate the patient using the system A, the instruments B, the implants C, and the enabling technologies D. Thereafter, the iterative work-flow 364 can continue back to the alignment objective 374, the compression/decompression objective 372, or the access objective 370, and continue thereon as depicted in FIG. 26.

When continuing to follow the iterative work-flow 364, and after the stabilization objective 376 is initially completed (as described above for the idealized work-flow 362), it is determined at a fourth decision marker 386 if the results of the stabilization objective 376 are acceptable. If acceptable, the iterative work-flow 364 can proceed to the closure objective 378. If not acceptable, the iterative work-flow 364 can return to and repeat via an iterative path 410 the stabilization objective 376, return to and repeat via an iterative path 412 the alignment objective 374, return to and repeat via an iterative path 414 the compression/decompression objective 372, or return to and repeat via iterative path 416 the access objective 370. Before returning to and repeating the stabilization objective 376 and if necessary, the surgeons/assistants S and/or the robotic systems of the enabling technologies D can manipulate the patient using the patient using the system A, the instruments B, the implants C, and the enabling technologies D. Before returning to and repeating the alignment objective 374 and if necessary, the surgeons/assistants S and/or the robotic systems of the enabling technologies D can manipulate the patient using the patient using the system A, the instruments B, the implants C, and the enabling technologies D. Before returning to and repeating the compression/decompression objective 372 and if necessary, the surgeons/assistants S and/or the robotic systems of the enabling technologies D can manipulate the patient using the system A, the instruments B, the implants C, and the enabling technologies D. And before returning to and repeating the access objective 370 and if necessary, the surgeons/assistants S and/or the robotic systems of the enabling technologies D can manipulate the patient using the system A, the instruments B, the implants C, and the enabling technologies D. Thereafter, the iterative work-flow 364 can continue back to the stabilization 376, the alignment objective 374, the compression/decompression objective 372, or the access objective 370, and continue thereon as depicted in FIG. 26.

The use of the treatment cycle 360 is depicted in FIGS. 27A-31B for treating portions of a degenerative lumbar spine. While it is possible that the treatment cycle 360 could follow the idealized work-flow 362, it is expected and as depicted in the above-referenced figures, the treatment cycle 360 follows the iterative work-flow 364.

Figure 27A:
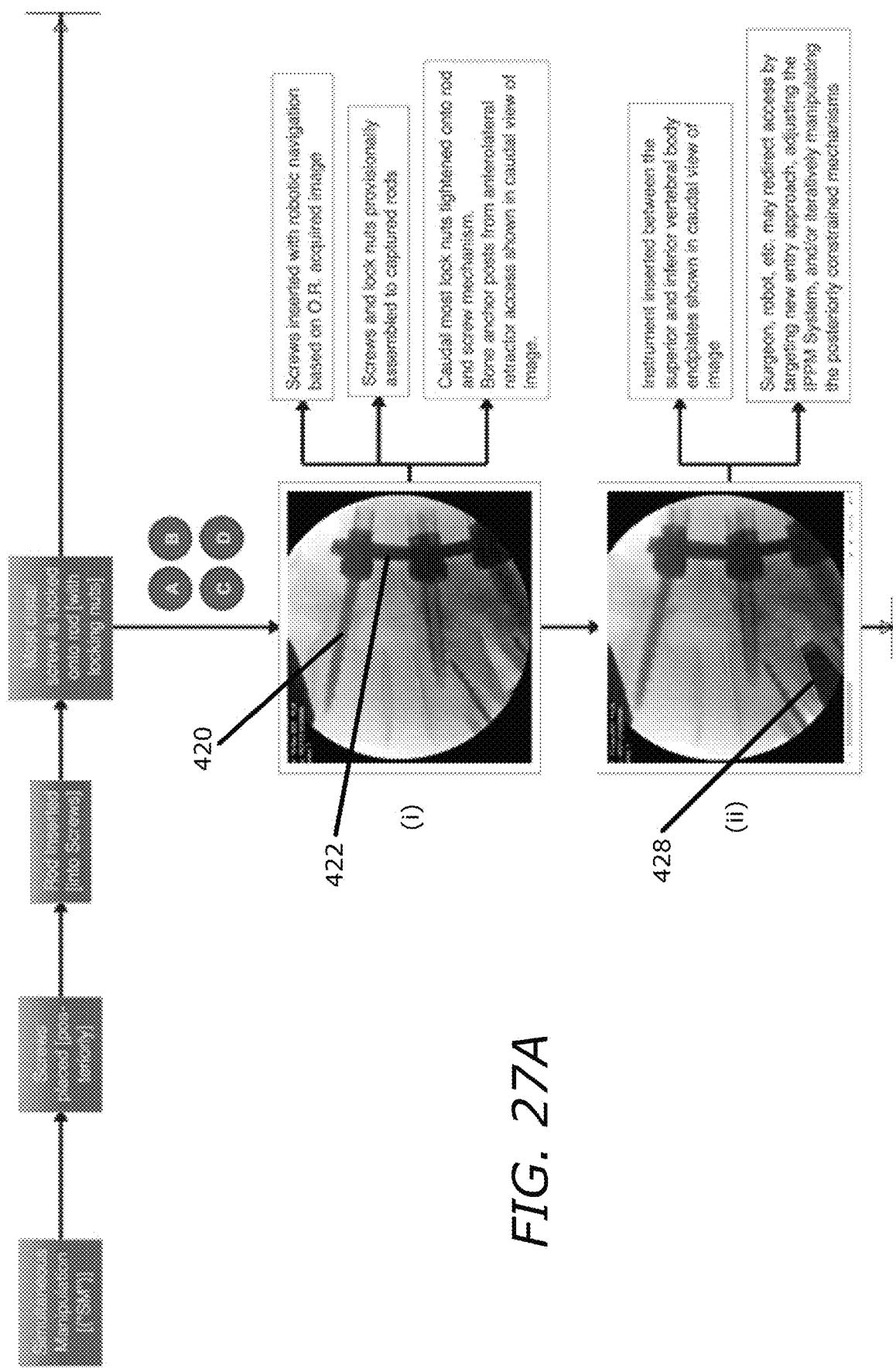
FIG. 27A is various successive lateral radiographic views of a human spine depicting correction of spinal disease using an iterative work-flow employing various instruments and implant componentry to facilitate decompression of two lowermost vertebrae.

As depicted in FIGS. 27A(i), 27A(ii), 27B(iii), 27B(iv), and 27B(v), two pathways to portions of the patient's spine S are provided to facilitate correction of spinal disease using the iterative work-flow 364. For example, as depicted in FIG. 27A(i), after access 370 is provided to the subject portions of the patient's spine, and after potentially, initially completing the compression/decompression objective 372 and the alignment objective 374 on these portions, screws 420 can be inserted posteriorly through one of the two surgical pathways into pedicles of various vertebrae to initially facilitate the stabilization objective 376. For example, the surgeons/assistants S and/or the robotic systems of the enabling technologies D can be used to facilitate placement of the screws 420. Furthermore, the surgeons/assistants S and/or the robotic systems of the enabling technologies D then can be used to insert a rod 422 through multiaxial end portions of the screws 420, and to place lock nuts 424 over the end portions of the screws 420 to hold portions of the rod 422 in position relative to the screws 420. As depicted in FIGS. 27A(i), 27A(ii), 27B(iii), 27B(iv), and 27B(v), the iterative work-flow 364 then can be used to facilitate the stabilization objective 376 beginning from lowermost to uppermost vertebrae of the subject portions of the patient's spine.

After placement of the screws 420, the rod 422, and the lock nuts 424, the caudal-most one of the lock nuts 424 first can be tightened on the caudal-most one of the screws 420 to initially complete the stabilization objective 376. Thereafter, the iterative work-flow 364 can return to and repeat (if necessary) the compression/decompression objective 372 and the alignment objective 374 to facilitate the stabilization objective 376 for the subject portions of the patient's spine using the screws 420, the rod 422, the lock nuts 424, and (if necessary) an interbody device 426. In doing so, the system A, the instruments B, the implants C, and the enabling technologies D can be used to facilitate the compression/decompression objective 372 and the alignment objective 374 on the subject portions of the patient's spine.

Figure 27B:
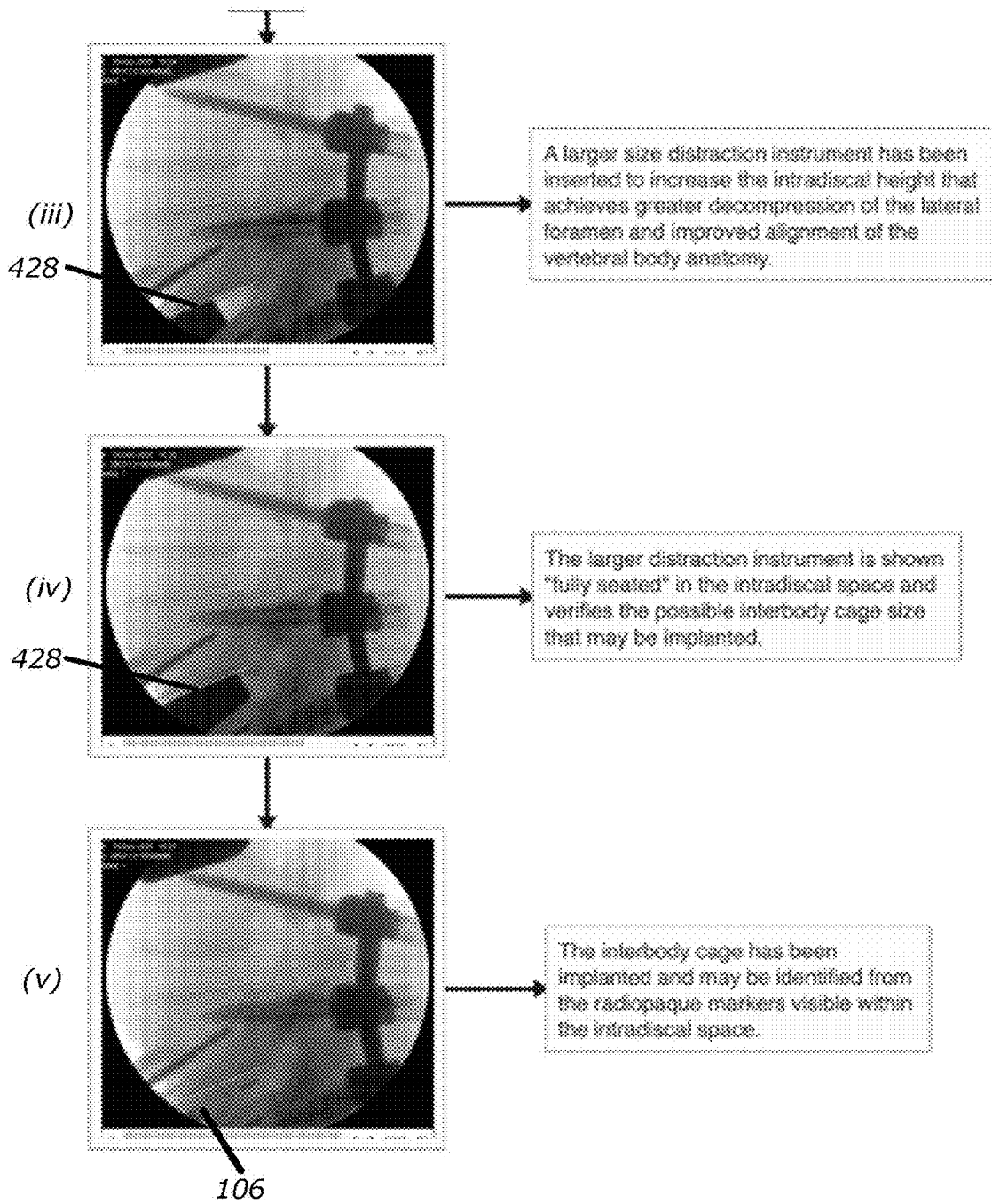
FIG. 27B is a continuation of FIG. 27A.

When returning to and repeating the compression/decompression objective 372 and the alignment objective 374 of the two lowermost vertebrae of the subject portions of the patient's spine, for example, the instruments B, as depicted in FIGS. 27A(ii), 27B(iii), and 27B(iv), such as successively larger distractors 428 can be inserted through the other of the two surgical pathways and placed into a disc space between the two lowermost vertebrae to impinge on corresponding superior and inferior endplates thereof to facilitate decompression and alignment thereof. After each placement of the successively larger distractors 428, the iterative work-flow 364 can return to and repeat the stabilization objective 376 so that the next caudal-most one of the lock nuts 424 can be tightened on the next caudal-most one of the screws 420 to maintain the decompression and alignment afforded by the successively larger distractors 428. Ultimately, as depicted in FIG. 27B(v), one of the interbody devices 426 can be inserted into the disc space between the two lowermost vertebrae to complete the stabilization objective 376 therefor.

The iterative work-flow 364 can be repeated for the next two lowermost vertebrae and so on until the stabilization objective 376 is completed for the subject portions of the patient's spine. To illustrate, the next caudal-most ones and so on of the locking nuts 424 can be sequentially tightened on the next caudal-most ones and so one of the screws 420, and additional ones of the interbody devices 426 can be sequentially inserted into the next caudal-most disc spaces and so on during repetition of the iterative work-flow 364 until the stabilization objective 376 for the subject portions of the patient's spine is complete. In doing so, the tightening of the lock nuts 424 on the screws 420 and the insertion of the interbody devices 426 during the stabilization objective 376 can be used in maintaining the decompression and alignment afforded by the iterative work-flow 364, as depicted in FIGS. 27A(i), 27A(ii), 27B(iii), 27B(iv), and 27B(v).

Other than the caudal-most one of the screws 420, the end portions of the screws 420 can translate along portions of the rod 422 during the iterative work-flow 364. And the rod 422 can be have an extended length and be shaped to constrain compression/decompression and/or alignment of the subject portions of the patient's spine to provide, for example, lordosis or kyphosis. As such, in addition to using the system A, the instruments B, and/or the enabling technologies D in and of themselves, the translation of the end portions of the screws 420 along the rod 422 (and the interaction therebetween) can be used to provide compression/decompression and/or alignment of the subject portions of the patient's spine as the patient is manipulated using the system A, the instruments B, and/or the enabling technologies D during the compression/decompression objective 372 and the alignment objective 374.

Figure 28A:
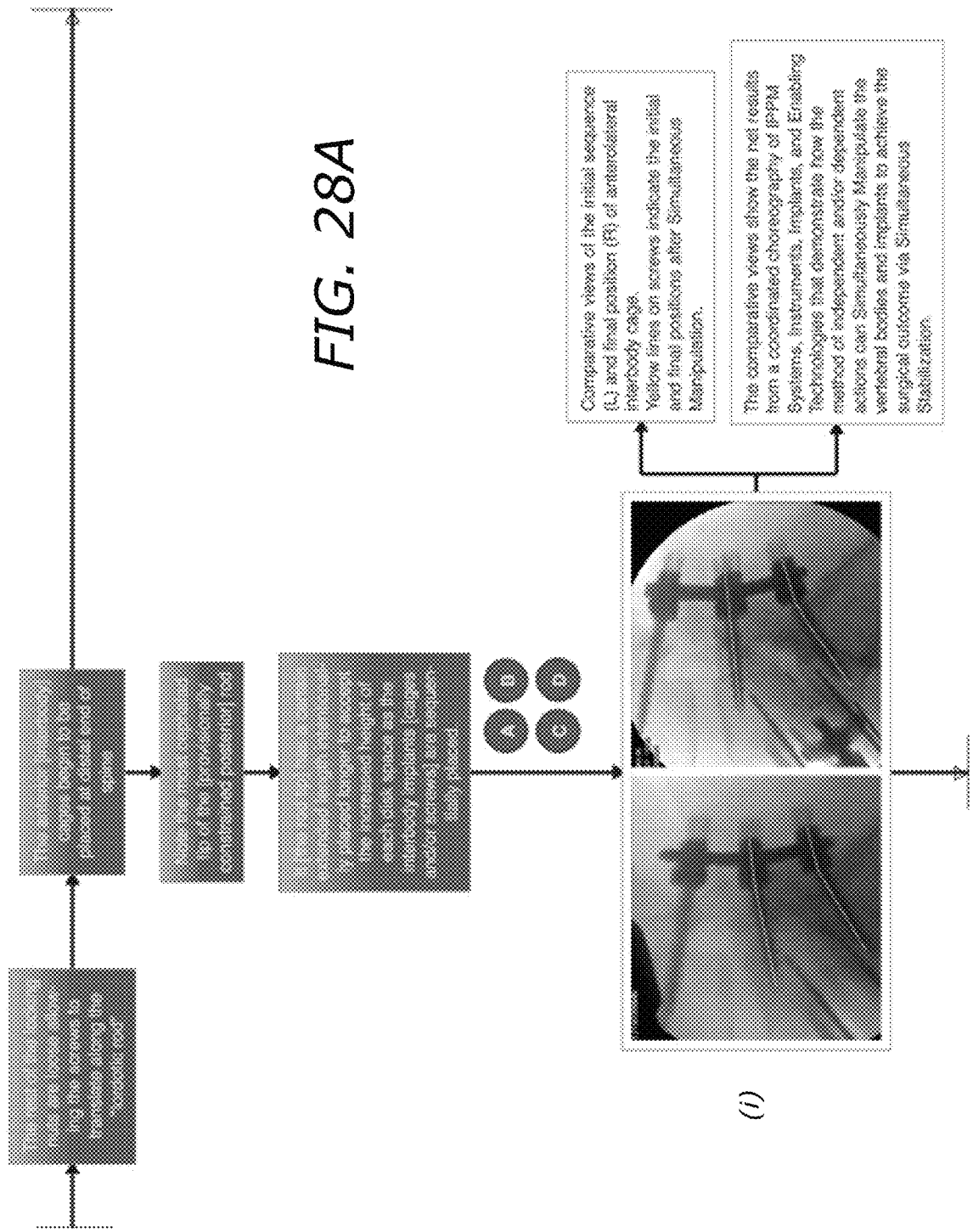
FIG. 28A is various lateral radiographic views of a human spine depicting comparative views of an initial sequence and a final position corresponding to decompression and alignment of the lowermost vertebrae.
Figure 28B:
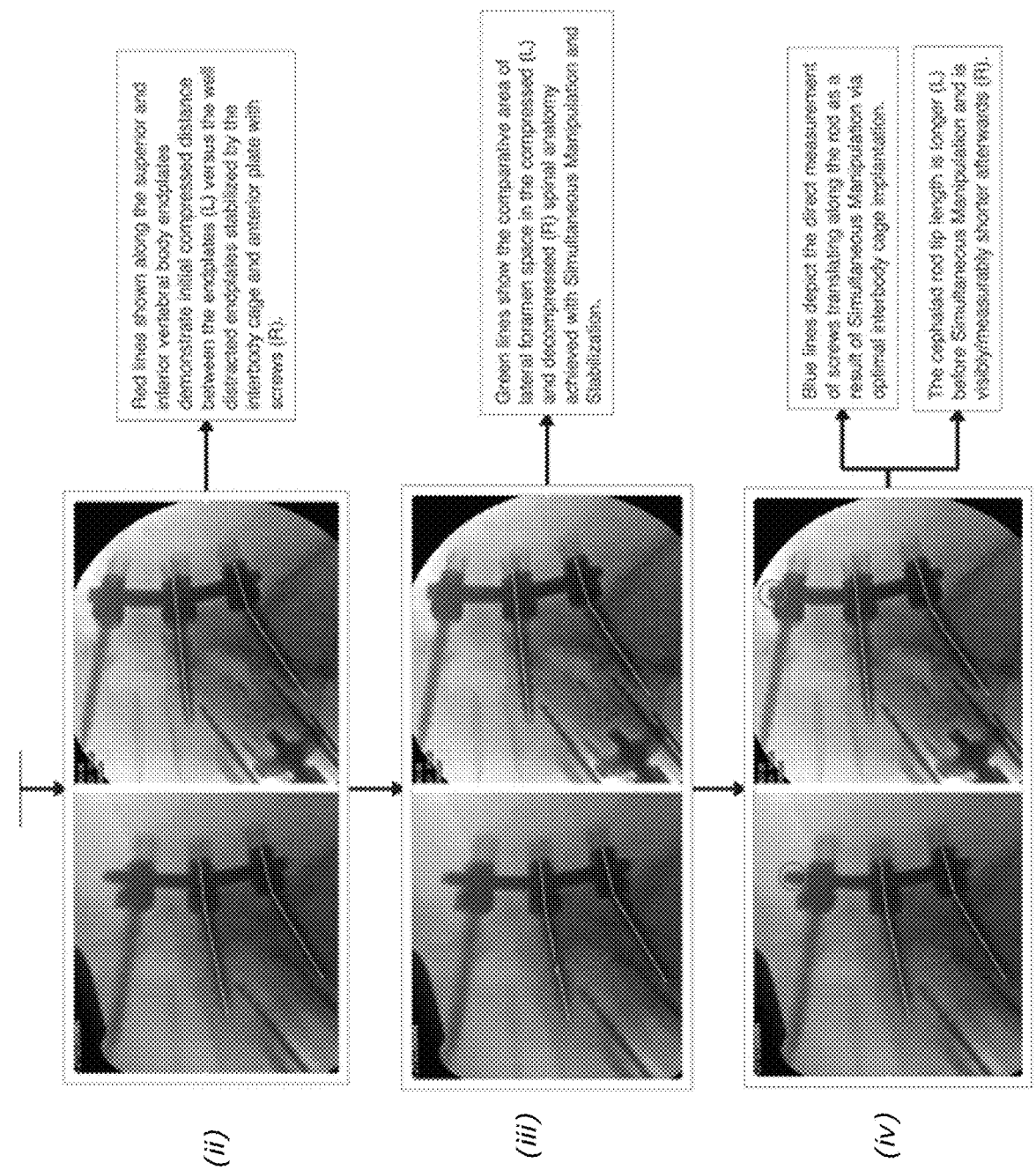
FIG. 28B is a continuation of FIG. 28A.

FIGS. 28A(i), 28B(ii), 28B(iii), and 28B(iv) depict comparative views of the subject portions of the patient's spine after the initial sequence (left-side) and final position (right-side) using the iterative work-flow 364. In FIGS. 28A(i), 28B(ii), 28B(iii), and 28B(iv), it can be seen that the iterative work-flow 364 can be used for decompression and alignment (via distraction) of the lowermost vertebrae, and that screws 420, lock nuts 424 and an interbody device 426 can be used for stabilization by maintaining the decompression and alignment. The red lines in FIGS. 28B(ii), 28B(iii), and 28B(iv) are used to depict the amount of distraction and corresponding decompression and alignment afforded by the iterative work-flow 364. Similarly, the green lines in FIGS. 28B(iii) and 28B(iv) show an increase of the size of the foramen space afforded by the decompression and alignment realized through the iterative work-flow 364. And, the blue lines in FIG. 28B(iv) shows translation of the end portion of the cranial-most one of the screws 420 along the extended length of the rod 424 afforded by the distraction afforded by the iterative work-flow 364. The extended length and the shape of the rod 424, and the use of the system A, the instruments B, the implants C, and the enabling technologies D can be used to facilitate the distraction, and corresponding decompression and alignment depicted in FIGS. 28A(i), 28B(ii), 28B(iii), and 28B(iv).

Figure 29A:
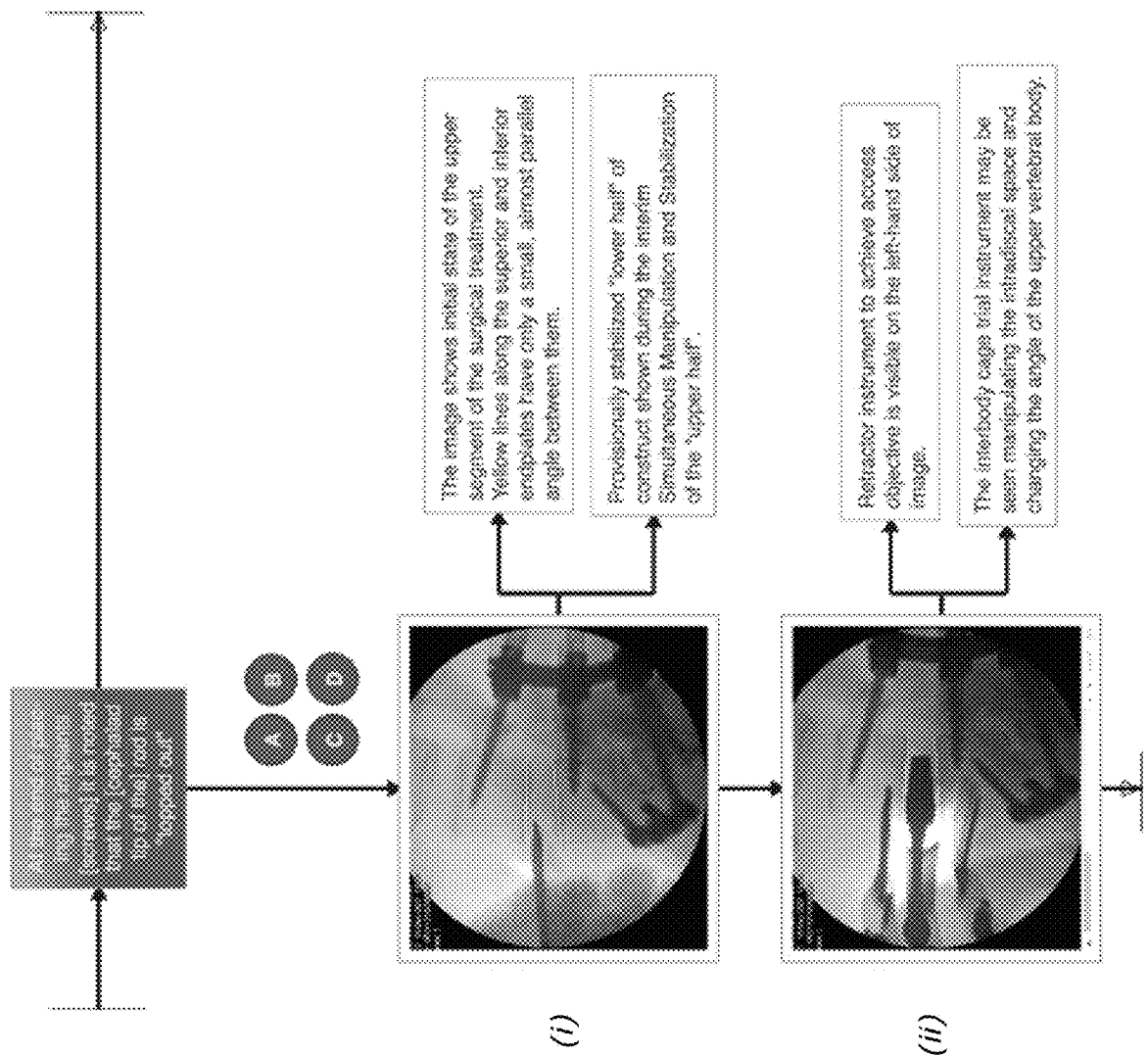
FIG. 29A is various successive lateral radiographic views of a human spine depicting correction of spinal disease using an iterative work-flow employing various instruments and implant componentry to facilitate decompression of two uppermost vertebrae.
Figure 29B:
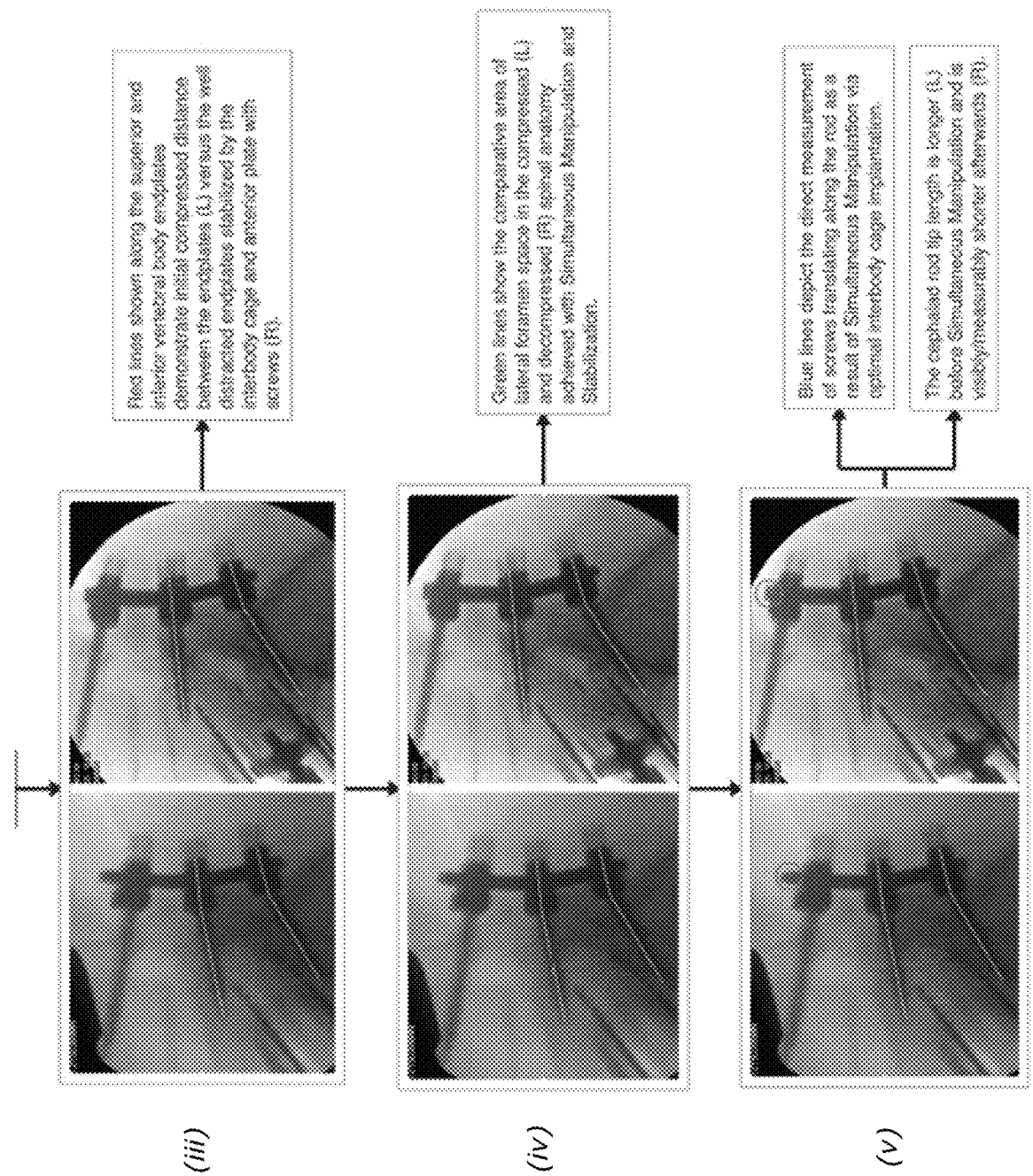
FIG. 29B is a continuation of FIG. 29A.

FIGS. 29A(i), 29A(ii), 29B(iii), 29B(iv), and 29B(v) depict successive use of larger interbody trial distractors of the instruments B to successively increase the distraction (and corresponding decompression and alignment) of a disc space between the two uppermost vertebrae of the subject portions of the patient's spine until one of the interbody devices 426 can be inserted into the disc space. FIG. 29A(i) depicts the initial positions of the two uppermost vertebrae of the subject portions of the patient's spine relative to one another. FIGS. 29A(ii), 29B(iii), and 29B(iv) depict the successive use of larger interbody trial distractors to successively increase the angle of the upper one of the two uppermost vertebrae of the subject portions of the patient's spine. And FIG. 29B(v) depicts the use of one of the interbody devices 426 to provide optimal distraction. The increased angle is depicted by the increasing angle of upper relative to lower yellow lines in FIGS. 29A(i), 29A(ii), 29B(iii), 29B(iv), and 29B(v).

Figure 30A:
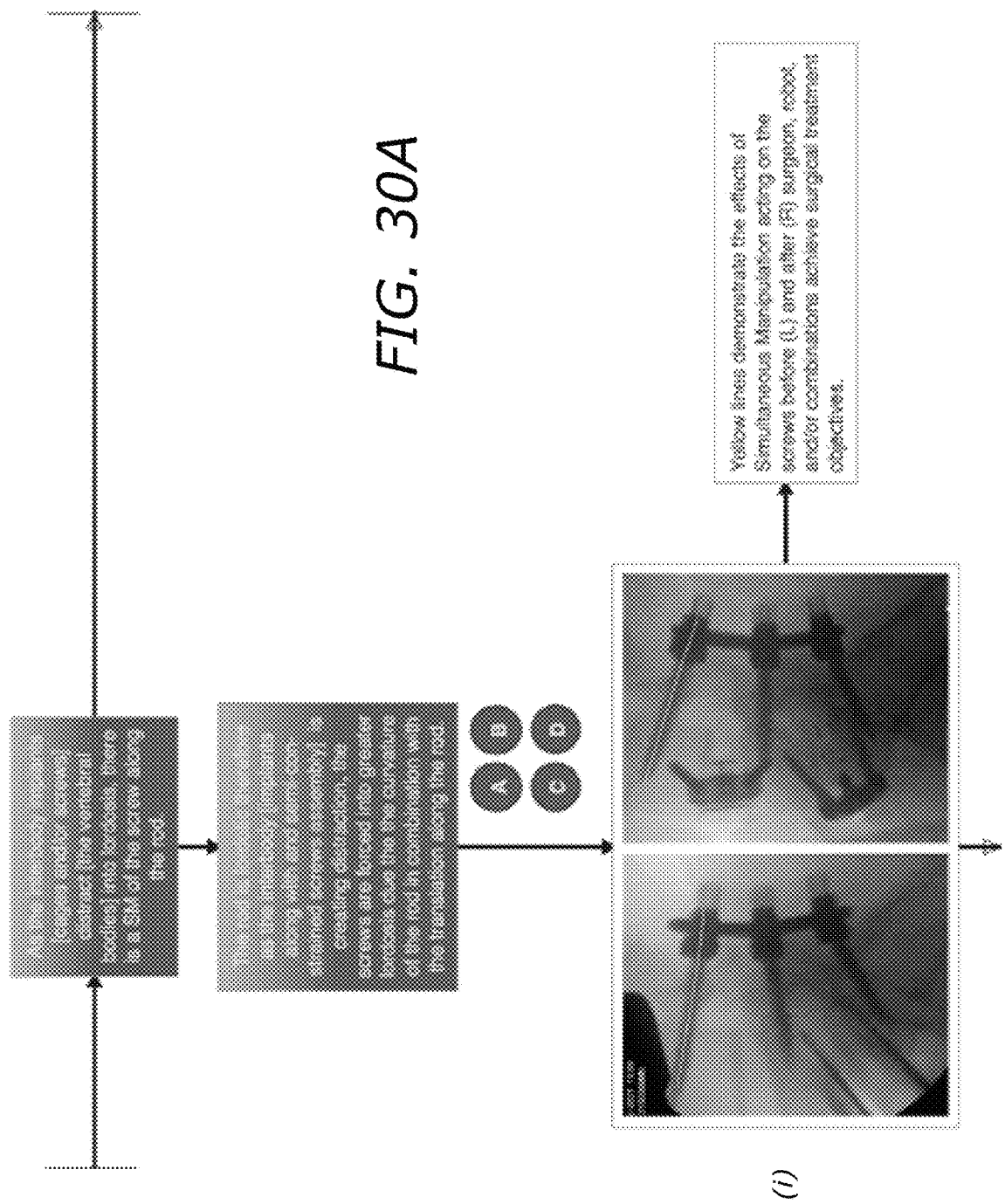
FIG. 30A is various lateral radiographic views of a human spine depicting comparative views of an initial sequence and a final position corresponding to decompression and alignment of the uppermost vertebrae.
Figure 30B:
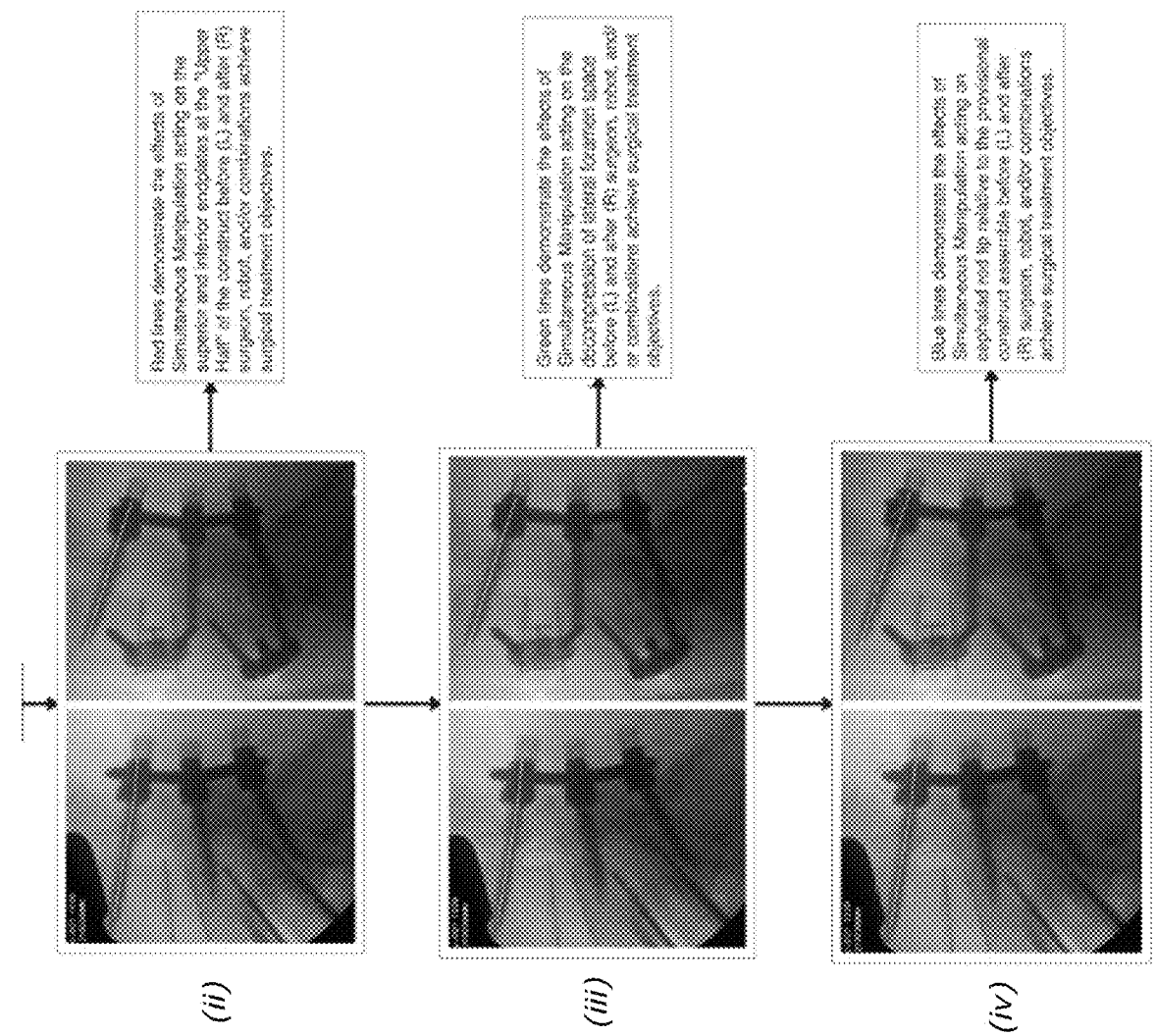
FIG. 30B is a continuation of FIG. 30A.

FIGS. 30A(i), 30B(ii), 30B(iii), and 30B(iv) depict comparative views of the subject portions of the patient's spine after the initial sequence (left-side) and final position (right-side) using the iterative work-flow 364. In FIGS. 30A(i), 30B(ii), 30B(iii), and 30B(iv), it can be seen that the iterative work-flow 364 can be used for distraction and corresponding decompression and alignment using the interaction of the end portions of the screws 420 along the rod 424. In doing so, the use of the system A, the instruments B, and/or the enabling technologies D at the compression/decompression objective 372 and the alignment objective 374, and the interaction of the end portions of the screws 420 along the rod 424 forces lordosis of the two uppermost vertebrae of the subject portions of the patient's spine. The red lines 30B(ii), 30B(iii), and 30B(iv) are used to depict the amount of distraction and corresponding decompression and alignment of the two uppermost vertebrae of the subject portions of the patient's spine realized through use of the interactions of the end portions of the screws 420 along the rod 424 and the iterative work-flow 364. Similarly, the green lines in FIGS. 30B(iii) and 30B(iv) show an increase of the size of the foramen space afforded by the decompression and alignment realized through use of the interactions of the end portions of the screws 420 along the rod 424 and the iterative work-flow 364. And, the blue lines in FIG. 30B(iv) shows translation of the end portion of the cranial-most one of the screws 420 along the extended length of the rod 424 afforded by the distraction afforded by the iterative work-flow 364.

Figure 31A:
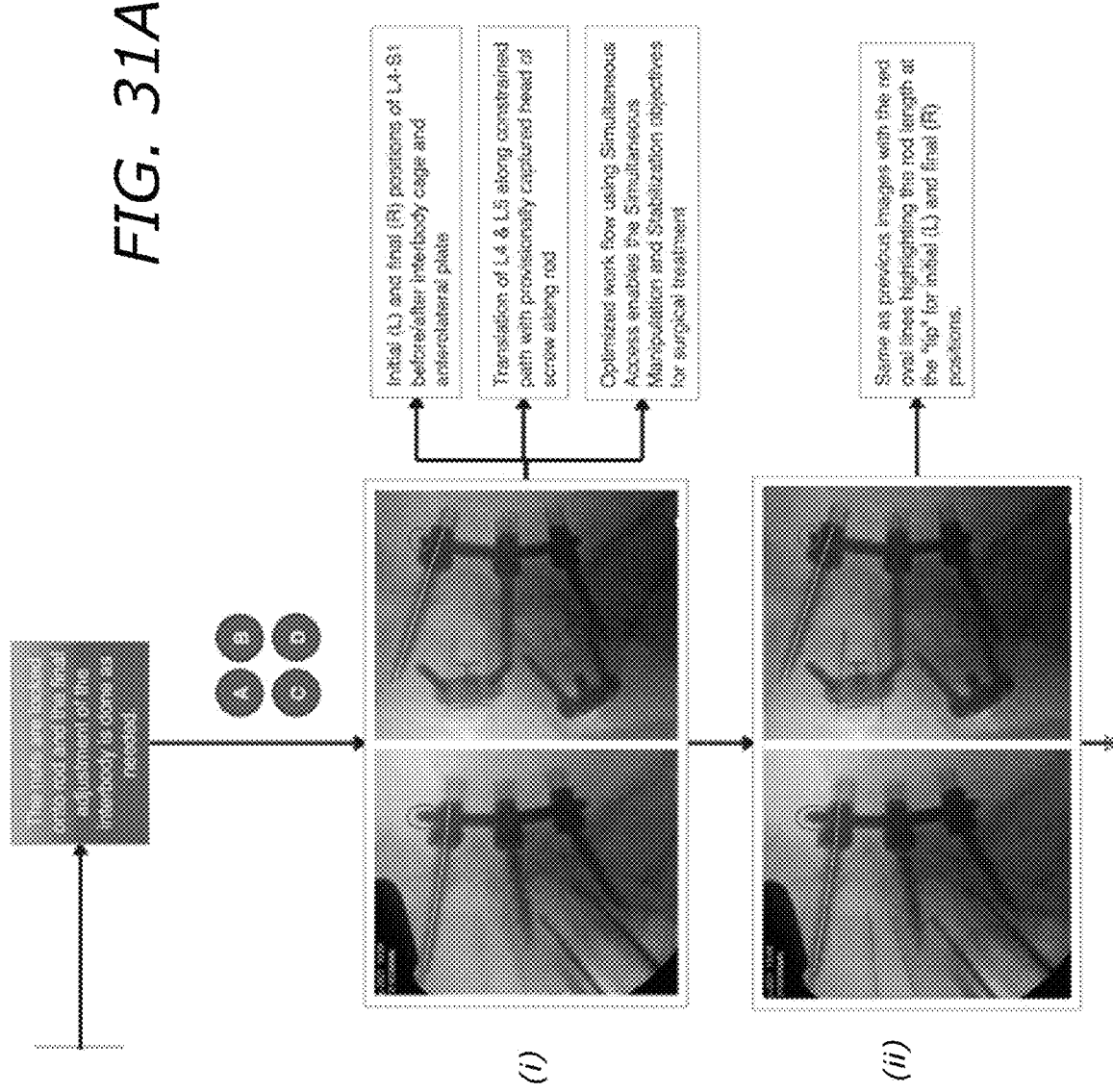
FIG. 31A is various lateral radiographic views, similar to FIG. 30A, of a human spine depicting comparative views of an initial sequence and a final position corresponding to decompression and alignment of the uppermost vertebrae.
Figure 31B:
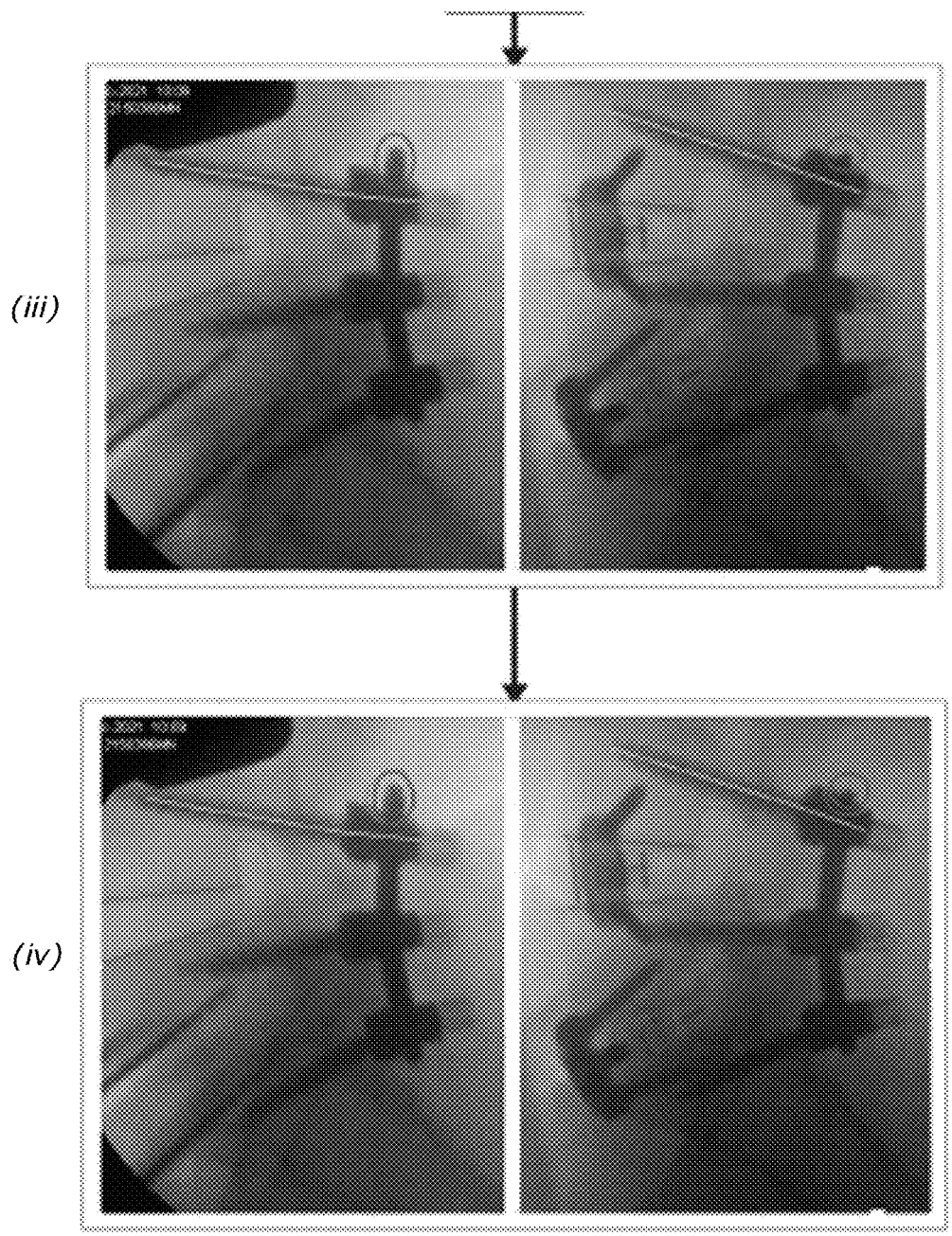
FIG. 31B is a continuation of FIG. 31A, similar to FIG. 30B.

FIGS. 31A(i), 31A(ii), 31B(iii), 31B(iv) depict comparative views of the subject portions of the patient's spine after the initial sequence (left-side) and the final position (right-side) using the iterative work-flow 364. The blue lines in FIGS. 31A(i), 31A(ii), 31B(iii), 31B(iv) depict initial and final positions of the cranial-most one of the screws 420 relative to the rod 424. And FIGS. 31A(i), 31A(ii), 31B(iii), 31B(iv) depict the use of one of the interbody devices 426 to complete distraction of the two uppermost vertebrae of the subject portions of the patient's spine. After distraction is completed, the cranial-most one of the lock nuts 424 first can be tightened on the cranial-most one of the screws 420 after being topped-out along the rod 422 to complete the stabilization objective 376.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (for example, all described acts or events may not be necessary to carry out the techniques). In addition, while certain aspects of this disclosure are described as being performed by a single module or unit for purposes of clarity, it should be understood that the techniques of this disclosure may be performed by a combination of units or modules.

We claim:

1. A method of performing spinal surgery on a patient's spine, the method comprising:
providing a structure to position a patient on a patient-positioning system;
articulating the patient between at least a first position and a second position;
accessing a first spinal portion of the patient via a first incision or incisions and accessing a second spinal portion of the patient via a second incision or incisions;
attaching a first spinal rod and a second spinal rod to a first vertebral body and a second vertebral body via a first surgical work-flow employing a first surgical pathway through the first incision or incisions, and simultaneously manipulating one of the first vertebral body and the second vertebral body via a second surgical work-flow employing a second surgical pathway through the second incision or incisions;
manipulating the first spinal portion of the patient using the first surgical work-flow employing the first surgical pathway via the first incision or incisions to facilitate distraction of the first vertebral body and the second vertebral body via manipulation of the first spinal portion;
manipulating the second spinal portion of the patient using the second work-flow employing the second surgical pathway via the second incision or incisions to facilitate implantation of a spinal implant in a disc space between the first vertebral body and the second vertebral body via manipulation of the second spinal portion; and
wherein manipulation of the first spinal portion and the second spinal portion of the patient can occur simultaneously to afford parallel performance of the first and second surgical work-flows; and
wherein the first spinal rod and the second spinal rod limit distraction of the first vertebral body and the second vertebral body.

2. The method of claim 1, wherein the first spinal portion can be located on a posterior portion of the patient's spine, and the second spinal portion can be located on a lateral portion of the patient's spine.

3. The method of claim 2, wherein each of the first and second surgical work-flows can include compression, decompression, alignment, and/or stabilization of the first spinal portion and the second spinal portion.

4. The method of claim 1, wherein the first surgical work-flow via the first surgical pathway at least partially relies on manipulation of a posterior portion of the patient's spine, and the second surgical work-flow via the second surgical pathway at least partially relies on manipulation of a lateral portion of the patient's spine.

5. The method of claim 1, wherein distraction of the first vertebral body and the second vertebral body, and implantation of the spinal implant can occur simultaneously via the parallel performance of the first and second surgical work-flows.

6. The method of claim 1, wherein articulation of the patient includes articulation of the patient into position relative to at least one surgeon in an ergonomically efficient manner to at least limit need for the surgeon to move from a single position during surgery.

7. A method of performing spinal surgery on a patient's spine, the method comprising:
providing a structure to position a patient on a patient-positioning system;
articulating the patient between at least a first position and a second position;
accessing a first spinal portion of the patient via a first incision or incisions and accessing a second spinal portion of the patient via a second incision or incisions;
attaching a first spinal rod and a second spinal rod to a first vertebral body and a second vertebral body via a first surgical work-flow using a first surgical pathway using the first incision or incisions, and simultaneously manipulating one of the first vertebral body and the second vertebral body via a second surgical work-flow using a second surgical pathway using the second incision or incisions;
manipulating the first spinal portion of the patient using the first surgical work-flow using the first surgical pathway via the first incision or incisions to distract the first vertebral body and the second vertebral body; and
manipulating the second spinal portion of the patient using the second surgical work-flow using the second surgical pathway via the second incision or incisions to implant a spinal implant into a disc space between the first vertebral body and the second vertebral body; p1 wherein manipulation of the first spinal portion and the second spinal portion of the patient can occur simultaneously to afford parallel performance of the first and second surgical work-flows;

wherein the first spinal rod and the second spinal rod limit distraction of the first vertebral body and the second vertebral body;

wherein the first spinal portion is a posterior portion of patient's spine, and the second spinal portion is a lateral portion of the patient's spine; and wherein each of the first and second surgical work-flows can include compression, decompression, alignment, and/or stabilization of the first spinal portion and the second spinal portion.

8. The method of claim 7, wherein the the first surgical work-flow via the first surgical pathway at least partially relies on manipulation of the posterior portion of the patient's spine, and the second surgical work-flow via the second surgical pathway at least partially relies on manipulation of the lateral portion of the patient's spine.

9. The method of claim 7, wherein distraction of the first vertebral body and the second vertebral body, and implantation of the spinal implant can occur simultaneously via the parallel performance of the first and second surgical work-flows.

10. The method of claim 7, wherein articulation of the patient includes articulation of the patient into position relative to at least one surgeon in an ergonomically efficient manner to at least limit need for the at least one surgeon to move from a single position during surgery.

11. A method of performing spinal surgery on a patient's spine, the method comprising:

positioning an apparatus to position a patient on a patient-positioning system;

articulating the patient between at least a first position and a second position;

accessing a first spinal portion of the patient via a first incision or incisions and accessing a second spinal portion of the patient via a second incision or incisions;

attaching a first spinal rod and a second spinal rod to one of a first vertebral body and a second vertebral body using a first surgical work-flow using a first surgical pathway via the first incision or incisions, and simultaneously manipulating one of the first vertebral body and the second vertebral body using a second surgical work-flow using a second surgical pathway via the second incision or incisions;

manipulating the first spinal portion of the patient using the first surgical work-flow using the first surgical pathway via the first incision or incisions to distract the first vertebral body and the second vertebral body; and manipulating the second spinal portion of the patient using the second surgical work-flow using the second surgical pathway via the second incision or incisions to implant a spinal implant into a disc space between the first vertebral body and the second vertebral body;

wherein manipulation of the first spinal portion and the second spinal portion of the patient can occur simultaneously to afford parallel performance of the first and second surgical work-flows;

wherein the first spinal portion is a posterior portion of patient's spine, and the second spinal portion is a lateral portion of the patient's spine; and wherein the first spinal rod and the second spinal rod limit distraction of the first vertebral body and the second vertebral body.

12. The method of claim 11, wherein the first surgical work-flow via the first surgical pathway at least partially relies on manipulation of a posterior portion of the patient's spine, and the second surgical work-flow via the second surgical pathway at least partially relies on manipulation of a lateral portion of the patient's spine.

13. The method of claim 12, wherein distraction of the first vertebral body and the second vertebral body, and implantation of the spinal implant can occur simultaneously via the parallel performance of the first surgical work-flow and the second surgical work-flow.

14. The method of claim 11, wherein manipulation of the first spinal portion and the second spinal portion of the patient occur simultaneously via performance thereof by different surgeons.

15. The method of claim 11, wherein the parallel performance of the first and second surgical work-flows can be performed by different surgeons.

16. The method of claim 1, wherein manipulation of the first spinal portion and the second spinal portion of the patient occur simultaneously via performance thereof by different surgeons.

17. The method of claim 1, wherein the parallel performance of the first and second surgical work-flows can be performed by different surgeons.

18. The method of claim 7, wherein manipulation of the first spinal portion and the second spinal portion of the patient occur simultaneously via performance thereof by different surgeons.

19. The method of claim 7, wherein the parallel performance of the first and second surgical work-flows can be performed by different surgeons.

* * * * *